(12) United States Patent
Tsai

(10) Patent No.: US 12,714,642 B2
(45) Date of Patent: Aug. 25, 2026

(54) DEVICE, BODY, METHOD AND SYSTEM FOR HEALTH-CARE

(71) Applicant: TAO MINING CO., LTD., Taipei (TW)

(72) Inventor: Ching-Fu Tsai, Taipei (TW)

(73) Assignee: TAO MINING CO., LTD., Taipei (TW)

( * ) Notice: Subject to any disclaimer, the term of this patent is extended or adjusted under 35 U.S.C. 154(b) by 378 days.

(21) Appl. No.: 17/894,757

(22) Filed: Aug. 24, 2022

(65) Prior Publication Data

US 2023/0123064 A1 Apr. 20, 2023

Related U.S. Application Data

(62) Division of application No. 17/801,698, filed as application No. PCT/CN2020/088533 on Apr. 30, 2020, now Pat. No. 12,396,922.

(51) Int. Cl.
*A61H 39/04* (2006.01)
*A61H 39/00* (2006.01)
(Continued)

(52) U.S. Cl.
CPC ........... *A61H 39/04* (2013.01); *A61H 39/002* (2013.01); *A61H 39/06* (2013.01); *A61H 39/08* (2013.01);
(Continued)

(58) Field of Classification Search
CPC ...... A61H 39/04; A61H 39/002; A61H 39/06; A61H 39/08; A61H 2201/0019;
(Continued)

(56) References Cited

U.S. PATENT DOCUMENTS 2,704,539 A * 3/1955 Fisher .................. A61B 5/4827 600/557
5,224,469 A * 7/1993 Mocny .................. A61H 39/04 600/587
(Continued)

FOREIGN PATENT DOCUMENTS

CN 201959428 U 9/2011
CN 203647552 U 6/2014
(Continued)

OTHER PUBLICATIONS

International Search Report issued in corresponding International Patent Application No. PCT/CN2020/088533 on Jan. 28, 2021, consisting of 8 pp. (English Translation Provided).

*Primary Examiner* — Shaun L David
*Assistant Examiner* — Cherie M Poland
(74) *Attorney, Agent, or Firm* — Volpe Koenig

(57) ABSTRACT

A health care device includes a health care body for positioning a body part of a user, so as to maintain a first specific positional relationship with the body part, wherein the body part has an acupoint; an acupoint work piece for performing a health care work onto the use through the acupoint; and a work piece holder having a first end connected to the health care body and a second end for fixing the acupoint work piece, so that under the first specific positional relationship, the acupoint work piece performs the health care work under the condition that the acupoint work piece has a second specific positional relationship with the acupoint. A health care body, method and system are also provided.

20 Claims, 22 Drawing Sheets

(51) Int. Cl.

| | |
|---|---|
| ***A61H 39/06*** | (2006.01) |
| ***A61H 39/08*** | (2006.01) |
| ***A61N 2/00*** | (2006.01) |
| ***G16H 70/20*** | (2018.01) |

(52) U.S. Cl.
CPC ............. *A61N 2/006* (2013.01); *G16H 70/20* (2018.01); *A61H 2039/005* (2013.01); *A61H 2201/0119* (2013.01); *A61H 2201/0192* (2013.01); *A61H 2201/0196* (2013.01); *A61H 2201/0207* (2013.01); *A61H 2201/0221* (2013.01); *A61H 2201/0278* (2013.01); *A61H 2201/1207* (2013.01); *A61H 2201/1246* (2013.01); *A61H 2201/1436* (2013.01); *A61H 2201/1604* (2013.01); *A61H 2201/1607* (2013.01); *A61H 2201/1635* (2013.01); *A61H 2201/164* (2013.01); *A61H 2201/165* (2013.01); *A61H 2201/1659* (2013.01); *A61H 2201/1671* (2013.01); *A61H 2201/1676* (2013.01); *A61H 2201/5071* (2013.01); *A61H 2203/0468* (2013.01); *A61H 2205/022* (2013.01); *A61H 2205/04* (2013.01); *A61H 2205/067* (2013.01); *A61H 2205/081* (2013.01); *A61H 2205/108* (2013.01)

(58) Field of Classification Search
CPC .... A61H 2201/0192; A61H 2201/0196; A61H 2201/0207; A61H 2201/0221; A61H 2201/0278; A61H 2201/1207; A61H 2201/1246; A61H 2201/1436; A61H 2201/1604; A61H 2201/1607; A61H 2201/1635; A61H 2201/164; A61H 2201/165; A61H 2201/1659; A61H 2201/1671; A61H 2201/1676; A61H 2201/5071; A61H 2203/0468; A61H 2205/022; A61H 2205/04; A61H 2205/067; A61H 2205/081; A61H 2205/108; A61H 1/0285; A61H 1/0288; A61H 2005/065; A61H 2005/067; G16H 70/20; A61N 2/006
See application file for complete search history.

(56) References Cited

U.S. PATENT DOCUMENTS

| | | | | | |
|---|---|---|---|---|---|
| 5,584,854 | A * | 12/1996 | Minarik | A61H 39/04 | 606/203 |
| 5,601,596 | A * | 2/1997 | Lam | A61F 5/30 | 606/201 |
| 8,048,099 | B2 * | 11/2011 | Maliglowka | A61B 17/3417 | 606/172 |
| 8,257,285 | B2 * | 9/2012 | Cook | A61H 1/0218 | 5/915 |
| 2004/0158176 | A1 * | 8/2004 | Park | A61H 39/04 | 601/134 |
| 2011/0178360 | A1 * | 7/2011 | Gavish | A61H 39/04 | 600/15 |
| 2021/0308008 | A1 * | 10/2021 | Dong | A61N 1/0456 | |

FOREIGN PATENT DOCUMENTS

| | | | | |
|---|---|---|---|---|
| CN | 105056403 A | 11/2015 | | |
| CN | 205094975 U | 3/2016 | | |
| CN | 105816316 A | 8/2016 | | |
| CN | 106726467 A | 5/2017 | | |
| CN | 107213013 A | 9/2017 | | |
| CN | 108524257 A | 9/2018 | | |
| CN | 109011174 A | 12/2018 | | |
| CN | 209137280 U | 7/2019 | | |
| CN | 209809013 U | 12/2019 | | |
| KR | 20020028036 A | 4/2002 | | |
| WO | 2015037763 A1 | 3/2015 | | |
| WO | WO-2018133254 A1 * | 7/2018 | | A61N 1/0452 |

* cited by examiner

DEVICE, BODY, METHOD AND SYSTEM FOR HEALTH-CARE

FIELD OF THE INVENTION

This invention relates to device, body, method and system for health-care, especially based on Chinese medical theory.

BACKGROUND OF THE INVENTION

Those who lose their health will know that being sick-free or painless is a great blessing in life. Human nature is usually greedy for life and fear of death. It is one of the big desires of ordinary people to get life prolonged. Everyone seems to agree that prevention is better than cure, but facing the life journey of birth, aging, sickness and death, not everyone has the opportunity or the perseverance to always pay attention to prevention. The invention follows the examples of Chinese genius doctors Hua Tuo and Bian Que, and is intended to bring health and happiness to mankind.

SUMMARY OF THE INVENTION

Because of extremely diversified disclosures of the present inventions, for facilitating the examination, it is to be noted that the claims currently on file of this application are directed to seek patent protections for specific inventions exemplarily embodied in FIGS. 8 to 9. In a nutshell, the present invention hopes to bring Hua Tuo and Bian Que back to the world. The ensuing questions are: how to perform dreams or ideals? How to put imagination into practical content? Because the issues are very big, readers or examiners are invited to carefully review and examine what are described later.

Traditional Chinese medicine or acupuncture theory is scattered in ancient Chinese classics, where the cores or subtle implications thereof are described in Huangdi Neijing Suwen and Lingshu. Among these cultural treasures, not only can we see the exquisiteness of medical theory or logic, but they have also been seen clinically effective or widely reported, which cannot be extensively quoted here. For example, acupuncture and moxibustion have an extremely effective analgesic effect in clinic. For some organic diseases, even cancer, the analgesic effect can be maintained for a week, which was frequently reported.

It is recorded in Bazheng Gods Thesis Chapter, Suwen, The Yellow Emperor's Neijing that "observing the unknown world means that the shape, Qi (vitality), Rong and Wei are invisible to the outside, while the artisan (i.e., medical expert, good doctor, Hua Tuo or Bian Que) knows it well. Because coldness and warmth of the sun, emptiness of the moon, ups and downs of the air in the four seasons, and variation of their combination, participation and arrangement are invisible to or unrecognized by the general public but detected by the artisan, it is thus called observing the unknown world. Only those that are communicable to the infinite future can be passed on to later generations. That which has been detected different by an artisan is externally invisible and cannot be entirely seen. As it is not tangibly visible and cannot be tasted, it is thus called unknown world, just like talking about the gods." The Chapter continues with "an insufficient evil means one Qi deviated from eight righteous ones. A normal evil happens when one labors to sweat into running into an evil wind through the muscles texture, which, however, is mild and not felt or discernible." The Chapter continued, "a superior artisan cures a potential sickness upon its burgeoning through detecting Qis by checking 9 pulses in three parts and is so qualified through adequately regulating the Qis. An inferior artisan gets rid of a sickness after it has been fully developed or the yin-yang Qi balance has been broken. The need to cure a sickness after it has been developed comes from the failure in detecting the yin-yang unbalance after checking 9 pulses in the three parts. Such artisan can cure a sickness after it has been fully developed to be known as the sickness and eventually cure the sickness through confirmations from 9 pulses in the three parts. Such artisan is merely like a doorkeeper because it cannot know what is budding but what the outbreak evil is." The purpose and ideal of the present invention are to equip every family or person with a caring superior doctor for life.

Patent examination is to determine whether an invention is different from conventional technology, and an invention is often originating from the lack or deficiency of conventional technology. The value of an invention to mankind depends on how much it contributes to society, while the patent or market value of an invention depends on whether it is practical or not, and whether all competitors have to follow suit. Although the various values of an invention are not necessarily related to the level of technology or the exquisiteness of the skill, it should be worthy of our efforts if we can solve some problems systematically or comprehensively and achieve the effects of human relief. What follow will make a comprehensive review of related technologies. Wherever there are discussions about existing technologies, it is possible to capture the source of creativity or ideas.

From the perspective of "modern science", acupuncture is a phenomenon of sensing along the meridians. This can be learned by those with acupuncture experience: when acupuncture is applied at the correct point, the patient will feel a special feeling along the corresponding meridian lines, and the sensation is often soreness, swelling, numbness, heat, cold, pain or electric shock. These feelings may appear alone, but most of them are mixed feelings of soreness, swelling, and numbness. The ancient book names it qi sense, or qi obtainment. At this time, the person applying the needle will also perceive that the needle seems to be sucked, awkwardly operable, not easy to turn, and not easy to be pulled out.

In modern society having a tight or speedy pace, acupuncture and moxibustion have once been ignored because of their insufficient consideration in hygiene in the past and slow curative effects. There are lots of efforts tried to construct modern theories therefor, such as material metabolism theory or energy metabolism theory, either from molecular, atomic or particle aspect or wave aspect where it is proposed that there are many optically non-uniform tubular structures or sheet-like structures in the human body, in which because they are not uniform either in the performance of visible light reflection, refraction coefficient, and polarization ability, or in the performance of infrared or microwave reflection, refraction coefficient, and polarization ability, an electromagnetic wave guide system is thus formed in the human body.

According to the above, the internal qi of traditional Chinese therapy is the relationship among electromagnetic waves, meridians and acupoints in the human body. The slow speed of the sense transmission along the meridians is derived from the group speed of the waveguide. Meridians are not like blood vessels, lymphatic vessels or nerve fibers with clear boundaries, but are strip-shaped areas with fuzzy boundaries and with the highest conductance value on the central axis of each meridian, while radially diminishing gradually from the central axis. Specifically, the meridians are like mountains, and the acupoints are like individual peaks on the mountains. In other words, the center of the acupuncture point is the top of each mountain peak. However, with continuous conductance measurement at the same point, the conductance of the human body fluctuates with the time, which the ancients called the Ziwu Liuzhu, that is, the qi and blood flow dynamically circulate in the body in accordance with the season, moon phase, and time. Nevertheless, this conductance change happens throughout the entire body and does not seriously affects the difference between acupoints and non-acupoints, so it does not affect the clinical conductance measurement.

What surprises the modern science (especially modern medicine or modern biology) is the holographic phenomenon of the acupoints. Regarding the so-called holographic phenomenon, regardless of ear acupuncture or foot massage, in a small area, there are acupoints reflecting all the organs of the whole body. Even in each small finger joint area, acupoints reflecting all the organs of the whole body can be found. In other words, when a certain organ has a disease, not only the conductance of the main acupoints on the 14 main meridians increases significantly, but also in the local area of the specific acupoint. It is thus quite possible that every point in the body is a micro meridian point.

When a person's physiological or psychological state changes, the probability distribution curve of conductance data in any area of the body will change accordingly, and it seems that the mystery of the meridian points will eventually be revealed. Meridians are electrical channels, optical channels, microwave channels, sound channels, and chemical channels. What is measured on the meridian points is not skin resistance, but body conductance or electric field strength, where conductance is proportional to the square of the conductance field strength. It thus can be concluded that the meridian system in the scriptures is a kind of energy distribution in the human body. This energy distribution can neither be seen with the naked eye, nor be tracked with a scalpel.

The energy distribution structure in the preceding paragraph is understood by modern physics as a dissipative structure being a dynamic structure. It exists by continuous energy supply and fully conforms to the dissipative structure formed by electromagnetic waves, which cannot be simply understood from physiology. But understanding Chinese classical medicine in this way may bring physiology, biology and medicine to a new milestone. The so-called dissipative structure, taking a dynamic waterfall as an example, can only exist when there is a source of high water level, and once the source stops, the waterfall will disappear quickly. Because the prerequisites are that the structure is constantly consuming energy, it is called the dissipative structure. Others, such as candles, mountain springs, fountains, lanterns, sky lanterns, flutes, whirlpools, tornadoes, and lightning, are all living structures. Once the environment is closed, this structure will instantly disappear.

The meridian system is a kind of dissipative structure formed by electromagnetic standing waves. Because two waves can exist in the same position and superimpose or cancel each other, new interference waves are formed by point-by-point construction or destruction. When the human body meridian system may be understood as a three-dimensional electromagnetic standing wave interference pattern, we could then find ways to interfere and/or change its interference pattern to change the energy distribution and restore the patient's health. It may be magical, but for thousands of years, the ancestors used a single needle to heal countless ancestors with Qi and blood circulation, deficiency syndrome, excessiveness syndrome, Ziwu Liuzhu, qi obtainment, yin and yang, tonic method, and draining method.

Regardless of whether coming from health concerns, the traditional acupuncture has been developed to include many other ways to change the aforementioned interference patterns, such as hyperthermia, infrared therapy, spectrum therapy, electroacupuncture, laser acupuncture, microwave acupuncture, etc., all of which belong to non-intrusive or non-contact interference and change media.

The dissipation theory or structure mentioned above, where playing Dongxiao involves the same theory and the human body is also a resonant cavity, contains numerous electromagnetic standing waves interacting with each other to form complex standing wave interference patterns while acupuncture points play a key role in interfering with individual or combined standing waves, because acupuncture points always have the highest conductance, or are the places where the peaks of individual or combined electromagnetic standing waves are located. Specifically, when a certain organ has a problem, its natural frequency or accompanying standing wave changes. As a result, the energies of some acupuncture points increase or decrease abnormally, and the resistances on the acupuncture points in turn decrease or increase accordingly. Therefore, no matter whether it is intrusive or non-intrusive, we can build/destroy/correct individual or total standing waves through acupoints, so that the organs or patients can return to normal/healthy.

Light and microwaves are both electromagnetic waves. The light commonly referred to by the world refers to visible light, which only occupies a very small share of the entire electromagnetic spectrum. The transmission speed of a single electromagnetic wave is extremely fast (up to 300,000 kilometers per second), but the transmission speed of the meridian sense is less than ten centimeters per second (where it takes tens of minutes to convert from one interference pattern to another). The reason is that the number of electromagnetic waves in the body is counted in billions (or even tens or tens of billions), and the propagation speed of the summing signal is accordingly reduced. This is also the reason why we often hear that any object is nothing but a mass of vibration frequencies.

Non-intrusive acupuncture and moxibustion, such as laser acupuncture, although it is called a kind of acupuncture, there is no actual puncturing action. Because it is non-intrusive, safe and painless, it is easily accepted by patients. More and more new treatments having effects not inferior to the traditional acupuncture and moxibustion are reported. Although the laser acupuncture is a painless and safe treatment option, clear dosage guidelines have yet to be established. Other non-intrusive acupuncture and moxibustion, such as the now popular physiotherapy techniques, such as hyperthermia, infrared therapy, spectrum therapy, electroacupuncture, microwave acupuncture, etc., because they all introduce electromagnetic waves of different wavelengths into the human body, they should also have standards to be established.

In Western society, microwaves with a frequency range of 40~70 GHz are used to balance and treat the unique frequency (characteristic frequency) of a person (or even a specific organ), which is called Microwave Resonance Therapy (MRT). Of course, microwave acupuncture is also based on acupuncture. It is a method of infusing microwaves with the same frequency as the characteristic frequency into acupuncture points or directly irradiating acupoints to generate resonance to treat diseases by connecting a microwave antenna to the needle handle. In practice, it is found that the resonance frequency in the meridian channels will flow from the internal organs to tips of the fingers or toes, and then be reflected back to the organs. When sick, the amplitude of the inherent frequency (characteristic frequency) will decrease or disappear. An extra energy with a very low energy level (one millionth or one billionth of a watt) can restore the resonance frequency of a specific organ or human body to the standard value, thereby helping/completing the treatment.

In 1934, the professional Journal of Acupuncture and Moxibustion in China published the clinical application of electroacupuncture for the first time. In the late 1950s, there were extensive researches on electroacupuncture and it was used clinically for surgical anesthesia. Modern electroacupuncture devices are small in size, often powered by batteries. Small clips are connected to the wires from the device and clamped on the acupuncture needles inserted into the body. When the electric current is generated, the patient feels a slight beating or fluctuating sensation, as if a feather is sweeping the skin. Of course, we should avoid placing electrodes near the heart, or not allow current to pass through the midline of the body (i.e. an imaginary line from the nose bridge to the navel).

Either the "Bianque-A Microwave Acupuncture Apparatus" developed by Beijing Electronic Instrument Factory in 1980, or the various acupoint therapy apparatuses that have sprung up recently, in order to meet the needs of different diseases or different parts, their appearances look very different. They all suffer from difficulties in accurately aligning with the acupoints, but require the assistance of the patient or the user, such as trying to keep the affected part deliberately attached to or close to the working surface of the respective instrument, in order to better obtain the service or treatment effect from the instrument. In addition, in order to cope with the continuous renovations of laser acupuncture, hyperthermia, infrared therapy, spectrum therapy, electroacupuncture, microwave acupuncture, etc., because of their different working principles, if we want to obtain the therapeutic effect, the instrument itself or the working point, working surface or working area of the instrument must be different. In order to have a relatively accurate positional relationship between the acupuncture points on the human body to be worked and the working point, working surface or working area of the instrument, for achieving a better therapeutic effect, usually the manual of the instrument will explain how to self-adjust the body posture, or the operator will assist in adjusting the patient's posture for receiving instrument/treatment services. For example, the circular or arcuate treatment instrument is mostly used for joints, shoulders, waist, etc.; the elongate treatment instrument is suitable for acupoints in elongate regions such as the spine or body part. Nevertheless, as mentioned above, either the user needs to cause her/his the affected part close to or attach to the working point, working surface or working area of the instrument, or it is necessary to put the instrument directly on the patient's body, so that the working point, working face or working area of the instrument can serve (e.g., irradiate) the affected area. At this time, the patient's affected part (or acupuncture points on the affected part) and the working point, working surface or working area of the instrument in fact only maintain in a rough, roughly or almost correct relative positional relationship. This kind of arrangement not only results in the positional discrepancy between the instrument and the patient, but also in angular relationship therebetween, and even in the distance therebetween. The correctness or properness of the distance between the instrument and the affected part of the patient usually determines whether the best effect can be obtained, or whether it will unfortunately cause harm to be detailed later.

If we use the microwave acupoint therapy device for explanations in details, we can understand the aforementioned difficulties. Specifically, the effects of microwave therapy are usually based on thermal effects, but non-thermal effects cannot be ruled out (e.g., local microwave acupoint stimulation may be conducted through the meridians for producing effects of "guiding qi to where the disease exists"). The maximum microwave radiation can penetrate 50 millimeters into the body surface, and the body temperature of the exposed area can be significantly increased, which is deeper and stronger than the heat of moxibustion. The distance between the patient's affected part (or acupuncture points on the affected part) and the working point, working surface or working area of the instrument as mentioned in the preceding paragraph obviously determines whether the affected part will be burned by moxibustion.

When microwaves irradiate the human body, there are mainly two effects, namely thermal action and thermal external action (which is different from ultrashort wave, where the latter is produced by electric current, while the former by electromagnetic wave). The so-called thermal action comes from the oscillation of electrolyte ions and electrolyte dipoles, or the high-frequency oscillation of water molecules, which causes the tissue to generate a large amount of heat energy, thereby increasing the tissue temperature, dilating blood vessels, and accelerating blood flow (which can increase by 50%). The so-called thermal external effects are the special physiological effects of microwave radiation on the human body (where the relevant research is still limited), and known to possibly affect the function of the nervous system (where short-term or low-dose radiation can enhance the excitatory process, while long-term or large-dose radiation reverses inhibition). Compared with infrared radiation and other light radiations, microwave has a deeper effect, that is, it is difficult for infrared to penetrate the lipid layer, but microwave can penetrate the lipid layer to reach the muscle layer. The therapeutic effects thereof are not to be detailed here.

Microwave acupuncture has a strong qi sense (swelling, heavy, soreness, numbness, feeling hot, sensation of movement and warmth) to the meridian points, and can be conducted along the meridian for sweating (similar to the Burning Mountain Fire skill). Further, the strength of the qi sense can be quantitatively controlled by the microwave treatment instrument. Microwave acupoint irradiation has functions of both acupuncture and warm moxibustion. When the microwave power reaches a certain value, there is a high-frequency discharge phenomenon on the needle tip, but its power (2 watts) is much less than that of the microwave physiotherapy machine (200 watts), so no special protection is required.

Microwave acupuncture point therapy instruments can be roughly divided into three categories: one is microwave radiator (which is straightforwardly directed at acupoints or lesions and is similar to laser irradiation at acupoints), the second is microwave acupuncture (therapy) instrument (having a radiation antenna needle for radiating acupuncture points), and the third is the magnetic needle.

Microwave acupuncture point radiators or microwave radiators generally include 5 types: (1) circular radiator, whose opening end is round, and whose external shape is hemispherical, cylindrical, reflective mask-shaped, etc., mainly used for acupoints at joints, shoulders or waist, or breast lesions; (2) elongate (or rectangular) radiator having a rectangular opening, and mostly used in elongate areas of the body, such as the spine or body part; (3) saddle-shaped radiator having a concave surface, used to treat acupuncture points at large areas such as waist, knee, back, hip, buttocks, chest or abdomen, and capable of being directly attached to the affected surface for treatment; (4) focusing radiator, with a diameter of 1, 1.5, or 3.5 cm, used to treat small parts not suitable for treatments by the aforementioned three kinds; and (5) ear radiator, which is dedicated to irradiate ear acupoints or be inserted into the ear canal for treatment and has a replaceable rubber sleeve.

The microwave acupuncture instrument consists of four parts: a DC variable power supply, a microwave oscillator (1,000~2,000) MHz, an output coaxial cable and a microwave antenna. The microwave antenna includes a needle clamp, a needle, and a spiral spring coaxial transmitter. The needle is a component of the co-radiation antenna. The microwave energy is transmitted to the needle via the coaxial cable by the oscillator, and then radiated to the human body acupoints).

To understand the microwave Di needle, we need to know first that the Di needle is one of the nine ancient needles, and has a large body and a round tip. It is a kind of round and slightly pointed acupoint work piece with a thick needle body and a millet-like tip. It is used to press the acupoints for guiding the qi and blood without piercing into the skin. In "Yellow Emperor's Neijing Lingshu, Nine Needles Twelve Originals Chapter," it is disclosed that "the third Di needle has three and a half body inches . . . , the tip sharpness is as sharp as a millet, and is used to press the pulse without piercing into the skin, so as to cause Qi." In "Yellow Emperor's Neijing Lingshu, Nine Needles Theory Chapter," it is disclosed that "the Di needle, which is imitated from the millet's sharpness, is three and a half body inches long and mainly used for pressing the pulse to get the qi to drain the evil qi." The microwave Di needle is produced through combining the modern microwave physiotherapy, and was successfully trial-produced in Mainland China in 1979. The microwave needles have functions and effects of traditional Di needle, finger needle and moxibustion through merging the performance and characteristics of modern low-frequency and high-frequency electrotherapy.

The principles for acupoint selection and combination compatibility in microwave therapy are the same as those for other acupoint therapies, and can be either based on three options of local, adjacent, and remote selection methods, and/or the tenderness point or the focus of the disease. Of course, it is also possible to select acupuncture points in consideration of the characteristics of the instrument, such as its number of output heads or the stretching range.

When irradiating acupoints on the limbs, the patient usually takes the lying or sitting position, while the recommended distance between the radiator and the acupoint skin is 10-15 cm (or 5 cm at the ear). As for the time and power thereof, they depend on the specific condition (e.g. for ears 8-10 watts, neck 20-40 watts, chest and abdomen 60-100 watts, waist and back 80-120 watts, for 5-10 minutes). Regarding the acupoints around the knee and shoulder joints, saddle-shaped radiators are often used; for the acupuncture points on the chest, abdomen, back and waist, the patient should choose the supine or prone position, for being served by the round or elongate radiator; as for the neck acupoints and ear points, patients often use the sitting position, for being served by the circular or convergent radiators.

From the above discussions, we can find that all existing technologies encounter the following problems. Taking the microwave radiator as an example, whether using a universal bracket to fix the microwave radiator at the "ideal" position, or manually pressing the Di needle microwave radiator on the acupuncture point to be treated, the relative positions (including distance and orientation) between the working point of the instrument and the acupuncture point have not been or cannot be accurately determined. Although the acupuncture points in Chinese medicine are not a point with almost no area in the geometric imagination, but a small area, it is obvious that if we want to maintain the correct or better relative positions between the working point of the instrument and the acupuncture point for a period of time with either universal joints or artificial efforts, it is significantly difficult, at least because (1) the adjustment range of the working point of the instrument has its limit, and (2) the patient will inevitably adjust her/his posture unconsciously.

The problem in the preceding paragraph will bring about another problem, that is, because the theoretical relative position cannot be obtained or ensured, it is impossible for the instrument to be scientifically qualitative (effect) and quantitative (for receiving the instrument service time and intensity). Therefore, taking the microwave therapeutic apparatus as an example, we need be very careful to prevent high temperature and overheating. Although it is theoretically known that the relative position should be adjusted so that the patient has a comfortable warm feeling and soreness, but not a tingling sensation, each person has nevertheless different feelings or tolerance levels, so that there are qualitative or quantitative difficulties. For patients with low pain tolerance, the dosage may not be enough to obtain curative effect; on the contrary, for patients with high pain tolerance, the dosage may actually be excessive to cause temporary or permanent hurt.

The problem mentioned in the preceding paragraph makes it easy for us to understand another problem: when the acupoints are located near the face, brain, eyes, ovaries or testicles, in order to avoid excessive radiation or damage, the existing technology has to recommend a distance of 5 cm and a power of not more than 15 watts, for a time less than 10 minutes. It is thus known that if we can get the theoretical relative position, we can not only get great flexibility in designing the instrument or using the design, but also ensure the obtainment of the effects.

The problem mentioned in the preceding paragraph makes us understand the importance of being "qualitative" or "quantitative". In detail, the guarantee of the relative position in theory allows us to accurately study the nature and extent of the effects of the instrumental acupoint work piece. For example, when patients have severe local organic or ischemic vascular diseases, excessive radiation not only does not improve their blood circulation, but also often aggravates local hypoxia due to temperature rise, so both doctors and patients have psychological barriers in using the instrument. However, if the theoretical guarantee of relative positions, after successful qualitative and quantitative researches, even for patients with active tuberculosis, high fever, bleeding-prone diseases, advanced hypertension, heart failure, fractures and the inability to clearly express the microwave needle sensation of the group of patients and children, they will no longer belong to the group that is not suitable for acupoint microwave therapy.

After solving the problems mentioned in the preceding paragraph, we will be inspired to understand: because of the qualitative and quantitative success, we can design an effect-focused instrument acupoint work piece (because the efficiency or effect is sufficient, there is no need for too large or wide working area) without harming innocent adjacent people or staff. This is because long-term microwave radiation is harmful to the human body since the microwave therapy device leaks a small amount of microwaves and radiates to the surrounding space, which may cause injuries to the innocent staff.

After solving the problems mentioned in the preceding paragraph, we can't help but jump for joy because the following various effects will be not only be guaranteed, but easier to be achieved through the establishment of relevant theoretical relative positions. Specifically, high intensity, high dose (3 W/cm2) ultrasound (acoustic) waves have inhibitory or destructive effects on various tissues and organs, causing irreversible changes in tissue morphology; but (A) low-intensity, medium and small dose (therapeutic dose) ultrasound effects on peripheral nerves and spinal cord are first excited and then inhibited, so it has analgesic effect on neuralgia; (B) a small dose can congest heart capillaries and increase interstitial cells, so it can improve blood circulation; (C) although the sensitivity of each part of the kidney to ultrasonic waves is different (where the cortex close to curve tubules are the most sensitive, while the medullary collecting duct and the urinary tube connective tissue basement membrane are the least sensitive), the therapeutic dose of ultrasound acting on the kidney area has functions of expanding blood vessels and promoting renal blood circulation; (D) high-dose ultrasound on the ovaries or testicles has inhibitory or even damaging effects, so some people have tried it to be used for birth control in recent years; (E) therapeutic dose ultrasound can improve skin nutrition, promote dermal regeneration, strengthen epithelial formation, and cause increased sweat gland secretion; (F) multiple applications of small dose ultrasound waves can stimulate the growth of bone callus (while it should be noted that a slightly larger dose of 10 minutes will slow down the bone healing).

The effects mentioned in the preceding paragraph were obtained through the establishment of the relative position in theory. We may wonder whether these effects also exist when applied in other therapies. According to physical experiments and clinical practices, the magnetic line bundle of the magnetic needle (non-intrusive) can penetrate the human body skin to a depth of 6~9 cm, which is approximately equivalent to the depth of a traditional acupuncture needle. It is speculated that when a certain acupoint in the human body receives stimulation, it will cause the local cell receptors to produce bioelectricity, and at the same time there will be "qi" in the meridian points, which is to be conducted along the meridian system. The sensed conduction route is consistent with the route predicted by the acupuncture theory. Medical practices have also verified that even though the effects of magnetic fields or magnetic lines of force and needle (intrusive) acupuncture may not be equivalent, their effectiveness is quite consistent. For example, using warm water to soak one's feet and then massage and magnetically absorb the Yongquan acupoint is very effective in treating BPH (prostatic hyperplasia) nocturia and frequent urination. Here is a brief description of acupoint magnetotherapy (using a magnetic device with north and south poles to a certain acupoint in the human body) to examine its applicability as follows.

In "Historical Records-Biography of Bian Que Cang," it describes the use of magnets to treat diseases in 180 BC. In the second century BC, the Chinese pharmacology monograph "Shen Nong's Materia Medica" officially listed magnets as medicines: "Magnes tastes hot, has a cold nature and mainly cures body paralysis, rheumatism, pain in the limbs unable to hold things . . . and deafness". In the Collection of Famous Doctors by Tao Hongjing in the Southern and Northern Dynasties, the effects of magnets are recorded: "they foster kidney qi, strengthen bone qi, nourish essence, eliminate trouble, lubricate joints, eliminate carbuncle, fistula, cervical nucleus, sore throat, epilepsy in children". Yang Shangshan's "Yellow Emperor's Neijing Taisu" in Sui Dynasty, when interpreting the phrase "walking with heavy footsteps" in the "Lingshu, Meridian" Chapter, collaterally mentioned the external effect of the magnet: "What heavy footsteps mean that you put the magnets in your shoes fastened by straps to feel heavy upon walking. After you feel it becomes light, you can gradually increase the weight in order to enhance the fire qi. If you recover from the disease, you should gradually remove the magnets. This is the ancient method of treating the kidney." "Precious Prescriptions for Emergency Medicine" in Tang Dynasty has a prescription for treating a bleeding wound: "Applying the magnet powder to the wound for relieving pain and stopping bleeding." It is described in Li Shizhen's masterpiece of pharmacology "Compendium of Materia Medica" in Ming Dynasty: "A true magnet of a bean size, calcined with pangolin, is ground to be collected in a line shape which is then wrapped in the new cotton to be inserted into the ear. Then, a piece of pig iron is kept in the mouth, and the deafness is cured after the ear feels wind and rain." Inspired by the "Compendium of Materia Medica" magnet therapy for deafness, acupoint magnetic therapy emerged in mainland China in the early 1960s. Some acupuncture scholars in Shanghai tried to combine acupuncture with a magnetic field and use magnetic needles (magnetized needles) to effectively treat tinnitus; in 1965, medical workers in Hunan also combined the magnetic field theory and the meridian theory to achieve clinical treatment results; major breakthroughs in the application of magnetic therapy in the 1970s were caused by easy accessibility of permanent magnet materials (mainly rare earth cobalt alloys, permanent magnet ferrites, and aluminum nickel cobalt magnets) so that the acupoint magnetic therapy becomes popular. For example, in 1970, it was successfully trial-produced magnetic beads for acupoint application to treat diseases in Baotou City, Inner Mongolia; since 1973, rare earth alloy magnetic sheets were first used for magnetic therapy of various diseases in Hunan Province; in 1974, Beijing Acupuncture workers cooperated with some researchers to turn a static magnetic field into a dynamic magnetic field to make a rotating magnetic therapy machine, which expanded the treatment range to a certain extent and improved the curative effect on certain diseases; in 1978, the first mainland China conference of magnetic therapy scientific research collaboration was held in Xuzhou City, Jiangsu Province.

Since 1980, acupoint magnetotherapy has made unprecedented progress. While the magnetostatic method of fixing magnetic beads or sheet on a certain acupuncture point or part has little to do with the present invention, all of the moving magnetism method of using a gyromagnetic machine to stimulate the acupuncture points, the combination of magnetism and traditional acupoint workpieces to form the magnetic Di needle, the magnetic round plum needle, the photomagnetic method of combining magnetism with helium-neon laser irradiation, and the magnetoelectric method combining with the electroacupuncture therapy, all of which have been applied to nearly 70 diseases in various departments including internal, external, women, children, ophthalmology, otolaryngology and oral cavity, all of them have the aforementioned qualitative and quantitative problems. Therefore, if we want to standardize or normalize magnetic appliances, there comes the dilemma that the discussed foregoing variables are unpredictable and impossible to cope with. The root of accurate qualitativeness and quantitiveness lies in the precise positioning of the acupuncture points. When the precise acupuncture points are secured, for example, the pulse current applied to the magnetic sheet of the acupoint electrode, or the intensity of the magnetic field of the magnetic head of the electromagnetic thermal needle placed on the intradermal needle (or ordinary needle), or the intensity of the magnetic field applied to the magnetic needle, upon qi-obtainment after the needle is pierced, can all be precisely regulated. So far, the most important core spirit of the present invention has emerged, that is, to assist, check or confirm the patient's accurate acupoints with scientific methods or equipment during the doctor's diagnosis and treatment.

Through the foregoing discussions, we can summarize as follows: In the intrusive case, a wrong or deviant acupuncture of no medical effect may just make people feel disgusting. If side effects or other injuries occur, it is indeed unfortunate; in the non-intrusive case, a biased or wrong acupoint selection will cause qualitative, e.g. effective or not, or what kind of effect, and quantitative, e.g. how much irradiation or magnetic field strength is to be applied, difficulties, as mentioned above.

Most of the above are based on researches from Taiwan and the Mainland China, and here is a brief description of how foreigners view the acupuncture. In 1950, a German, Dr. REINHOLD VOLL discovered that there are different potential differences in the human body. After experimental studies, it was found that the "change" circuit diagram of the human body's "electricity" is exactly the same as the "Meridian Diagram" in "Ancient China." In 1949, after Dr. Yoshio Nakatani, a professor at Kyoto University in Japan, began to study the relationship between skin resistance and disease symptoms, he found that it was consistent with traditional Chinese meridians, and developed a set of "scientific" disease detection methods, referred to as "good conduction meridian". Recently, the "Federal Committee of German Doctors and Health Insurance" launched large-scale and high-standard human trials on headache, back pain and arthritis pain, and successively published that acupuncture does have an analgesic effect. However, because the sham control group with acupuncture at non-acupoint sites or insufficient needle penetration has similar analgesic effects to the real treatment group, it is suspected that the acupuncture itself may have a strong placebo effect and has nothing to do with acupuncture points. A few years ago, Dr. Edzard Ernst and graduate students in the United Kingdom designed a retractable needle. When inserted, the needle tip retracts into the needle tube and does not enter the skin, but it can make the subject think that there is a needle inserted (while the needle tube keep staying on the skin). That is, by using real and fake needles to conduct grouped randomized trials, the team of physicians found that fake acupuncture is as effective as real acupuncture in treating headaches and nausea and in preventing migraine. There is no anatomical basis for qi veins or acupuncture points, but American studies have found that acupuncture points are usually located at where the "connective tissue" is most dense. In 2002, Dr. Langevin from the University of Vermont in the United States published a study on The Anatomical Record, which showed that acupuncture and moxibustion on acupoints can have medical effects on the body. Western studies have shown that acupuncture and moxibustion can indeed relieve pain. The theory proposed is that the acupuncture stimulates the body to release endorphins. It also seems to increase the brain secretion of the chemical component serotonin (which can enhance the function of vasoconstriction), which changes the function of nerve cells, by which people feel "happiness and comfort". If it is non-intrusive, stimulating acupuncture points with different frequencies or energy levels will relax nerves and muscles and make them beat, which is like passive exercise, and can improve local blood circulation.

After the aforementioned close comparisons and discussions with conventional technologies, the goals or endeavors of the present invention should have been specifically presented. In fact, however, the above disclosure is only the basic level of what the present invention is attempted to arrive at, that is, the present invention actually has a higher level of goal pursuit. In the Huangdi (Yellow Emperor) Neijing Suwen, Ci-Yao Chapter, it is recorded "The Huangdi askes: I would like to know the gist of acupuncture. Qi Bo replied: There are grave and light diseases, while the acupuncture depth has shallow and deep. Each case has its own curing rationale, from which deviation should be avoided. An excessive depth will cause an internal hurt while an insufficiency will produce a superficial qi block which in turn invokes evil qi. An improper depth will cause a big trouble internally hurting the 5 organs to develop a serious disease." Specifically, acupuncture or a specific case must be dealt with a specific depth in order not to incur the big trouble. As we cannot have an insufficient depth or improper depth in order not to invoke a big trouble or a serious disease, we need to detect or ensure the relative position between the needle and the acupoint for an intrusive needle. Likewise, for anon-intrusive therapy, if we can really detect or ensure the relative position of the acupuncture workpiece and the acupoint, we can confidently determine for a specific disease or physical therapy, what degree of the irradiation or electric field or intensity of the magnetic field should be accurately applied, thus ensuring the desired therapeutic effects without suffering from negative effects.

In the Huangdi Neijing Suwen, Zhiyao Chapter, it is recorded that through the impermanence of birth, aging, sickness and death, each person suffers from a specific disease under a special cause. "Therefore, there are diseases in the epidermis, in the derma, in the adipose tissue, in the muscle, in the vein, in the sinew, in the bone, and in the marrow." How a misdiagnosis or wrong treatment will result in has been briefly seen in the preceding paragraph. In Huangdi Neijing Suwen, Zhiyao Chapter, it takes the disease in the derma or adipose tissue as an example. If one can't grasp the essentials in depth, one should be cautious that "when we are to acupuncture the derma or adipose tissue, there should be no subcutaneous layer piercing, because such piercing will indirectly damage the lungs, which in turn will incur warm malaria in autumn to be shuddering."

So far, the basic level of the present invention is to ensure the precise positioning between a patient or user's acupuncture point and the instrument, acupoint workpiece (non-intrusive) or an acupuncture device (intrusive) to guarantee that the acupuncture needle or workpiece has a correct or safe physical therapy or treatment. This goal, in a sense, is focused on the two-dimensional level, that is, how to solve or accurately position a patient or a user's acupoint with respect to the instrument, acupoint workpiece (non-intrusive) or a needle device (intrusive). As mentioned in the preceding paragraph, after ensuring the relative positional relationship, the pursuit of physical therapy or true needs of dealing with a specific disease can then be satisfactorily met through properly adjusting the parameters or variables involved in the third dimension (i.e. depth) and fourth dimension (i.e. angle). The present invention is not satiated through realizing the above two levels (basically belonging to the hardware). The Yellow Emperor Neijing Suwen, Yijing Qi-Change Chapter stated that in ancient times, the treatment of diseases was dealt with at the initial burgeoning of a disease, so the disease is difficult to adversely develop.

According to the Yellow Emperor Neijing Suwen, as the time goes by, "in the medieval ancient time, the disease was cured only when it has been developed, by being served with a medicinal soup for ten days to eliminate any one of the eight-wind and five-paralysis diseases. If not cured in ten days, herbal roots and the grass are used, by which the root and the symptom of the disease are both attended to get rid of the evil qi." As the human beings are born to chase fame and wealth in the economic world, they need to neglect or could not discern omens of disease until the disease has taken shape before they begin to think about treatment. At this time, it is necessary to rely on diet therapy or herbal medicine to eliminate the evil qi or drive away the disease. As for the human beings in the near ancient time, "the same is not true for the treatment of diseases. The treatment is not based on four seasons, ignores the sun and the moon, does not judge whether to combat or to follow the development, and is practiced after the disease is already established, by using the acupuncture from the outside and serving the medicinal soup into the body. An inferior artisan is aggressive enough to embark measures to attack the disease. It is not seldom to find out that while the disease is still there, a new disease emerges." In modern treatments, the same disease (for example, a cold) has almost the same medicine. It does not care about personal physique, and may not believe in the relationship between the disease condition and the four seasons or yin and yang. There is no idea to predict when or what disease should be treated with the development trend or against the development trend. Accordingly, it is not seldom experienced that although the symptoms have been eliminated, because the "root" of the disease has not been cured, the bud of a new disease latent in the body is waiting for an opportunity to burgeon and then prosper.

It is a further level of ideal of the present invention to focus on the level of "software", which can adapt or adjust the body immediately when there is an initial omen of a disease so that the ideal in the Yellow Emperor Neijing Suwen, Yijing Qi-Change Chapter "keeping near to the health but away from death, along the prolonged path of life" can be realized.

The ultimate level of the ideal of the present invention is to seek the health and happiness of all mankind, and to realize the ideal that may be moving in the preceding paragraph, so that every family or every person can have the software and hardware of the present invention even if their financial resources are relatively limited. When the present invention starts to be commercialized and becomes more advanced, every one may enjoy or receive physiotherapy or medical services like those provided by the reincarnation of Hua Tuo and Bian Que.

Other features and advantages of the present application are described later, and can be apparent in the specification, or can be understood by practicing the present application. The purpose and other advantages of the present application can be realized and obtained by the structure specifically pointed out in the specification and the drawings.

BRIEF DESCRIPTION OF THE DRAWINGS

The following drawings are drawn according to embodiments and are merely illustrative of the concepts of the present invention.

Figure 1:
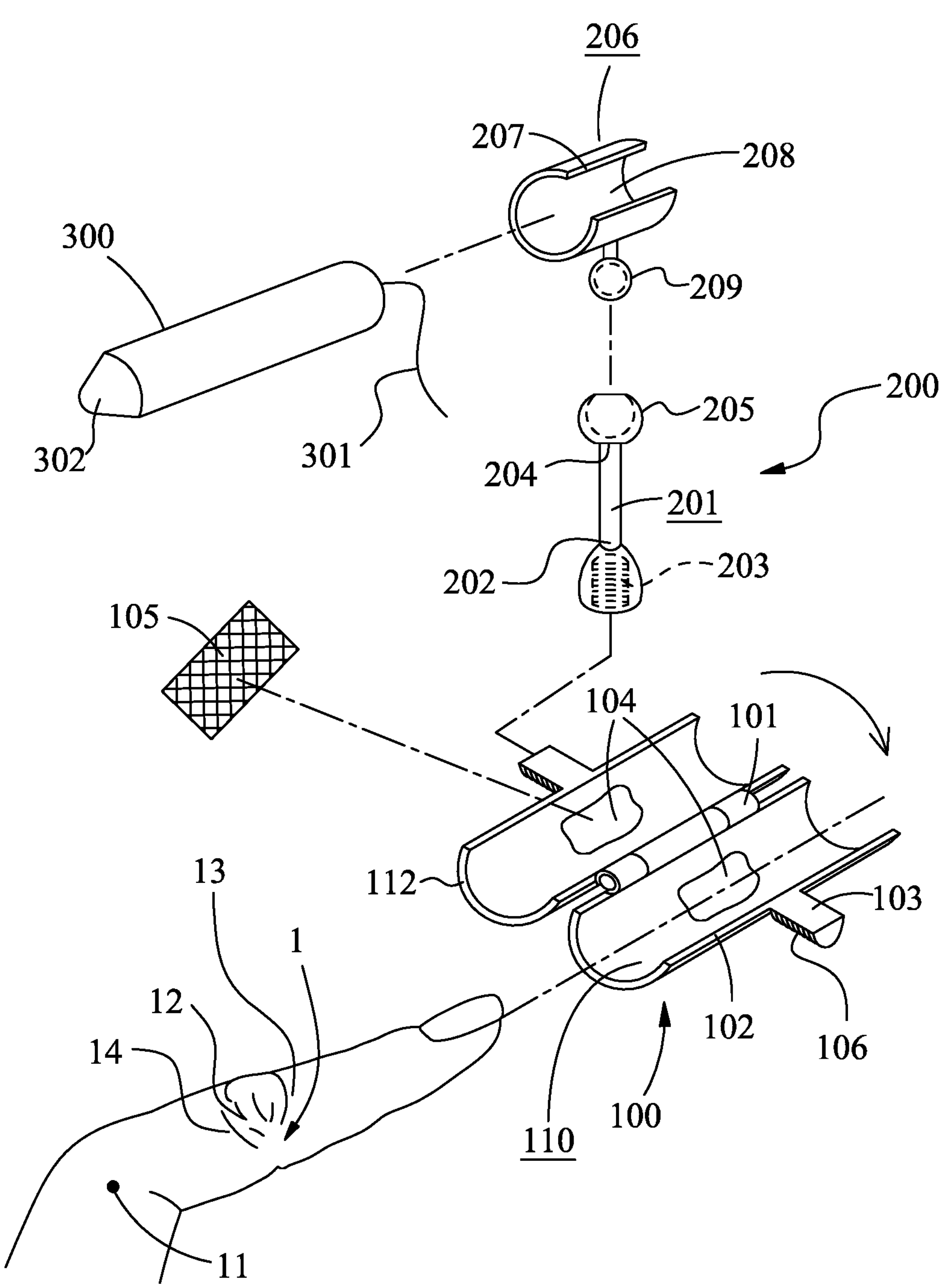
FIG. 1 is a health care device for positioning fingers or toes.

The reference numbers are:

1: index finger
2: fist
11: Erjian acupoint
12: finger joint
13: proximal end of middle phalanx of index finger
14: distal end of proximal phalanx of index finger
21: thumb
22: index finger
24: thumb joint
23: Hegu acupoint
25: second joint of index finger
26: short thumb muscle
30: Governor Vessel
31: Foot-Taiyang Meridian
32: Dazhui acupoint
33: Taodao acupoint
34: Shenzhu acupoint
35: Ganshu acupoint

36: Danshu acupoint
37: Pishu acupoint
38: Weicang acupoint
39: Huangmen acupoint
40: Zhishi acupoint
100: health care device
101: pivot part
102: fixing body
103: semicylindrical rod body
104: recess
105: soft layer of cloth
106: semicylindrical male thread
110, 110': health care body
112: hollow cylindrical end part
120: health care device
122: health care body
124: upper end shoulder
126: abutting plate
128: spring
130: groove
131: index finger plate
132: index finger accommodating area
133: shoulder
134: spring
135: index finger accommodating groove
136: abutting plate
138: index finger slot
140: middle finger slot
142: ring finger slot
144: little finger slot
146: recess
150: health care device
152: health care body
154: pressing piece
156: transverse piece
157: upper end
158: work piece support medium
160: sleeve
162: work piece connector
164: end
166: stanchion
168: intermediate connecting piece
170: health care device
172: health care body
174: first pair of stanchions
175: upper end
176: intermediate connecting piece
178: matching part
182: hole
184: second pair of stanchions
185: intermediate connecting piece
186: matching part
187: pivot
180, 188: thickness-halved area
189: clamp
190: protrusion
191: pin
192: clamp
193, 195: surface
194: flange
197: groove
196, 198: through hole
199: pin
200, 200': fixing piece
201: rod body
202: first end
203: female thread
204, 204': second end
205: universal ball joint seat
206: acupoint work piece connector
209: universal ball joint
300, 300': acupoint work piece
301: conducting wire
302, 302': acupoint work head
400: support transverse piece
401, 403: surface
402: connecting end
404: work piece support medium
405, 407: surface
406: adjustment sleeve
408: work piece connector
410: end
412: free end
500: health care device
501, 503: carrying base plate
502: health care body
505, 505': carpal protrusion of radius accommodating recess
506, 506': carpal protrusion of ulna accommodating recess
508: palm accommodating groove
510: cavity of positioning block
511, 512: paired recesses
504, 524: paired positioning blocks
513, 515: two ends of spring
514: plural springs
516: pair of lower lugs
517: inner wall of recess
518: pair of side grooves
519: inner wall of positioning block
520: recess of end of carrying base plate
526: recess
528: groove
530: lug
532: groove
534: recess
535: distal side of elbow end
536: groove
538: inner recess of adjacent ends of carrying base plates
540: tension spring
542: pin hole
544: pin
546: length adjustment medium
547: linking plate
548: pin hole
550: central groove of adjacent ends of carrying base plates
552: bottom cutout
554: bottom shaft hole
560: upper arm carrying base plate
562, 564: two carrier plates
566: axillary end
568: upper cutout
570: cutout
572: central pivot
574: length adjustment device
578: guiding sheet
580: cutout
582, 584: carrying base plate
586: length adjustment device of health care body
587: screw hole
588: rotatable screw rod
590: handle
591: longitudinal central groove

592: chain
594: positioning pin
595: sliding hole
596: length adjustment plate
597: distal groove
598: positioning pinhole
599: groove
600: trapezoidal piece
601: middle groove
602: side piece
603: two side bevels
604: spring
606: arc convex
608: groove
610: proximal groove
612: spring
614: guiding piece
616: sliding hole
618: guiding groove
620: trapezoidal piece and screw rod assembly
622: screw rod end
624: bottom hole
628: trapezoidal piece and screw rod assembly
630: trapezoidal piece
631: side bevel
632: shallow guiding groove
634: chuck
636: hole
638: screw rod
640: screw rod end
660: health care body
662: shank carrying base plate
664: thigh carrying base plate
666: (tibia) heel end of shank carrying base plate
668: side groove
670: recess
672, 674, 676: recess
678: slot
680: positioning block
681: opposite surface
682: lug
684: large lateral malleolus recess
686: middle lateral malleolus recess
685, 687, 689: malleolus recess
688: small lateral malleolus recess
690: length adjustment device
692: thread
694: operating rod
696: handle
698: chain
700: pin
702: carrying base plate of length adjustment device
704: screw hole
706: space between the thigh and shank carrying base plates
710: rod
712: rod hole
708: spring
714: positioning block
716: lug
718: recess
719: accommodating recess of knee tuberosity of the femur
720: central recess
722: through hole
724: pinhole
726: positioning block
728: positioning hole
730: (femur) buttock end of thigh carrying base plate
732: accommodating hole
734: spring
736: recess
738: stop
740: central concave
742: length adjustment trapezoidal piece
744, 746: two side bevels of trapezoidal piece
748: heel height adjustment medium
X and Y: distances between two side bevels and the center of operating rod
760: head health care body
762: base plate
764: slot
766: head positioning plate
768, 770: connecting rod
772: oil cylinder
774, 776: first end and second end of oil cylinder
778: ear hole
780: inverted triangular hole
782: lower protruding slider
784: pressure sensor
786, 788: oil cylinder forward and backward buttons
790: circuit configuration
800: head health care device
802: health care body
804: rail body
806: gear slot
808: lower gear rack
810: upper surface
812: upper gear rack
814, 816: carrier body
818: paired positioning plate
820: positioning gear
822: stepping motor
824: gear protection sheet
826: motor shaft
828: gear
830: left end surface of carrier body
832: positioning rod
834: paired positioning slot
836: side positioning plate
838: stepping motor
840: screw rod
842: screw rod nest
844: two side wall upper surfaces
846: moving piece
848: work base
850: fixing screw bolt
852: middle protruding piece
854: groove
856: ball
858, 860: upper surface of carrier body
862, 864: proximal surface of carrier body
870: acupoint work piece connecting piece
874: first end
876: fixing nut
878: internal thread
880: second end
882: acupoint work piece nut
884: internal thread
900: work base
902: longitudinal through hole
904: C-clamp
906: work piece holder
908: first end of work piece holder

910: second end of work piece holder
912: connector
914: internal thread
916: annular groove
918: first end of work piece
920: connecting piece
922: second end of work piece
930: work piece holder
932: threaded section
934: annular groove
936: work base
938: threaded hole
940: acupoint work piece
942: slender pneumatic cylinder
944: threaded end
946: piston rod of pneumatic cylinder
948: upper connecting ring
950: main connecting piece
952: ring piece
954: crankshaft
956: work ring
958: rubber pad
960: work end
962: work bottom
964: work piece
966: point opening
968: first end of main connecting piece
970: second end of main connecting piece
971: work base
972: angle controller
974: angle control assembly
976: work piece supporter
978: fixing piece
980: threaded barrel
982: work piece supporter
984: acupoint workpiece jaw
986: screw
988: holding part
1000: work piece assembly matched with robotic arm
1002: electric chuck
1004: jaw
1006: holding surface
1008: rotating head
1010: extension base
1012: first end
1014: connecting base
1016: rotating shaft
1018: rotating platform
1020: work platform
1022: work base
1024: first end
1026: second end
1028: second end
1030: first end
1032: second end
1040: automatic needle inserting acupoint work piece
1042: rotating head
1044: automatic needle inserting device
1046: needle inserting mechanism
1048: electric holder
1100, 1110, 1120: steps of first embodiment of health care method
1130-1180: steps of second embodiment of health care method
1200: health care system
1210: health care body
1215: micro computer
1220: central processing unit
1230: memory
1240: symptom treatment module
1250: personal health care history record module
1260: feedback/report module
1270: screen
1280: keyboard and/or mouse
1290: microphone
1300: lens
1400: cloud database
1500: service center
1600: control module

DETAILED DESCRIPTION

What follow will cooperate with the drawings to disclose how to realize the ideal of each level/each observation/each aspect of the present invention one by one. The following specific embodiments are specific examples used to assist in understanding a certain invention level/observation/solution, and are not the only feasible way or answer of the invention level/observation/solution. In fact, the descriptions of the specific embodiments of different invention levels/observation/solutions can be mutually referred to for replacement or modification. The present inventions should be groundbreaking, but the so-called groundbreaking inventions are only clever, organic or amazing new combinations of various components that are easily available in the world to realize the groundbreaking ideals. Specifically, the creation or advancement of the present invention generally does not lie in each component itself, but in the unexpected or creative combination of related components.

Please refer to FIG. 1 showing the first embodiment of the present invention in the basic level, where the Erjian acupoint 11 (International Code LI2) on the index finger 1 is taken as an example. Acupoint 11 is located between the red and white fleshes at the end of the radial transverse crease of proximal phalanx bone (the third segment) of the index finger, and mainly treats sore throat, toothache, epistaxis, crooked mouth and eye, lethargy, and shoulder/back pain. The health care device 100 includes a health care body 110 having two pieces of hollow semicylindrical fixing bodies 102 pivotally interconnected through the pivot part 101, each of which has a solid semicylindrical rod body 103 having a semicylindrical male thread 106. Each fixing body 102 has a recess 104 accommodating a finger joint 12, for example, the middle (second) and proximal (third) phalangeal joint. A cleanable or disinfectable soft layer of cloth or disposable paper 105 can be folded multiple times according to the user's fatness or finger thickness, so that when two fixing bodies 102 are tightly closed, index finger 1 or joint 12 determines or fixes the positional relationship between health care device 100 and index finger 1 or Erjian acupoint 11 (in this example) to obtain the previously described or expected effects. When two fixing bodies 102 are tightly closed, two semicylindrical rod bodies 103 constitute a complete bolt; and the protruding parts of the proximal end 13 of the middle phalanx and the distal end of the proximal phalanx 14 of index finger 1 are accommodated in recess 104.

A fixing piece 200 has a rod body 201 for providing a distance or height required for configuring or operating an acupoint work piece 300, where rod body 201 has a first end 202. After a female thread 203 in first end 202 engages with male thread 106 on two semicylindrical rod bodies 103, rod body 201 is fixed on health care device 100, while two semicylindrical fixing bodies 102 fix index finger 1 therein by locking first end 202 with two semicylindrical rod bodies 103. Rod body 201 has a second end 204 configuring a universal joint seat 205 thereon for connecting with a universal ball joint 209 on an acupoint work piece connector 206. Due to technological advancement, the rotational angle of the modern universal joint is extremely large, and it can withstand a considerable impact at a specific angle and/or position without being out of position. Moreover, if one universal joint is not enough, multiple universal joints can be serially connected to enhance the extent of the desired orientation.

Acupoint work piece connector 206 has two lips 207 for passing and holding acupoint work piece 300 in a hollow space 208 thereof. Acupoint work piece 300 can be an energy work unit of microwave, laser or radiation as aforementioned, and has a conducting wire 301 for receiving electrical energy supply, so as to output energy from an acupoint work head 302. Due to the configuration of connector 206 and fixing piece 200, a work energy releasing unit can thus be in the form of acupoint work piece 300, at which the work energy output is concentrated. Because a relative position of between acupoint work piece 300 and acupoint 11 has thus been determined, how or to what extent an acupoint work head 302 of acupoint work piece 300 can or should output the energy can also be precisely controlled or adjusted according to the specific requirement of the user/patient.

Additionally, the bulks of health care device 100, fixing piece 200 and acupoint work piece 300 are relatively limited. As long as conducting wire 301 is long enough, the user can either ideally move his position, or act at will without changing the relative position between acupoint work piece 300 and Erjian acupoint 11, thereby not affecting the expected physiotherapy/treatment effect. Furthermore, there are various ways for connection between acupoint work piece connector 206 and acupoint work piece 300, or between first end 202 and semicylindrical rod body 103. For example, one is provided with an annular protrusion and the other matching piece is provided with an annular groove, so as to make the assembly between first end 202 and semicylindrical rod body 103 easier. Therefore, we can easily understand that the description for this figure or the embodiment is only an example for realizing the objects disclosed in the present invention.

The first embodiment of the present invention is summarized as follows: health care device 100 includes health care body 110 for positioning body part 1 of a user, so as to maintain a first specific positional relationship with body part 1, wherein body part 1 has acupoint 11; acupoint work piece 300 for performing a health care work on acupoint 11; and work piece holder 200 having first end 202 connected to health care body 110 and second end 204 for fixing acupoint work piece 300, so that under the first specific positional relationship, acupoint work piece 300 performs the health care work under the condition that acupoint work piece 300 has a second specific positional relationship with acupoint 11.

In accordance with health care device 100 of the first embodiment, acupoint work piece 300 has acupoint work head 302, and the second specific positional relationship refers to a positional relationship between acupoint 11 and acupoint work head 302.

In accordance with health care device 100 of the first embodiment, health care body 110 is to relatively position a finger, toe, arm or leg of the user.

In accordance with health care device 100 of the first embodiment, health care body 110 is formed by two mutually pivoted fixing bodies 102 of a hollow semicylindrical cross section, each of which has a semicylindrical rod body 103, and two semicylindrical rod bodies 103 are combinable into a connecting rod.

In accordance with health care device 100 of the first embodiment, each semicylindrical fixing body 102 has inner recess 104 to accommodate the body part or the joint of finger 1, so that health care body 110 can properly fit or relatively position body part 1.

In accordance with health care device 100 of the first embodiment, the fixing piece 200 has a first end 202 being hollow for accommodating the connecting rod piece formed by the two semicircular section rod bodies 103, and thus, the two hollow semicircular section fixing bodies 102 closely fit the body part 1 therein.

In accordance with health care device 100 of the first embodiment, fixing piece 200 has second end 204 fixed to acupoint work piece connector 206 connecting acupoint work piece 300, through a fixing medium which can be one or more serially connected universal joints.

In accordance with health care device 100 of the first embodiment, the connection method between first end 202 of fixing piece 200 and two semicylindrical rod bodies 103 for forming the connecting rod piece, or between acupoint work piece connector 206 and acupoint work piece 300 can be male and female threads, an elastic holding, or an engagement of annular convex and annular concave through the material characteristics.

From another aspect, the aforementioned embodiment discloses health care device 100 including health care body 110 for fixing body part 1 of a user, so as to maintain a first specific positional relationship with body part 1; and work piece holder 200 having first end 202 connected to health care body 110, and second end 204 fixing acupoint work piece 300, and ensuring acupoint work piece 300 to perform the health care work under the condition that acupoint work piece 300 has a second specific positional relationship with acupoint 11 under the first specific positional relationship.

From yet another aspect, the aforementioned embodiment discloses health care device 100 for holding acupoint work piece 300 thereon to engage in a health care work onto a user, wherein the user has a body part having acupoint 11, and health care device 100 includes health care body 110 for relatively positioning body part 1 so that health care body 110 and body part 1 maintain a first specific positional relationship therebetween, and work piece holder 200 having first end 202 configured on health care body 110 and second end 204 for holding acupoint work piece 300, and ensuring acupoint work piece 300 to perform the health care work under the condition that acupoint work piece 300 has a second specific positional relationship with acupoint 11 under the first specific positional relationship.

Figure 2:
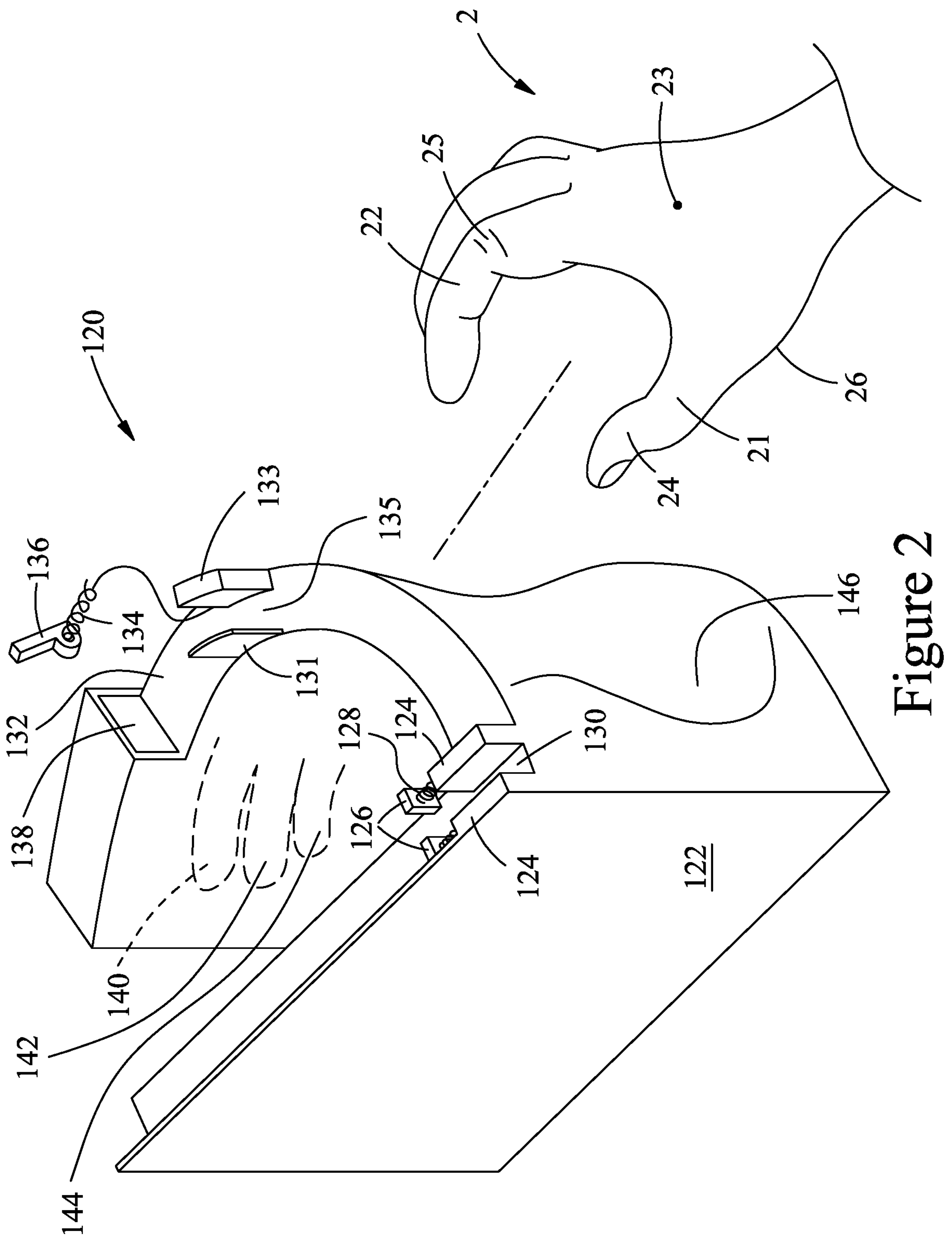
FIG. 2 is a health care device fixed on two different parts of the body part.

Referring to FIG. 2 showing the second embodiment of the present invention of a basic level, the Hegu acupoint 23 (International Code LI4) located between the thumb 21 and the index finger 22 on the fist 2 is taken as an example. Acupoint 23 is located between the first and the second metacarpal bones, but is slightly closed to the midpoint of the second metacarpal bone, and mainly treats headache, eye pain, sore throat, toothache, epistaxis, cold, stroke, and facial paralysis. The same as the first embodiment, this embodiment is focused on acupoints of special situation. When it is possible to overcome the difficulty of positioning a special acupoint with respect to an acupoint work piece (or its acupoint work head), the problems related to acupoints that are more common or easier to obtain the relative positions can be easily solved.

Health care device 120 includes a health care body 122 being generally semi-cylindrical and having a groove 130 for accommodating a user's thumb 21 therein. The user's thumb joint 24 is sleeved with health care body 110 of the first embodiment having a hollow cylindrical end part 112 having two sides rested on two abutting plates 126 configured on two upper end shoulders 124 of health care body 122. Two abutting plates 126 are pushed toward the thumb tip by two springs 128 respectively. Thereby, the relative position between thumb 21 and health care body 122 is secured.

Health care body 122 has a recess 146 for fitting the short thumb muscle 26 of a user, for the user's feeling of gripping health care body 122. Another health care body 110' is sleeved on the second joint 25 of index finger 22. Health care body 110 and health care body 110' can be the same (where thumb 21 or index finger 22 is properly fit by cloth soft layer 105 of the first embodiment) or different (where their outlines or sizes slightly vary with thumb 21 and index finger 22 respectively). After second joint 25 is sleeved in health care body 110', index finger 22 sleeved on health care body 110' rests in the index finger accommodating area 132 through the index finger accommodating groove 135 configured between the index finger wall 131 and the shoulder 133, while the right and upper sides of the hollow cylindrical end part 112' of health care body 110' urge against the abutting plate 136 connected to the connecting spring 134. Abutting plate 136 here is generally inverted L-shaped, with its horizontal part and vertical part respectively urging against the right and upper sides of hollow cylindrical end part 112' of health care body 110' in FIG. 2. Further, the horizontal part of inverted L-shaped abutting plate 136 pivots thereon spring 134, so that after index finger 22 is positioned properly, the vertical part of inverted L-shaped abutting plate 136 is rotated to urge against the upper side of hollow cylindrical end part 112'. By this, on the one hand, index finger 22 is constrained to be positioned, and on the other hand, the relative positional relationship between the second end 204' of the fixing piece 200' and Hegu acupoint 23 is ensured accordingly. In other words, the relative positional relationship between the acupoint work head 302' on the acupoint work piece 300' and Hegu acupoint 23 is thus assured for the previously described or expected effects. Furthermore, health care body 122 is provided with an index finger slot 138 for insertion of index finger 22 placed in groove 132. Certainly, health care body 122 can be further provided with a middle finger slot 140, a ring finger slot 142 and a little finger slot 144 for optional insertion of the other three fingers. Each of finger slots 138-144 may or may not communicate with each other, or each has a completely or partially independent space for accommodating fingers individually or collectively.

It should be noted that health care body 110 and health care body 110' in this embodiment may have basic structural differences from health care body 110 in the first embodiment, because health care body 110 and health care body 110' in this embodiment need not self-position by thumb joint 24 as that in the first embodiment 110. In details, health care body 110' can only extend over the middle part of a phalanx because one end of health care body 110' will be stopped by the finger joint, so that health care body 110' will not slip off. Since the other end of health care body 110' will urge against abutting plate 126 or 136, there is no trouble with positional assurance. The axial length of health care body 110' may thus be shortened.

The second embodiment of the present invention is summarized as follows: health care device 120 includes health care body 122 having two accommodating grooves 130, 135 for relatively positioning two different parts 21, 22 of a user's body part 2 respectively, so as to maintain a first specific positional relationship with body part 2; and work piece holder 200 having first end 202 connected to the health care body 110', and second end 204 for fixing acupoint work piece 300', so that acupoint work piece 300' and body part 2' are in a second specific positional relationship under the first specific positional relationship.

In accordance with health care device 120 of the second embodiment, there is acupoint 23 between two different parts 21, 22, acupoint work piece 300' has an acupoint work head 302', and the second specific positional relationship refers to the positional relationship between acupoint 23 and the acupoint work head 302'.

In accordance with health care device 120 of the second embodiment, health care body 122 is used to relatively position the user's two fingers, such as thumb and index finger.

In accordance with health care device 120 of the second embodiment, health care body 122 has two finger accommodating parts, such as thumb accommodating groove 130 and index finger accommodating groove 135.

In accordance with health care device 120 of the second embodiment, thumb accommodating groove 130 is defined by two shoulders 124, two springs 128 respectively configured in two shoulders 124, and two abutting plates 126 respectively connected to springs 128.

In accordance with health care device 120 of the second embodiment, index finger accommodating area 132 includes index finger stopping plate 131, shoulder 133, groove 135 defined by index finger stopping plate 131 and shoulder 133, spring 134 configured in shoulder 133, and inverted L-shaped abutting plate 136 pivotally connected to spring 134.

In accordance with health care device 120 of the second embodiment, health care body 122 has recess 146 for fitting short thumb muscle 26, so that the user can have a feeling of gripping health care body 122.

In accordance with health care device 120 of the second embodiment, health care body 122 has index finger slot 138 for accommodating the distal section of index finger 22, and can have middle finger slot 140, ring finger slot 142, and little finger slot 144 for optional insertion of the other three fingers, wherein finger slots 138-144 may or may not communicate with each other, or each has a completely or partially independent space for accommodating fingers individually or collectively.

From another aspect, health care device 120 holds an acupoint work piece (as described in FIG. 1 or the following embodiments) thereon to engage in a health care onto a user, wherein the user has body part 2 having two different parts 21, 22, there is acupoint 23 between the two different parts, and health care device 120 includes: health care body 122 having two abutting parts (124-130 and 131-135) for positioning two different parts 21, 22 of body part 2, so as to maintain a first specific positional relationship with body part 2; and a work piece holder (as described in FIG. 1 or the following embodiments) having: a first end configured on the health care body; and a second end holding the acupoint work piece, for ensuring acupoint work piece 300 to perform the health care work when acupoint work piece 300 has a second specific positional relationship with acupoint 11 under the first specific positional relationship.

From yet another aspect, health care device 120 includes health care body 122 having two abutting parts (124-130 and 131-135) for relatively positioning two different parts 21, 22 of body part 2 of a user respectively, for maintaining a first specific positional relationship with body part 2, wherein there is acupoint 23 between two different parts 21, 22; and a work piece holder (as described in FIG. 1 or the following embodiments) has: a first end configured on the health care body; and a second end holding an acupoint work piece (as described in FIG. 1 or the following embodiments) thereon, for ensuring acupoint work piece 300 to perform a health care work under the condition that acupoint work piece 300 has a second specific positional relationship with acupoint 11 under the first specific positional relationship.

Figure 3A:
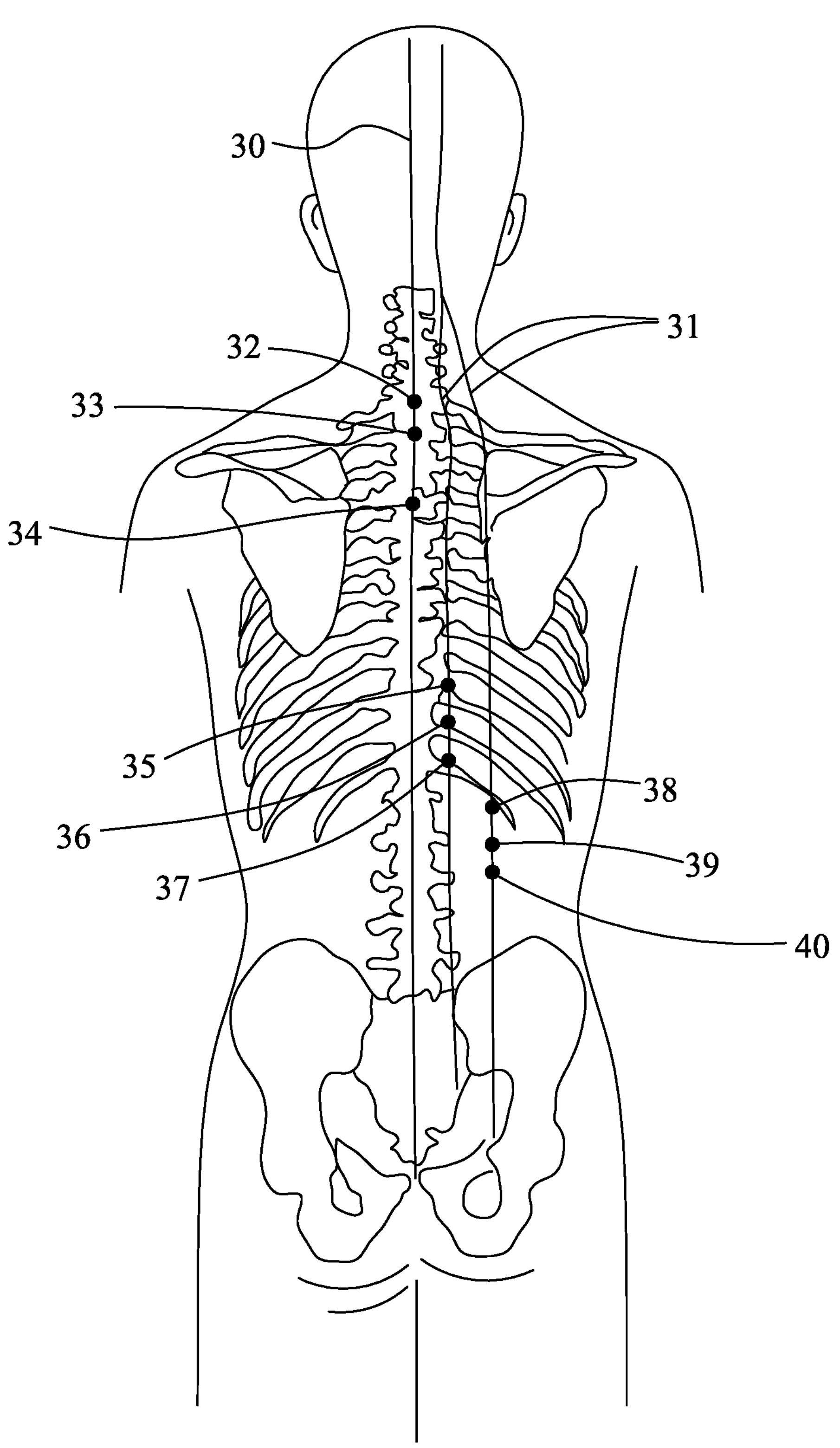
FIG. 3A is a schematic diagram of the meridians and acupoints on the back.

Distribution of acupoints in chest or abdomen of a human body is quite symmetrical. For the chest, the midline is the Conception Vessel with two Kidney Meridians of Foot-Shaoyin located 0.5 body inch away from two sides thereof, two Stomach Meridians of Foot-Yangming located another 1 body inch away (i.e. 1.5 body inches from the Conception Vessel), etc. For the back, the midline or spine is the Governor Vessel with two branches of two Bladder Meridians of Foot-Taiyang respectively located 1.5 and 3 body inches away from two sides thereof, etc. FIG. 3A shows Governor Vessel 30, Bladder Meridian 31 and acupoints, such as Dazhui acupoint (International Code GV14) 32, Taodao acupoint (International Code GV13) 33, Shenzhu acupoint (International Code GV12) 34, Ganshu acupoint (International Code BL18) 35, Danshu acupoint (International Code BL19) 36, Pishu acupoint (International Code BL20) 37, Weicang acupoint (International Code BL50) 38, Huangmen acupoint (International Code BL51) 39 and Zhishi acupoint (International Code BL52) 40.

Figure 3B:
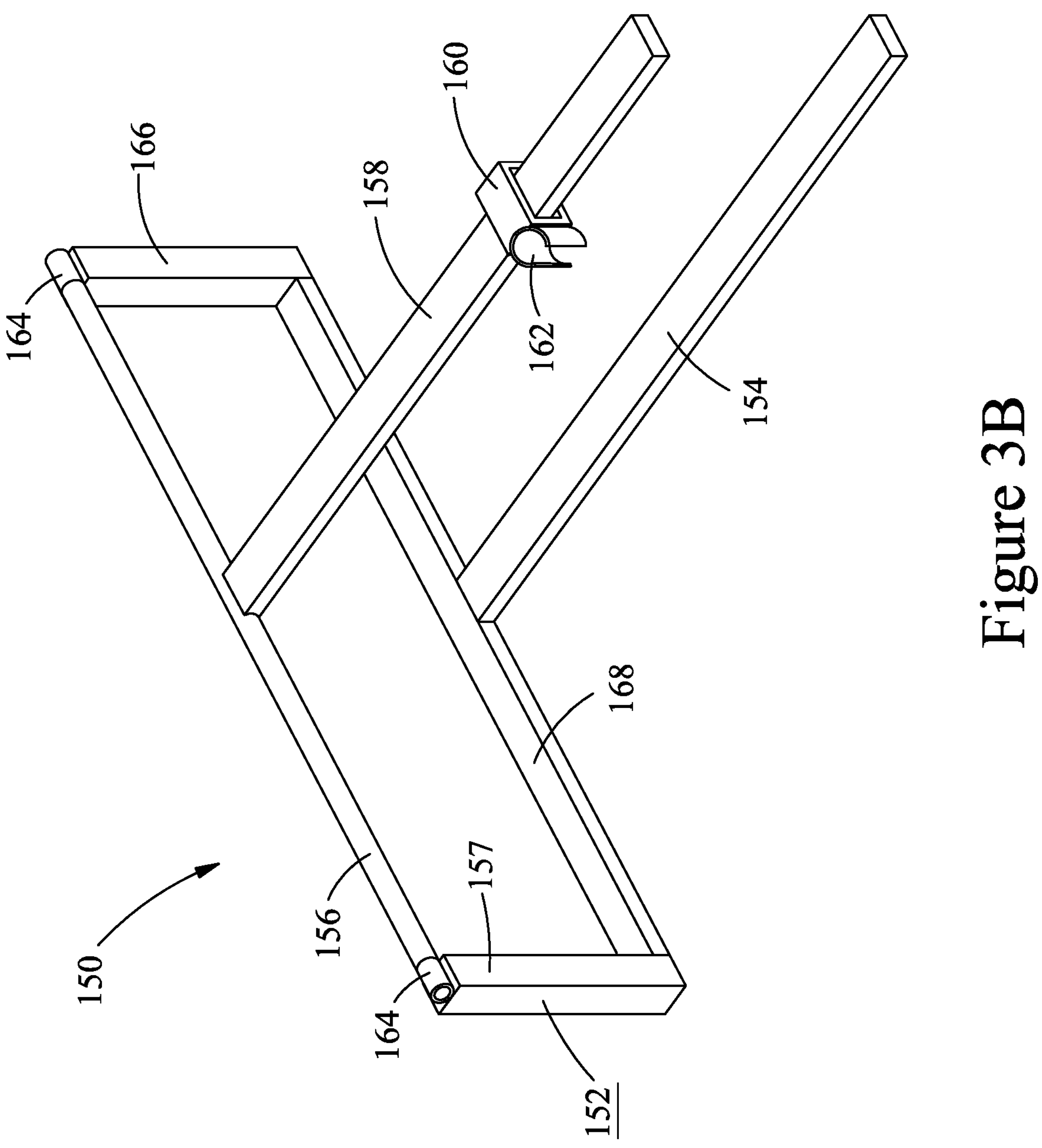
FIG. 3B is a simple health care device positioned with respect to the chest or back.

Please refer to FIG. 3B showing a simple health care device 150 for chest or back. Health care device 150 has health care body 152, support transverse piece 156 having two ends 164 connected to health care body 152, and work piece support medium 158 fixed on support transverse piece 156. Health care body 152 further has two stanchions 166 whose upper end 157 is pivoted on an end 164 of support transverse piece 156, intermediate connecting piece 168 fixed on two stanchions 166, and pressing piece 154 fixed on intermediate connecting piece 168, wherein angles included between two stanchions 166 and intermediate connecting piece 168, and between intermediate connecting piece 168 and pressing piece 154 are generally 90 degrees. That is, when using, the user presses pressing piece 154 with his/her chest or back to ensure health care body 152 to be in a definite relative positional state. Because pressing piece 154 is to be pressed by the user, its shape should not cause uncomfortableness to the user, or its placement surface should have corresponding recess to avoid the user's discomfort.

Work piece support medium 158 slidably sleeves thereon a sleeve 160 fixing thereon a work piece connector 162 for sleeving thereon an acupoint work piece as described in the first embodiment. Therefore, the physiotherapist or therapist can move/adjust the position of sleeve 160 on work piece support medium 158 to fix or secure the relative positional relationship between the acupoint work piece and the specific acupoint.

Figure 3C:
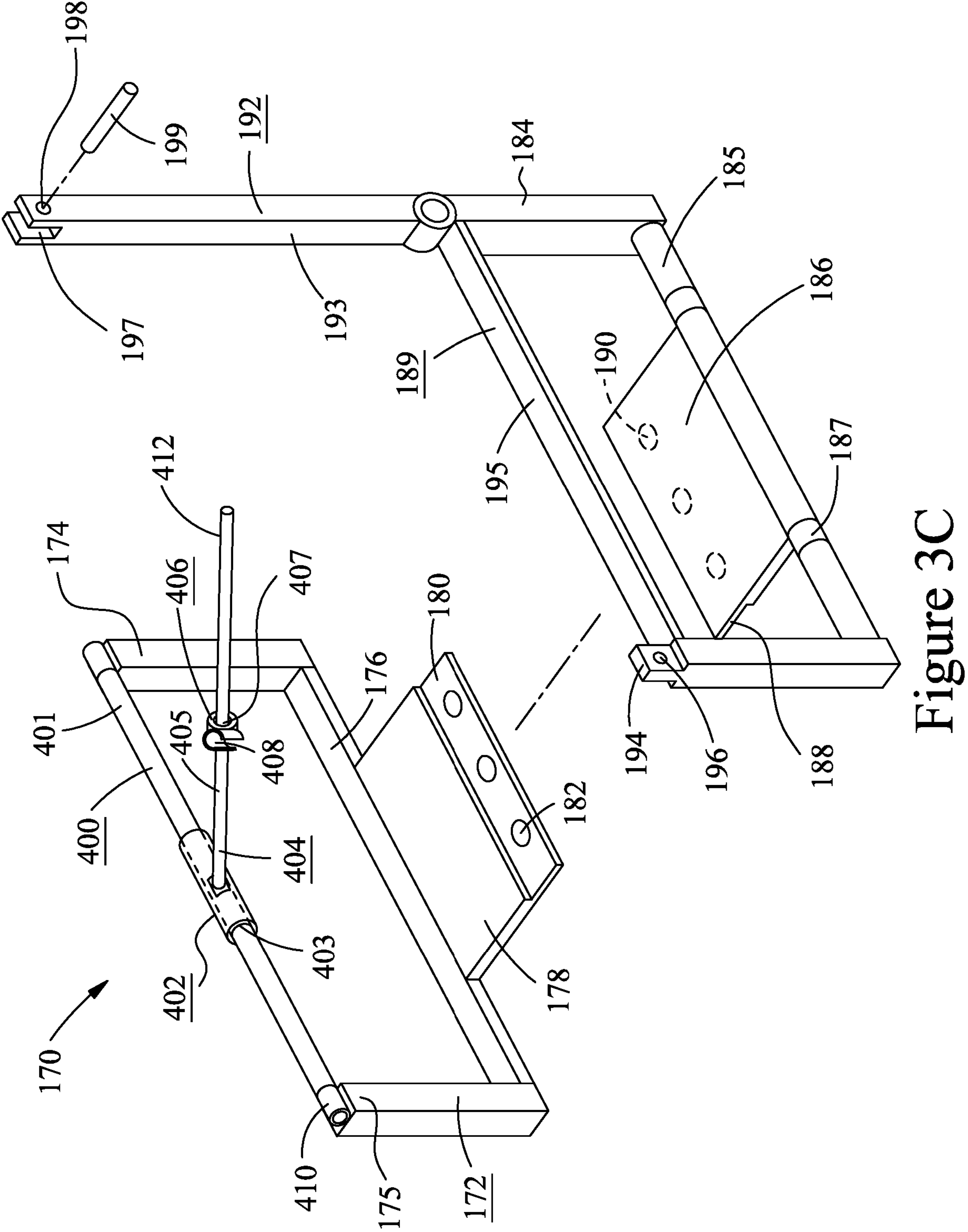
FIG. 3C is an advanced health care device positioned with respect to the chest or back.

There are so many acupoints in chest or back while health care device 150 seems too simple, so that we may agree that health care device 170 in FIG. 3C is somewhat advanced. Health care device 170 has health care body 172, support transverse piece 400 having two ends 410 pivoted on health care body 172 respectively, and work piece support medium 404 slidably sleeved on support transverse piece 400. Health care body 172 has a first pair of stanchions 174 whose upper end 175 is pivoted to an end of support transverse piece 400, intermediate connecting piece 176 fixed on two stanchions 174, matching part 178 fixed on intermediate connecting piece 176, a second pair of stanchions 184, intermediate connecting piece 185 fixed on two stanchions 184, and matching part 186 fixed on intermediate connecting piece 185, wherein angles included between two stanchions 174 (184) and intermediate connecting piece 176 (185), and between intermediate connecting pieces 176 (185) and matching parts 178 (186) are generally 90 degrees, and matching part 178 (186) has a thickness-halved area 180 (188), matching part 186 is pivoted on intermediate connecting piece 185 through pivot 187, and thickness-halved areas 180 and 188 respectively have matching holes 182 and protrusions 190. In use, matching part 186 and two stanchions 184 are first kept in parallel or coplanar, and after the user presses the combined matching parts 178 and 186 with his/her chest or back, two stanchions 184 are pivoted to have the right-angle relationship with matching part 186 for ensuring health care body 172 in a secured relative position. As mentioned above, because matching parts 178 and 186 are to be pressed by the user, their shapes should not cause uncomfortableness to the user, or their placement surface should have corresponding recesses to avoid the user's discomfort.

As in the preceding example, work piece support medium 404 slidably sleeves thereon sleeve 406 fixing thereon work piece connector 408 for sleeving thereon the acupoint work piece in the first embodiment. Therefore, the physiotherapist or therapist can move/adjust the position of sleeve 406 on work piece support medium 404 to fix or secure the relative positional relationship between the acupoint work piece and the specific acupoint. Work piece support medium 404 has connecting end 402 slidably sleeved on support transverse piece 400, and free end 412 clamped by a pair of clamps 189 and 192 on a second pair of stanchions 184, wherein clamp 189 is fixed above the pair of stanchions 184, clamp 192 is pivoted on the upper end of one stanchion 184 by pin 191, the other stanchion 184 has flange 194, the free end of clamp 192 has groove 197, flange 194 and the free end of clamp 192 respectively have through holes 196 and 198, and pin 199 passes through the through holes 196 and 198 so that the pair of clamps 189 and 192 hold free end 412.

Although precise fit is no longer a problem in nowadays technology, considering convenience of sliding (so a tolerance must be left) and security of positioning, corresponding surfaces 195 and 193 of clamps 189 and 192, corresponding surfaces 401 and 403 of support transverse piece 400 and connecting end 402, and corresponding surfaces 405 and 407 of work piece support medium 404 and adjustment sleeve 406 may be roughened or covered with a layer of thick or thin rubber material. Additionally, because acupoints in chest and abdominal are symmetrically distributed relative to the Conception Vessel or Governor Vessel, both symmetrical acupoints need physiotherapy/treatment, and adjustment sleeve 406 is thus preferably configured in pairs. Certainly, if multiple acupoints are simultaneously required to be treated, work piece support medium 404 can have an increased number.

Preceding two embodiments are summarized as follows: health care device 150 (170) includes health care body 152 (172) having two supporting pieces 166 (174), each of which has upper end 157 (175), so as to maintain a first specific positional relationship with a user's body; support transverse piece 156 (400) having two ends 164 (410) pivoted on upper ends 157 (175) of two supporting pieces respectively; and work piece support medium 404 having first end 402 connected to health care body 152 (172), and adjustment sleeve

406 sleeved thereon for fixing an acupoint work piece, so that the acupoint work piece and the body are in a second specific positional relationship under the first specific positional relationship.

In accordance with health care device 150 (170) of the embodiment, the body is chest or back of a human body, the acupoint work piece has an acupoint work head, and the second specific positional relationship refers to a relative positional relationship between a chest or back acupoint and the acupoint work piece.

In accordance with health care device 150 (170) of the embodiment, health care body 152 (172) has pressing piece 154 (178, 186) for being pressed by a user's chest or abdomen for securing the relative position between the users and health care body 152 (172).

In accordance with health care device 150 (170) of the embodiment, pressing piece 154 has two matching parts 178, 186, each of which has thickness-halved area 180 (188), and thickness-halved areas 180, 188 have matching holes and protrusions respectively.

In accordance with health care device 150 (170) of the embodiment, health care body 172 has two pairs of stanchions 174, 184, bottoms of each pair of stanchions 174, 184 are interconnected with intermediate connecting piece 176 (185), and matching part 186 is pivoted on intermediate connecting piece 185 by pivot 187.

In accordance with health care device 170 of the embodiment, work piece support medium 404 is slidably sleeved on support transverse piece 400; and/or work piece support medium 404 slidably sleeves thereon sleeve 406.

In accordance with health care device 170 of the embodiment, a second pair of stanchions 184 of health care body 172 has a pair of clamps 189, 192 configured thereon for holding free end 412 of work piece support medium 404.

In accordance with health care device 170 of the embodiment, corresponding surfaces 195 and 193 of clamps 189 and 192, corresponding surfaces 401 and 403 of support transverse piece 400 and connecting end 402, and corresponding surfaces 405 and 407 of work piece support medium 404 and adjustment sleeve 406 are roughened or covered with a layer of rubber material.

In accordance with health care device 170 of the embodiment, second adjustment sleeve 406, and/or second work piece support medium 404 are/is further included.

From another aspect, health care device 150 (170) holds an acupoint work piece (as described in FIG. 1 or the following embodiments) thereon to engage in a health care onto a user, wherein the user has a body part having an acupoint, and the health care device includes: health care body (152, 166, 154, 168; 172, 174, 178, 184, 190) having a pair of supporting pieces (152, 166; 172, 174; 184), for maintaining a first specific positional relationship with a user's body; support transverse piece 400 having two ends 410 respectively connected to the supporting pieces; and work piece support medium 404 connected to support transverse piece 400 and sleeving thereon sleeve 406 holding the acupoint work piece, for ensuring the acupoint work piece to perform the health care work when the acupoint work piece has a second specific positional relationship with the acupoint under the first specific positional relationship.

From yet another aspect, health care device 150 (170) includes health care body (152, 166, 154, 168; 172, 174, 178, 184, 190) having a pair of supporting pieces (152, 166; 172, 174; 184) for relatively positioning a user's body part to maintain a first specific positional relationship with the body part, wherein the body part has an acupoint; support transverse piece 400 having two ends 410 respectively connected to the pair of supporting pieces; and work piece support medium 404 connected to the support transverse piece and sleeving thereon sleeve 406 holding the acupoint work piece, for ensuring the acupoint work piece to perform the health care work when the acupoint work piece has a second specific positional relationship with the acupoint under the first specific positional relationship.

Figure 4A:
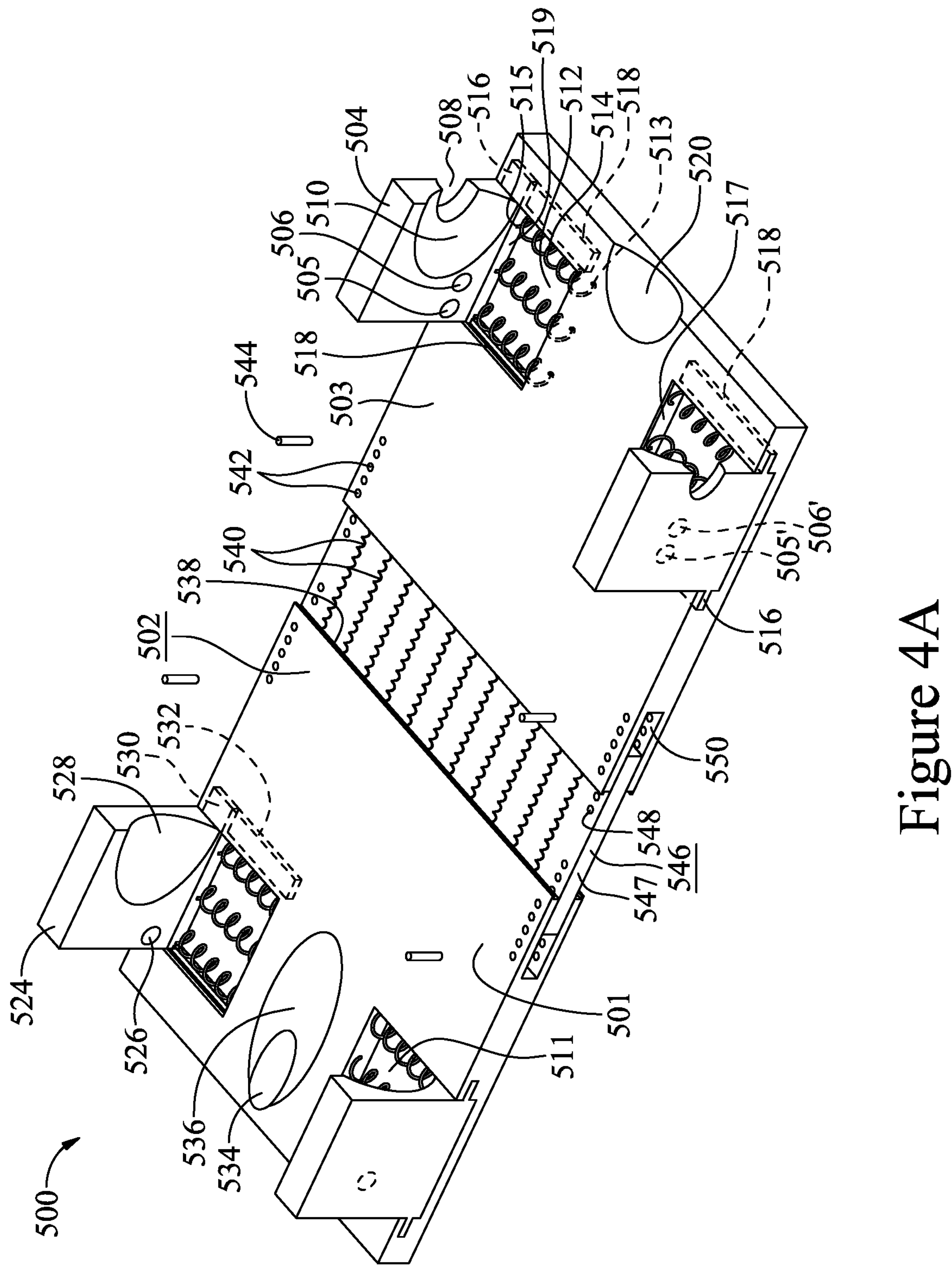
FIG. 4A is the health care body of the health care device for the lower arm.

The meridian path in either upper or lower arm is not regular or identifiable relatively easier like that (or acupoints) in chest or abdomen of the human body, runs either in yin or yang side of the arm. Contrasting to the acupuncturists who may identify it easily, it is not easy for the general public or beginners. We only deal with the positioning problem first. Please refer to FIG. 4A showing health care body 502 of upper arm health care device 500 of the present invention which has carrying base plates 501, 503, each of which has paired recesses 511, 512 respectively configuring pairs of positioning blocks 524, 504. Because all positioning blocks 524, 504 are similarly provided, only positioning block 504 is illustrated in details as follows.

Positioning block 504 has a pair of lower lugs 516 slidably configured in a pair of side grooves 518 in recess 512. Two ends 513, 515 of each of springs 514 are respectively configured on inner wall 517 of recess 512 and inner wall 519 of the lower part of positioning block 504. Inner wall 517 and inner wall 519 are provided to compensate or offset the length of springs 514. In this invention, plural springs 514 always keep paired positioning blocks 504 as close as possible to each other in paired recesses 512. The remaining width of the cutout upper portion at the free end of carrying base plate 503 between paired recesses 512 is approximately the thickness of the lower arm wrist. Because people are unavoidably thin or fat, according to this invention, paired positioning blocks 504 can be adjusted automatically to hold the wrist part. Additionally, the lug in the figure is sheet-shaped, while cylindrical one may be more common. Because they make no substantial difference, it will not be further described.

When acupoints of the Hand-Yangming Large Intestine Meridian (for example, Wenliu, International Code LI7, which mainly treats headache, sore throat, borborygmus, abdominal pain, and shoulder/back pain) are treated, the wrist should be held by paired positioning blocks 504 in the thickness direction to facilitate acupoint physiotherapy/treatment. At this time, the protrusion corresponding to the short abductor muscle of the user's thumb rests in cavity 510 recessed in positioning block 504. However, when acupoints of the Hand-Jueyin Pericardium Meridian (for example, Neiguan, International Code PC6, which mainly treats stomach pain, nausea, vomiting, chest pain, arrhythmia, stroke/dementia, elbow spasm, hot face, cloudy vision, shock) are treated, the wrist should be held by paired positioning blocks 504 in the width direction with the yin side up. At this time, a radial carpal protrusion of the lower arm abuts on recess 506 of left side positioning block 504, while an ulnar carpal protrusion of the lower arm abuts on recess 505' of right side positioning block 504 for co-performing the positioning effect. If we observe the wrist structure carefully, contrasting with the palm, the radial carpal protrusion of the lower arm is in a lower but anterior position, while the ulnar carpal protrusion is in an upper but posterior position, and thus we can use this structural feature to design positions of recesses 505, 506 of positioning block 504 for strengthening the positioning relationship or function. Specifically, no matter whether the yin side of the forearm (or lower arm) faces upward or downward, it can be effectively held by positioning blocks 504. Additionally, the user's palm stays free in groove 508 of positioning block 504.

On the contrary, when acupoints of the Hand-Shaoyang Sanjiao Meridian (for example, Waiguan, International Code TE5, which mainly treats unfavorable flexion and extension of elbow/arm, finger pain/inability to grip, hand tremor, deafness, tinnitus, headache, cheek pain, fever) are treated, the wrist should be held by paired positioning blocks 504 in the width direction with the yang side up. At this time, the ulnar carpal protrusion of the lower arm abuts on recess 505 of left side positioning block 504, while the radial carpal protrusion of the lower arm abuts on recess 506' of right side positioning block 504 for co-performing the positioning effect. There is a recess 520 at the end of carrying base plate 503. This recess 520 has two functions, wherein on the one hand, when the forearm side is kept laterally upright on base plate 503 (i.e., resting with thickness), the abductor muscle of the user's little finger rests thereon; on the other hand, when the yin side of the forearm is placed on base plate 503, the user's wrist/palm rest thereon.

Please refer to the left portion of FIG. 4A showing positioning block 524 and carrying base plate 501 for carrying the elbow joint. Positioning block 524 has recess 526 accommodating the most protruding sesamoid at the ulnar side of the elbow end of the humerus, and carrying base plate 501 correspondingly has recess 534 accommodating the most prominent part (i.e., elbow tip) of the elbow end of the ulna. The structure of the human body is very mysterious. When the forearm rests on carrying base plates 501, 503, whatever it is kept laterally upright or placed with the yang side, recesses 526 and 534 can accommodate the sesamoid and the most prominent part, respectively. However, when the forearm is kept laterally upright, left and lower sides of prominent muscles (composed of the palmar longus muscle, the flexor carpi radialis and the flexor carpi ulnaris) of the forearm are respectively positioned in groove 528 of positioning block 524 and groove 536 of carrying base plate 501. As preceding positioning block 504 of the wrist joint, positioning blocks 524 are configured on paired recesses 511 of carrying base plate 501, and has paired lugs 530 slidably configured in grooves 532 of recesses 511.

Please refer to the middle portion of FIG. 4A showing length adjustment medium 546 configurated between two carrying base plates 501, 503. The Creator is mysterious, and makes people either tall or short with arms either short or long. For example, it is said that Liu Bang's hands are long enough to extend beyond his knees, and thus length adjustment medium 546 is configured for accommodation. Adjacent ends of carrying base plates 501, 503 have central groove 550 for accommodating linking plate 547 symmetrically. Each adjacent end of carrying base plates 501, 503 has inner recesses 538, so that pairs of tension springs 540 are configured symmetrically above and below linking plate 547 to pull together carrying base plates 501, 503 as much as possible. Opposite sides of adjacent ends of carrying base plates 501, 503 respectively have plural pairs of pin holes 542, which correspond to plural pin holes 548 on both sides of linking plate 547. When the distance between adjacent ends of carrying base plates 501, 503 corresponding to the user's arm length is properly adjusted, four pins 544 can be inserted into corresponding pin holes 548 and corresponding two pairs of pin holes 542 to complete the arm length setting.

Figure 4B:
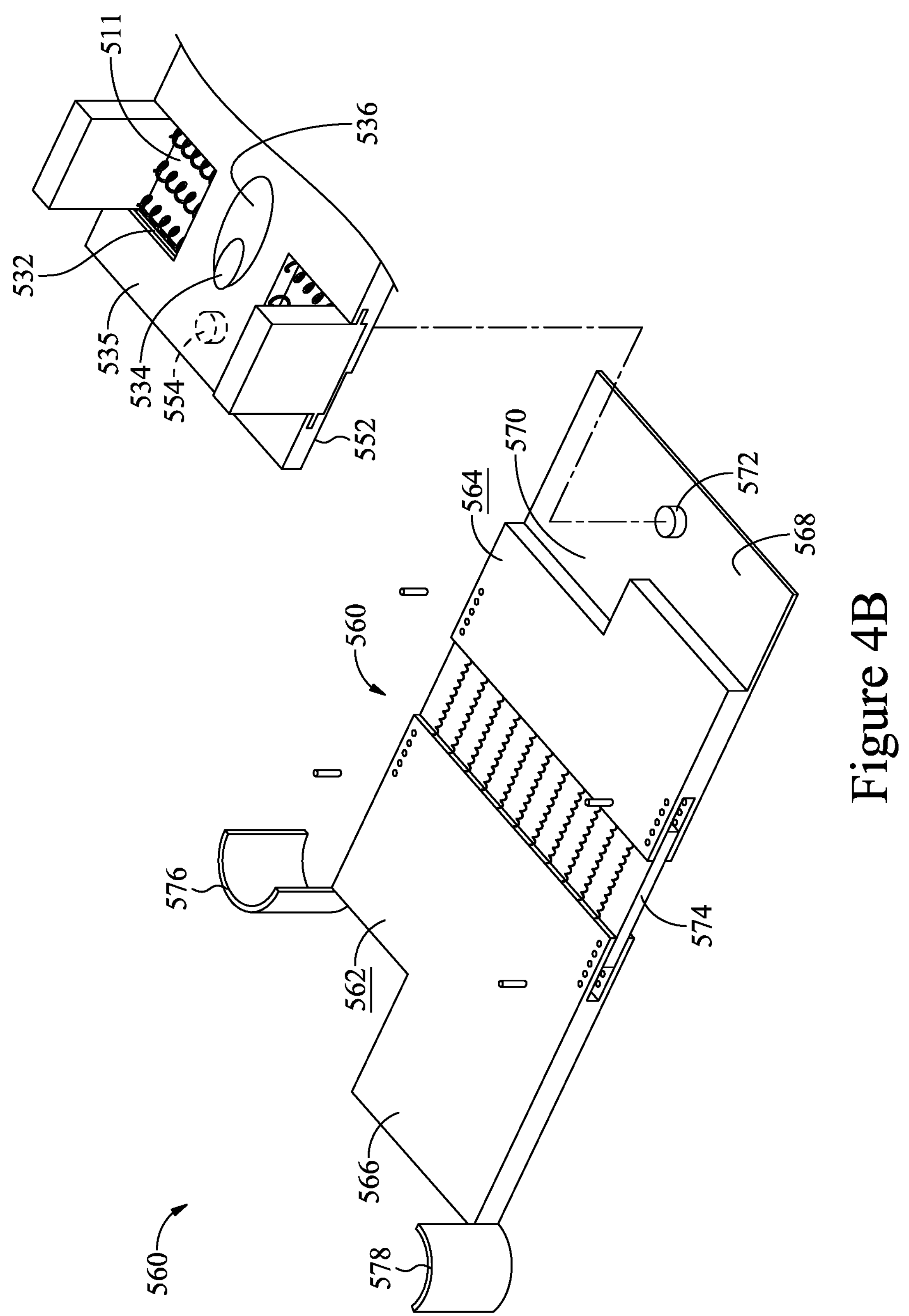
FIG. 4B shows the health care body of the health care device for the upper arm.

Please refer to FIG. 4B. Its right side is the forearm carrying base plate of FIG. 4A, which is to be combined with the one for the upper arm to form a complete upper limb carrying base plate, and thus is slightly modified. Specifically, the elbow end of forearm carrying base plate 502 (or 501) has bottom cutout 552 and bottom shaft hole 554. Its left side is upper arm carrying base plate 560 having two carrier plates 562, 564. The elbow end of carrier plate 564 has upper cutout 568 and central pivot 572 pivoted on bottom shaft hole 554. Contrasting with upper arm carrying base plate 560, because the forearm can only be bent inward, rather than folded outward, its pivoting is directional. Viewing from FIG. 4B, considering existence of the elbow end of the forearm carrying base plate 502, when pivoting counterclockwise, its distal side 535 must interfere with the elbow end of upper arm carrying base plate 560, so that if the elbow end of upper arm carrying base plate 564 is not modified accordingly, they cannot rotate with each other. Therefore, the elbow end of upper arm carrying base plate 564 has cutout 570 to accommodate distal side 535 of the elbow end of forearm carrying base plate 502.

Please refer to the left side of FIG. 4B. Because the inner side of the upper arm is connected to the body, the inner and outer sides of the upper arm have different lengths relative to upper arm carrier plate 562, and thus the distal side of axillary end 566 of carrier plate 562 has cutout 580 and semi-cylindrical part 576 connected thereto to urge against the user's axilla. Additionally, the proximal side of axillary end 566 of carrier plate 562 has a guiding sheet 578 conforming to the shoulder end of the user's upper arm. Certainly, in order to adapt to the forearm length, a length adjustment device 574 can be configured between two carrier plates 562, 564, which will not be detailed here.

Figure 4C:
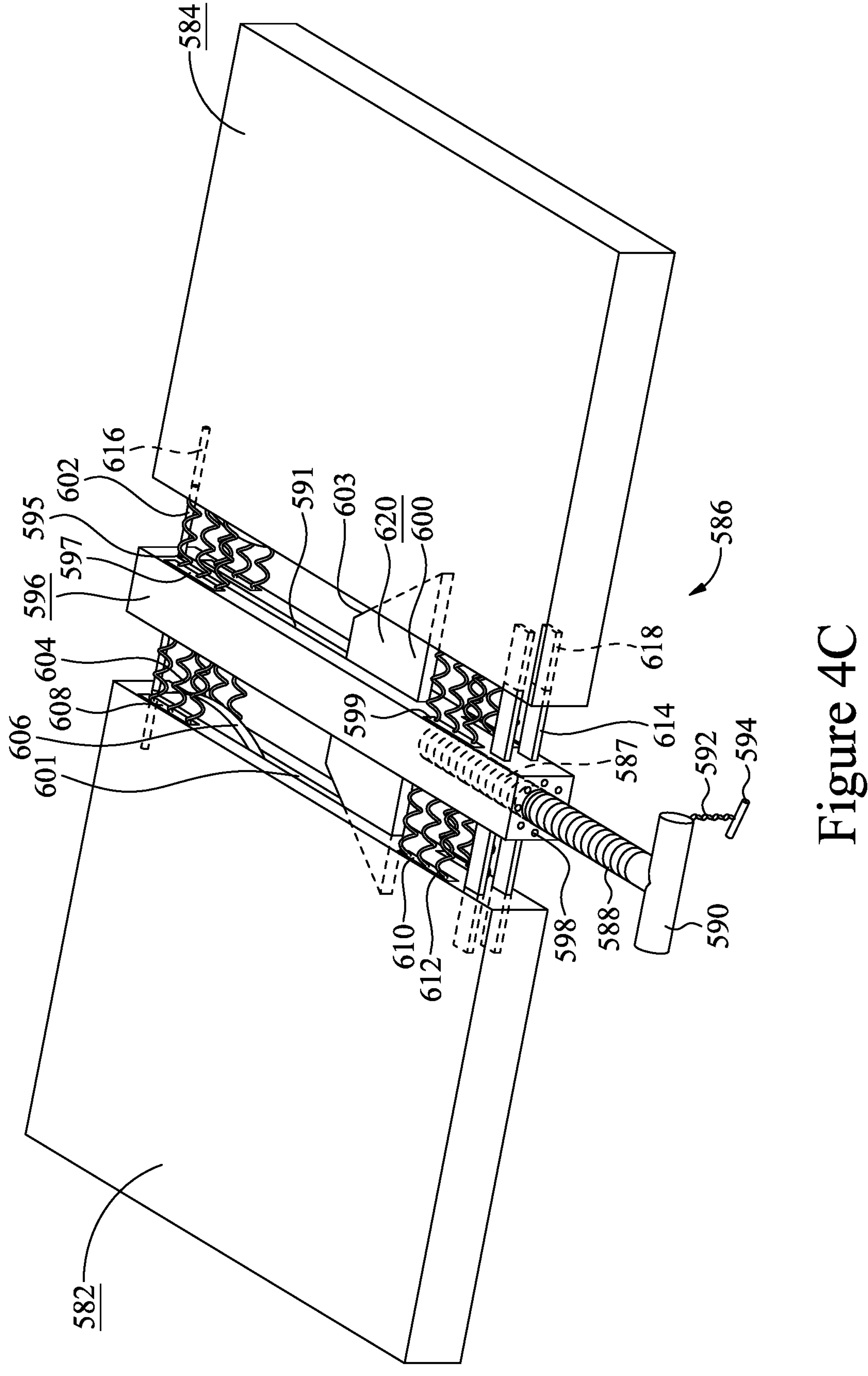
FIG. 4C is an embodiment of the length adjustment device of the health care body of the health care device.

Please refer to FIG. 4C showing an embodiment of length adjustment device 586 of the health care body of the health care device of the present invention. Length adjustment plate 596 having sliding hole 595, longitudinal central groove 591, paired grooves 597 on both sides of the distal end, paired proximal grooves 610 and grooves 599 configured on both sides of length adjustment plate 596 is configured between two carrying base plates 582, 584. Adjacent distal ends of two carrying base plates 582, 584 have paired arc convexes 606, paired grooves 608 respectively configured on both sides of paired arc convexes 606, paired middle grooves 601, and paired springs 604 (corresponding/symmetrical to arc convexes 606) configured between mutually corresponding paired grooves 608 and paired grooves 597, wherein respective two ends of paired springs 604 are connected to respective corresponding grooves 608 and grooves 597, longitudinal center groove 591 moves therein trapezoidal plate 600, and when two carrying base plates 582, 584 abut against length adjustment plate 596, arc convexes 606 are accommodated into longitudinal center groove 591. The distal plural pairs of springs 604 and the proximal plural pairs of springs 612 tend to combine carrying base plates 582, 584 and length adjustment plate 596 planarly together because the three plates 582, 584 and 596 are slidably sleeved together via distal side pieces 602 and sliding holes 616, middle groove 601 and trapezoidal piece 600, and corresponding paired guiding pieces 614 and paired guiding grooves 618 at the proximal side.

Although there are adult, children, men and women, in fact, for the forearm or upper arm, the difference of lengths usually does not exceed 5 cm. Even if comparing a four-year-old child with a person who is two meters height, it is rare that the difference of lengths exceeds 15 cm. Length adjustment plate 596 has screw hole 587 and plural positioning pinholes 598. Under the condition that the total length of three plates 582, 584 and 596 is the shortest, there is no gap thereamong. Because trapezoidal piece and screw rod assembly 620 is configured, when it is necessary to increase its virtual length, the user rotates handle 590 of screw rod 588 to push trapezoidal piece 600 to move to the distal side. Since two side bevels 603 of trapezoidal piece 600 abut against arc convexes 606, carrying base plates 582, 584 are pushed out symmetrically to adjust the total virtual length of three plates 582, 584 and 596. When screw rod 588 is rotated to an appropriate extent to obtain a suitable total virtual length of three plates 582, 584 and 596, positioning pin 594 connected to screw rod 588 via chain 592 is inserted into positioning pinhole 598 nearest to the desired position to prevent springs 604, 612 from possibly reversing screw rod 588.

Figure 4D:
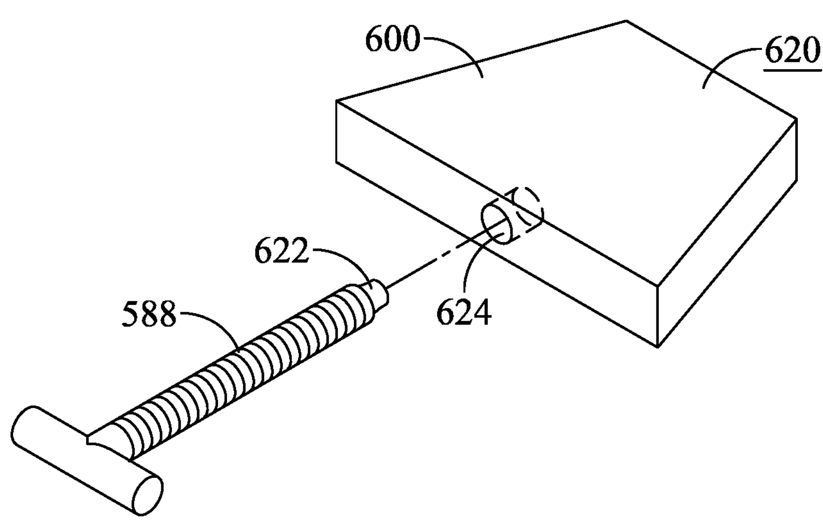
FIG. 4D is the first embodiment of the length adjustment plate of the length adjustment device of the health body of the health care device.
Figure 4E:
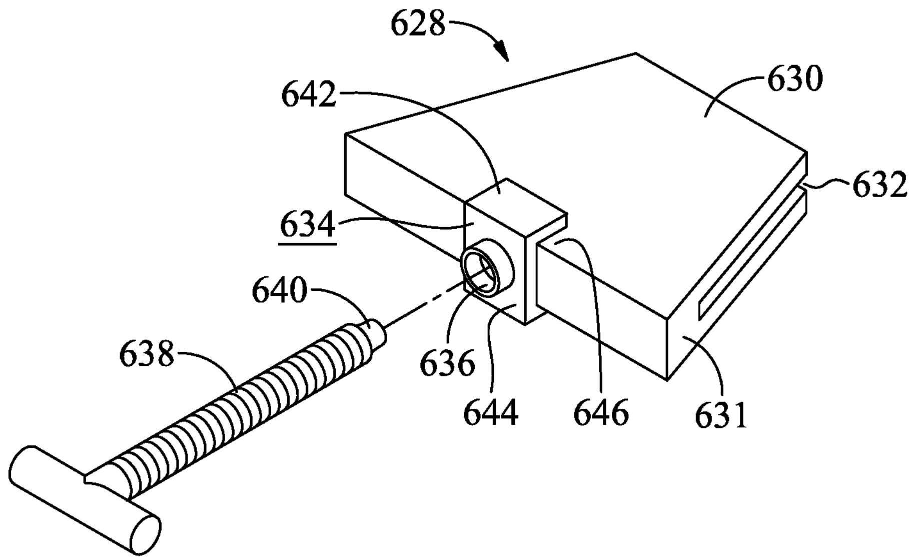
FIG. 4E is a second embodiment of the length adjustment plate of the length adjustment device of the health body of the health care device.

Please refer to FIG. 4D showing a first embodiment of trapezoidal piece and screw rod assembly 620. Trapezoidal piece 600 has a bottom hole 624 for accommodating screw rod end 622. Please refer to FIG. 4E showing a second embodiment of trapezoidal piece and screw rod assembly 628. In some cases, for example, when it is desired to control the thickness of carrying base plates 582, 584 and 596, or when the thickness of trapezoidal piece 630 is limited, chuck 634 can be configured to hold the bottom of trapezoidal piece 630, and has hole 636 to match end 640 of screw rod 638. Additionally, shallow guiding groove 632 may also be configured on side bevel 631 in proper circumstances to securely guide the relative movement between arc convexes 606 (FIG. 4C) and trapezoidal piece 630.

The preceding health care devices only are used for primary purposes or have primary functions, i.e., they are used to fix a rod-shaped acupoint work piece 300 as shown in FIG. 1. The health care devices discussed here are summarized as follows. Health care device (500) includes health care body (502) having carrying base plate (501, 503) carrying a body part, and paired recesses (511, 512), wherein the body part is an upper or lower limb or has an upper body part and a lower body part, any one of the body parts has a main limb bone, any body part or limb bone has two ends, and at least one of the two ends has a protruding features; paired positioning blocks (524, 504) are respectively slidably configured on paired recesses (511, 512), and have recesses (505, 506) corresponding to the protruding features for holding the relevant body part therebetween by the protruding feature; and a work piece holder (not shown) has a first end connected to carrying base plate (501, 503) or positioning block (524, 504), and a second end holding an acupoint work piece.

Health care device (500) includes health care body (502) having two carrying base plates (501, 503) adapting to a body part in length to carry the body part, and one end of each carrying base plate (501, 503) has paired recesses (511, 512), wherein the body part is an upper or lower limb and has an upper body part and a lower body part, any body part has a main limb bone, any body part or main limb bone has two ends, and at least one of the two ends has a protruding features; paired positioning blocks (524, 504) are respectively slidably configured on paired recesses (511, 512), and have recesses (505, 506) corresponding to the protruding features for holding the relevant body part therebetween by the protruding feature; and a work piece holder (as shown in FIG. 1 or the embodiments described later) has a first end connected to carrying base plate (501, 503) or positioning block (524, 504), and a second end holding an acupoint work piece (as shown in FIG. 1 or the embodiments described later).

In accordance with health care device (500) of the two preceding embodiments, positioning block 504 has paired lower lugs 516; recess 512 has paired side grooves 518 respectively sliding therein paired lugs 516.

In accordance with health care device (500) of the two preceding embodiments, positioning block (503) has a free end whose width is approximately the thickness of the lower arm wrist after deducting the width of paired recesses 512.

In accordance with health care device (500) of the two preceding embodiments, one of positioning block (504) has cavity (510) accommodating the thumb short abductor muscle of the palm when the palm is upright, recess (506) abutting the radial carpal protrusion of the lower arm, recess (505) abutting the ulnar carpal protrusion of the lower arm, and groove (508) staying free the palm therein.

In accordance with health care device (500) of the two preceding embodiments, the end of the free end of one carrying base plate (503) has recess (520) resting thereon an little finger abductor muscle of the user when the forearm is kept laterally upright (i.e., resting with thickness), and freely resting thereon the wrist/palm of the user when an inner (or yin) side of the lower arm is placed.

In accordance with health care device (500) of preceding embodiments, when positioning block (524) is configured in recess (511) of carrying base plate (501) carrying the forearm elbow end, positioning block (524) has recess (526) accommodating a most protruding ulnar sesamoid at an elbow end of a humerus, carrying base plate (501) has recess (534) for accommodating a most prominent part (i.e., the elbow tip) of elbow end of the ulna, and positioning block (524) and carrying base plate (501) respectively has groove (528, 536) positioning therein a respective left or lower side of prominent muscles of the lower arm when the lower arm is kept laterally upright.

In accordance with health care device (500) of preceding embodiments, two carrying base plates (501, 503) configure therebetween length adjustment medium (546) including paired central grooves (550) respectively configured on adjacent ends of carrying base plates (501, 503), linking plate (547) configured in paired central grooves (550), plural paired pinholes (542) respectively configured on opposite sides of adjacent ends of carrying base plates (501, 503), plural pinholes (548) respectively configured on linking plate (547) and corresponding to plural paired pinholes (542), and four pins (544) inserted into pinholes (548) of linking plate (547) and corresponding two pairs of pinholes (542) of carrying base plates (501, 503).

In accordance with health care device (500) of preceding embodiments, health care device (500) further includes upper arm carrying base plate (560), wherein the elbow end of forearm carrying base plate 502 (or 501) has bottom cutout (552) and bottom shaft hole (554), upper arm carrying base plate (560) has two carrier plates (562, 564), the elbow end of carrier plate (564) has upper cutout (568) and central pivot (572) pivoting on bottom shaft hole (554), and the elbow end of carrier plate (564) has another cutout (570) accommodating distal side of elbow end (535) of forearm carrying base plate (502).

In accordance with health care device (500) of preceding embodiments, the distal side of axillary end (566) of carrier plate (562) near the axilla has cutout (580) and semi-cylindrical part (576) connected thereto to urge against the user's axilla, and the proximal side of axillary end (566) has guiding sheet (578) conforming to the shoulder end of the user's upper arm.

From another aspect, health care device (500; 560) holds an acupoint work piece (as described in FIG. 1 or the following embodiments) thereon to engage in a health care onto a user, wherein the user has a body part having an acupoint, and the health care device (500; 560) includes: health care body (501, 503; 562, 564) having carrying base plate (502; 562) carrying the body part, for maintaining a first specific positional relationship with the body part, wherein the carrying base plate has an end, the body part has a main limb bone, and the body part or the main limb bone has a protruding feature corresponding to the recess; paired positioning blocks (504; 524) are respectively slidably configured on the carrying base plate, and have recesses (505; 526) corresponding to the protruding feature for confining the protruding feature to position the body part therebetween; and a work piece holder (as described in FIG. 1 or the following embodiments) has: a first end connected to the carrying base plate or the paired positioning blocks, and a second end holding the acupoint work piece, for ensuring the acupoint work piece to perform the health care work when the acupoint work piece has a second specific positional relationship with the acupoint under the first specific positional relationship.

From yet another aspect, health care device (500; 560) includes: health care body (501, 503; 562, 564) having carrying base plate (502; 562) carrying a body part of a user, for maintaining a first specific positional relationship with the body part, wherein the carrying base plate has an end, the body part has a main limb bone, and the body part or the main limb bone has a protruding feature corresponding to the recess, and the body part has an acupoint; paired positioning blocks (504; 524) are respectively slidably configured on the carrying base plate, and have recesses (505; 526) corresponding to the protruding feature for confining the protruding feature to position the body part therebetween; and a work piece holder (as described in FIG. 1 or the following embodiments) has: a first end connected to the carrying base plate or the positioning block, and a second end holding an acupoint work piece (as described in FIG. 1 or the following embodiments), for ensuring the acupoint work piece to perform the health care work when the acupoint work piece has a second specific positional relationship with the acupoint under the first specific positional relationship.

A health care device (500) includes a health care body having two carrying base plates (582; 584) for carrying a body part; and length adjustment device (586) configured on two carrying base plates (582; 584) for adjusting an apparent length of the health care body to be adapted to a length of the user's body part.

In accordance with the health care device of preceding embodiments, length adjustment device (586) is configured between two carrying base plates (582, 584) and has sliding hole 595; adjacent ends of two carrying base plates (582, 584) have paired arc convexes (606), paired middle grooves (601) and paired sliding holes (616); side piece (602) is inserted through sliding hole (595) and paired sliding holes (616), and slidably and planarly combines carrying base plates (582, 584) and length adjustment plate 596 together; and trapezoidal piece (600) is configured in paired middle grooves (601), and adjusts an apparent length of the health care body by an interaction between paired side bevels (603) and paired arc convexes (606).

In accordance with the health care device of preceding embodiments, length adjustment plate (596) has screw hole (587), plural positioning pinholes (598) and rotatable screw rod (588) for operating trapezoidal piece (600) so as to adjust a contact position between paired side bevels (603) of trapezoidal piece (600) and arc convexes (606) to adjust a total virtual length of three plates (582, 584, 596).

In accordance with the health care device of preceding embodiments, trapezoidal piece (600) has bottom hole (624), and screw rod (588) has end (622) configured freely rotatable in bottom hole 624.

In accordance with the health care device of preceding embodiments, the health care device further includes chuck (634) having first end (642) for holding bottom (646) of trapezoidal piece (630), and second end (644) having hole (636) thereon configuring therein end (640) of screw rod (638).

In accordance with the health care device of preceding embodiments, side bevel (631) of trapezoidal piece (630) has shallow guiding groove 632 for guiding therein arc convex (606).

From another aspect, health care device (500; 560) holds an acupoint work piece (as described in FIG. 1 or the following embodiments) thereon to engage in a health care onto a user, wherein the user has a body part having an acupoint, and the health care device includes: a health care body having two carrying base plates (501, 503; 562, 564) carrying the body part, for maintaining a first specific positional relationship with the body part; a length adjustment device (546; 574; 568) configured between the two carrying base plates for adjusting an apparent length of the health care body to be adapted to a length of the body part; and a work piece holder (as described in FIG. 1 or the following embodiments) having: a first end connected to one of the two carrying base plates, and a second end holding the acupoint work piece, for ensuring the acupoint work piece to perform the health care work when the acupoint work piece has a second specific positional relationship with the acupoint under the first specific positional relationship.

From yet another aspect, health care device (500; 560) includes: a health care body having two carrying base plates (501, 503; 562, 564) carrying and positioning a body part of a user, for maintaining a first specific positional relationship with the body part, wherein the body part has an acupoint; a length adjustment device (546; 574; 568) configured between the two carrying base plates for adjusting an apparent length of the health care body to be adapted to a length of the body part; and a work piece holder (as described in FIG. 1 or the following embodiments) having: a first end connected to one of the two carrying base plates, and a second end holding an acupoint work piece (as described in FIG. 1 or the following embodiments) thereon to engage in a health care onto a user, for ensuring the acupoint work piece to perform the health care work when the acupoint work piece has a second specific positional relationship with the acupoint under the first specific positional relationship.

There are also many acupoints on the foot soles, for example, the Neiting acupoint (International Code ST44) of Stomach Meridians of Foot-Yangming located at 0.5 body inch behind the web edge between the second and third toes mainly treats headache, toothache, facial edema, bloody dysentery and gastrointestinal diseases. The suitable health care device may be the one shown in FIG. 1, which will not be detailed here. Additionally, the foot sole health care device may also be obtained by adopting or modifying the health care device of FIG. 3B.

From this paragraph, the health care device suitable for the lower limb will be discussed. The lower limb includes the thigh and the shank, which are thicker but less bendable/flexible than the upper limb; for example, the rotatable angle of the knee/ankle is obviously less than that of the elbow/wrist. Additionally, the distribution regularity of acupoints in the lower limb is poorer than that of the upper limb, so that design principles of the health care device suitable for the upper limb cannot be or is not suitable for direct/complete application for the lower limb. According to acupuncture and moxibustion theories, when specific reference points of the thigh and shank are found, it can be found that there is a specific length ratio relationship between them. In details, the length from the greater trochanter of the femur to the outer Dubi acupoint (located between the femur and the tibia, and outwards below the kneecap) is 19 body inches, and the length from the outer Dubi acupoint to the lateral malleolus is 16 body inches, that is, the length ratio of these two sections is 19:16. The length is different for everyone because of their height, but the ratio is the same for everyone regardless of age. The former may mislead that the traditional Chinese medicine or the acupuncture is unscientific, while the latter arouses acclamations for mysteries of the human body or the wisdom of our ancestors.

Figure 5:
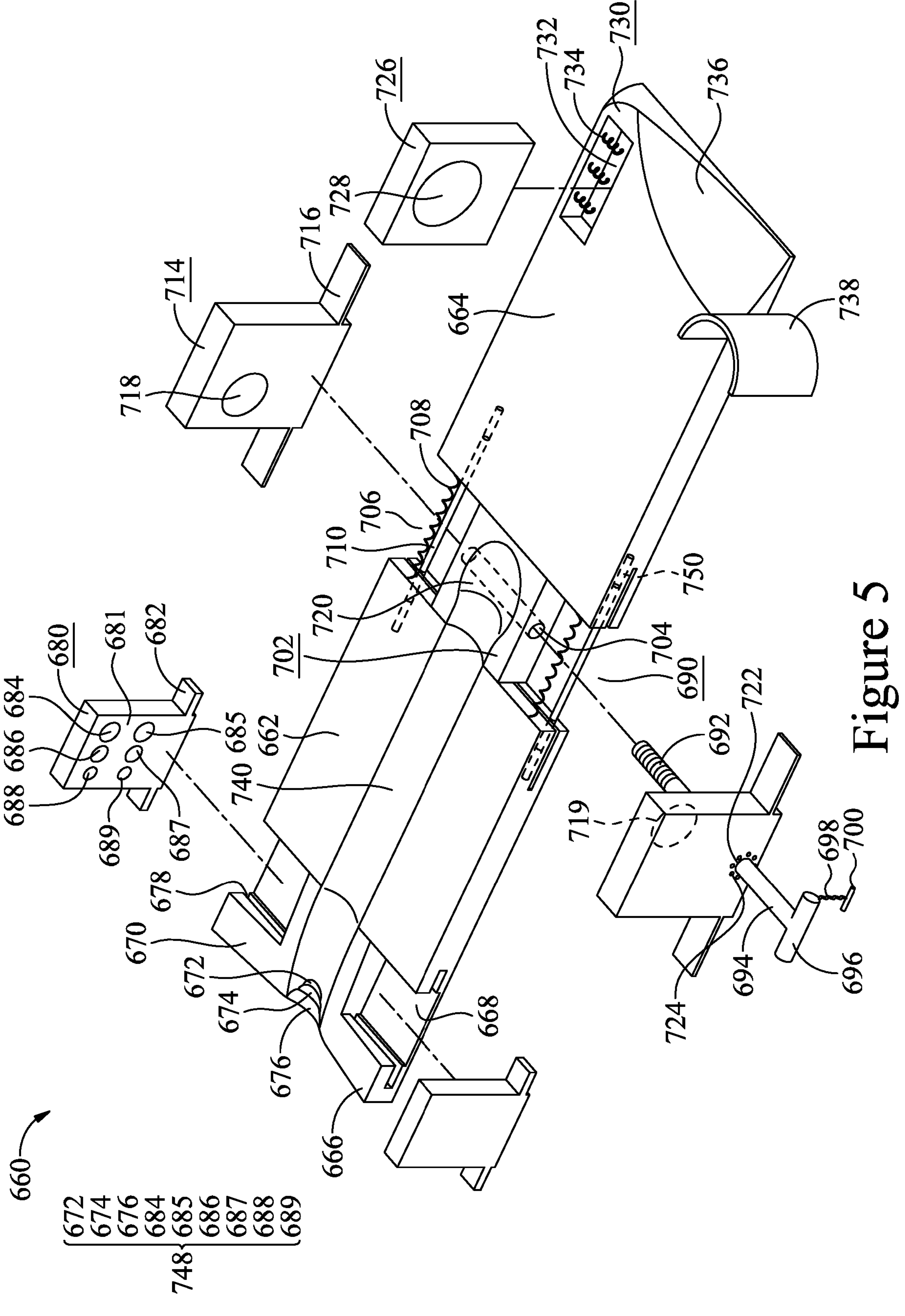
FIG. 5 is a health care device for lower limbs.

Please refer to FIG. 5. Health care body 660 of the lower limb health care device includes shank carrying base plate 662, thigh carrying base plate 664, and length adjustment device 690. Length adjustment device 690 plays the following roles: (1) forming a part of the carrying base plate or platform of health care body 660; (2) for (tibia) heel end 666 of shank carrying base plate 662, providing a carrying platform for the tibia knee end, and forming a combined shank carrying platform with shank carrying base plate 662; (3) for (femur) buttock end 730 of thigh carrying base plate 664, providing a carrying platform for the femur knee end, and forming a combined thigh and shank carrying platform with shank carrying base plate 662; (4) adjusting an apparent length of the health care body to fit the specific leg length of each user; (5) simultaneously adjusting the apparent lengths of shank and thigh carrying base plates 662, 664 for a specific user's thigh and shank; (6) simultaneously adjusting the apparent lengths of shank and thigh carrying base plates 662, 664 according to the 16:19 ratio; and (7) forming the positioning device of the knee reference feature.

Paired side grooves 668 are configured on shank carrying base plate 662 near heel end 666 for slidably configuring paired positioning blocks 680 therein. Because positioning blocks 680 are similar to positioning blocks 504, 524 of FIG. 4A, they are only briefly described here. As mentioned above, the length from the outer Dubi acupoint to the lateral malleolus is 16 body inches. Although the length from the lateral malleolus to the heel is not within the feature length of the shank, the foot sole is connected to the shank, so that it is designed as follows. Considering the accommodation of the tibia outer protrusion of the shank of the user when the user lies pronely, and the accommodation of the calf, the calcaneal tendon and the calcaneus when the user lies supinely, shank carrying base plate 662 has central concave 740, and heel end 666 has deeper recess 670. Paired side grooves 668 are configured on shank carrying base plate 662 near heel end 666. Each groove 668 has paired slots 678 for slidably configuring paired lugs 682 configured on each positioning block 680. Heel height adjustment medium 748 is configured on positioning blocks 680 and heel end 666 for accommodating heel heights of different users. Ankle engaging recesses are configured on paired opposite surfaces 681 of paired positioning blocks 680. Taking distal positioning block 680 of FIG. 5 as an example, its opposite surfaces 681 have large lateral malleolus recess 684, middle lateral malleolus recess 686 and small lateral malleolus recess 688. The purpose of configuring these three recesses is to match the user's height, and to accommodate therein the lateral malleolus. In details, in general, although there are children, adults, fatties and skinnies, in fact, the difference in length of shank (or including the distance between the lateral malleolus and the foot sole) is usually less than 50%. Specifically, the vertical (when standing) or horizontal (when lying) distance or height from the lateral malleolus to the heel is about 4 cm for a child and about 7 cm for a person of about 170 cm. Therefore, three recesses 672, 674, 676 are configured on recess 670 for the heel portion, paired recesses 672 and 688, 674 and 686, and 676 and 684 can well accommodate the specific length of each user, and in this manner, heel height adjustment medium 748 works.

Certainly, in design, three heel recesses 672, 674, 676 can be a continuous inclined surface to create a stepless effect, and positioning block 680 can simply have one lateral malleolus recess. On the contrary, if the width of opposite surfaces 681 is increased, heel end 666 can be narrowed, and three recesses 672, 674, 676 are not needed. Additionally, the proximal positioning block 680 has a recess (not shown) corresponding to the medial malleolus. For facilitating the health care body assembly, opposite surfaces 681 on paired positioning blocks 680 can be respectively provided with three recesses 685, 687, 689 (or 684, 686, 688) corresponding to the medial malleolus (or lateral malleolus), that is, it is unnecessary to pay attention to which positioning block 680 belongs to the distal or proximal side. It is also worth noting that when using the health care body, because acupoints are located on the leg back or the calf, the user may lie supinely or pronely. Taking FIG. 5 as an example, when lying supinely, the lateral malleolus of the right leg is on the distal side; when lying pronely, the lateral malleolus of the left leg is on the distal side. Thus the distal positioning block is provided with three additional malleolus recesses 685, 687, 689 for positioning when lying pronely. It is also worth noting that when lying supinely, the calcaneal tendon will raise the height of the lateral malleolus, but when lying pronely, the distance between the leg back and the lateral malleolus is shortened. Thus, the height of three lateral malleolus recesses 685, 687, 689 on positioning block 680 is less than that of three lateral malleolus recesses 684, 686, 688. Needless to say, the springs pulling paired positioning blocks 680 closer to each other are the same as those in FIG. 4A, which will not be detailed here.

Buttock end 730 of health care body 660 has recess 736 for accommodating muscles connecting between buttocks and the thigh, and its distal end has accommodating hole 732 for accommodating positioning block 726 having positioning hole 728 for containing the trochanter major protrusion at the femur buttock end. Plural springs 734 are configured between the distal wall of accommodating hole 732 and the distal wall of positioning block 726 to abut positioning block 726 against the trochanter major protrusion at the femur buttock end for positioning. The proximal side of buttock end 730 of thigh carrying base plate 664 has stop 738 for abutting against the bottom edge of the groin, to complete the complete positioning of buttock end 730 of the lower limb.

Please refer to the middle part of FIG. 5 showing length adjustment device 690 of health care body 660. Basically, length adjustment device 690 simultaneously serves as parts of both shank and thigh, and forms a complete platform for carrying shank and thigh with shank carrying base plate 662 and thigh carrying base plate 664. The shank and thigh carrying base plates 662, 664 are interconnected to have a longitudinally adjustable distance and form an integral lower limb health care body 660 by at least one pair of rods 710 and at least two pairs of rod holes 712 seelving paired rods 710 and respectively configured on adjacent two ends and on both sides of carrying base plates 662, 664.

Figure 5A:
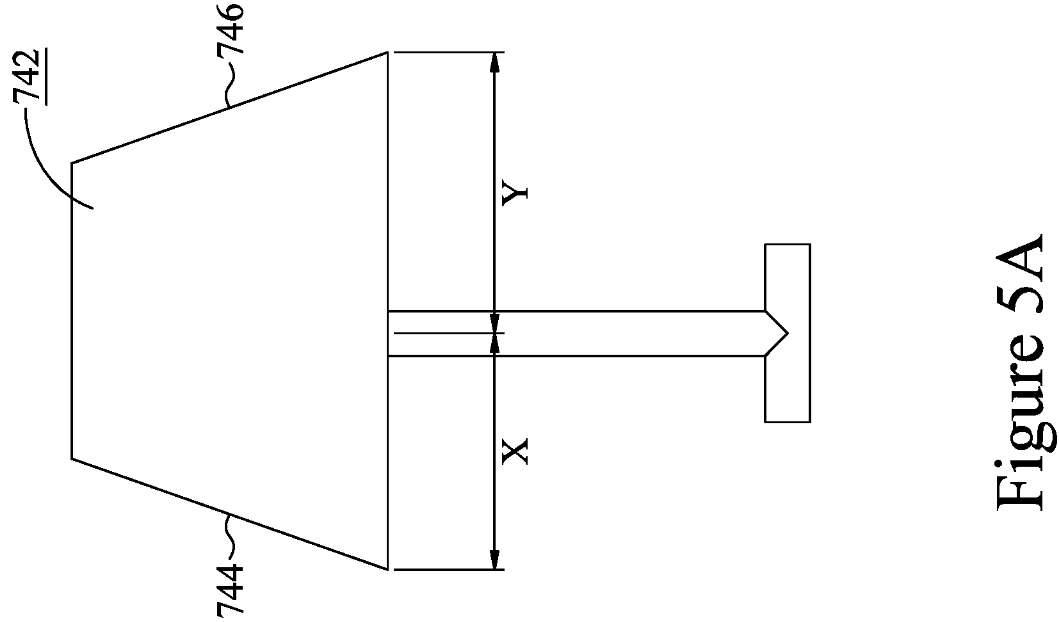
FIG. 5A is a length adjustment plate of the lower limb health care body.

Length adjustment device 690 mainly includes carrying base plate 702, operating rod 694 and length adjustment trapezoidal piece 742 (also refer to FIG. 5A). Length adjustment device 690 is similar to length adjustment device 586 in FIG. 4C. In brief, only main differences are described here. Carrying base plate 702 has central recess 720, screw hole 704 and a distal middle groove (not shown, for accommodating length adjustment trapezoidal piece 742). Length adjustment trapezoidal piece 742 has two side bevels 744 and 746 for abutting against arc convexes (not shown, for clarity, refer to FIG. 4C). The distal half of operating rod 694 has thread 692 for screwing into screw hole 704 to urge length adjustment trapezoidal piece 742 in the middle groove at the distal side of carrying base plate 702 as required, to increase the apparent length of the shank and thigh carrying platform according to the actual demand. When the user lies pronely, central recess 720 is provided for accommodating the user's protrusion of a kneecap.

Paired positioning blocks 714 are configured in space 706 between thigh and shank carrying base plates 664, 662 for positioning the corresponding features of tibia and femur around the knee. Specifically, for the knee, the most protruding part of the outer side is the knee tuberosity of the tibia, and the most protruding part of the inner side is the knee tuberosity of the femur. Thus, positioning block 714 at the distal end has recess 718 to accommodate the knee tuberosity of the tibia. Because only legs are changed when lying supinely and pronely, and the position of the knee tuberosity of the tibia will not be changed, only one recess 718 is configured. Specifically, although the height of the tuberosity is different when lying supinely and pronely, it can be compensated by the depth of central recess 720 or the central height of carrying base plate 702. Likewise, only one accommodating recess 719 corresponding to the knee tuberosity of the femur on proximal end positioning block 714 in FIG. 5 is needed. As shown in FIG. 5, the shape of lugs 716 of positioning block 714 is significantly different from that in FIG. 4A, because thigh and shank carrying base plates 664, 662 are separated from each other during the operation of length adjustment device 690. Therefore, lugs 716, slidably configured in paired sliding slots 750 on thigh and shank carrying base plates 664, 662 respectively, are lengthened to be slidably positioned between positioning blocks 714 in the separation process of thigh and shank carrying base plates 664, 662. Additionally, the springs (not shown, for clarity, refer to FIG. 4A) are respectively configured between positioning blocks 714 and carrying base plates 662, 664, so that positioning blocks 714 tend to be close to each other, to position the user's knee joint.

One or more pairs of springs 708 are used to keep thigh and shank carrying base plates 664, 662 close to each other. Because the characteristics of this embodiment, paired spring 708 may be installed after the positioning blocks are installed. Proximal positioning block 714 has through hole 722 for freely passing therethrough operating rod 694, and plural pinholes 724 are configured on the proximal surface, so that when operating rod 694 is in the correct operating position, it can be fixed through pinning pin 700 connected to handle 696 through chain 698 in pinhole 724. Please refer to FIG. 5A, the configurations of two side bevels 744 and 746 cause distances between each side bevel and the center of operating rod 694 to be respectively X and Y, and distances of X and Y have a ratio relationship of 16:19. Length adjustment device 690 is pushed away from shank and thigh carrying base plates 662, 664 according to this ratio relationship, to perfectly and nondeformably adjust acupuncture lengths of thigh and shank for each user.

The health care body of the lower limb health care device of the present invention is summarized as follows. Health care body (660) includes shank carrying base plate (662); thigh carrying base plate 664; and length adjustment device (690) having a first part forming a combined shank carrying platform with shank carrying base plate (662), and a second part forming a combined thigh carrying platform with thigh carrying base plate (664).

In accordance with the health care body of the preceding embodiment, length adjustment device (690) serves as a positioning device for the reference feature of the knee.

According to a second embodiment of the health care body of the present lower limb health care device, health care body (660) includes shank carrying base plate (662) for carrying a user's shank and lateral malleolus; thigh carrying base plate (664) for carrying the user's thigh and the trochanter major protrusion of the femur; and length adjustment device (690) having a first and a second parts for respectively carrying the user's the knee lateral tuberosity of the tibia of the shank and the knee medial tuberosity of the femur of the thigh, wherein length adjustment device (690) can adjust the apparent length of the health care body to accommodate the user's specific leg length.

In accordance with the health care bodies of the preceding embodiments, shank carrying base plate (662) and thigh carrying base plate (664) respectively co-form a shank and a thigh carrying platforms with the first and second parts of length adjustment device (690), and the length adjustment device simultaneously adjusts apparent lengths of the corresponding thigh and shank carrying platforms.

According to a second embodiment of the health care body of the present lower limb health care device, health care body (660) includes shank carrying base plate (662) for carrying a user's shank and lateral malleolus; thigh carrying base plate 664 for carrying the user's thigh and trochanter major protrusion of the femur; and length adjustment device (690) having a first and a second parts for respectively carrying the user's the knee lateral tuberosity of the shank tibia and the knee medial tuberosity of the thigh femur, wherein shank carrying base plate (662) and thigh carrying base plate (664) respectively co-form a combined shank and thigh carrying platforms with the first and second parts of length adjustment device (690), which simultaneously adjusts under a ratio of 16:19 the combined shank and thigh carrying platforms.

In accordance with the health care bodies of the preceding embodiments, shank carrying base plate (662) has central concave (740), wherein when the user lies pronely, central concave (740) contains the outer protrusion of the shank tibia, and when the user lies supinely, central concave (740) accommodates the shank calf.

In accordance with the health care bodies of the preceding embodiments, shank carrying base plate (662) has heel end (666) having deeper recess (670) for containing therein the calcaneal tendon and the calcaneus when the user lies supinely.

In accordance with the health care bodies of the preceding embodiments, shank carrying base plate (662) has heel end (666) and paired positioning blocks (680) slidably configured close to heel end (666) for containing a user's lateral malleolus and medial malleolus.

In accordance with health care bodies (660) of the preceding embodiments, heel height adjustment medium (748) is configured on paired positioning blocks (680) and heel end (666) for being adapted to the specific heel height of each user.

In accordance with health care bodies (660) of the preceding embodiments, paired positioning blocks (680) respectively have opposite surfaces (681) having recesses (684, 685, 686, 687, 688, 689) so designed that regardless of whether the user is lying supinely or pronely, and whether positioning blocks (680) are interchanged or not, the recesses can correctly accommodate the user's lateral malleolus and medial malleolus, respectively.

In accordance with health care bodies (660) of the preceding embodiments, thigh carrying base plate (664) has buttock end (730) having recess (736) for accommodating the muscles connecting between buttocks and the thigh; positioning block (726) for containing the trochanter major protrusion at the femur buttock end of the user; and stop (738) configured on a side of buttock end (730) for abutting against the bottom edge of the user's groin.

In accordance with health care bodies (660) of the preceding embodiments, length adjustment device (690) includes carrying base plate (702), operating rod (694) and length adjustment trapezoidal piece (742); length adjustment trapezoidal piece (742) has two side bevels (744, 746) for respectively abutting against shank and thigh carrying base plates (662, 664); distances between two side bevels (744, 746) and the center of operating rod (694) respectively are X and Y; and distances of X and Y have a ratio relationship of 16:19.

In accordance with health care bodies (660) of the preceding embodiments, length adjustment device (690) includes paired positioning blocks (714) configured between thigh and shank carrying base plates (664, 662) for simultaneously positioning the knee tuberosity of the tibia and the knee tuberosity of the femur of a user.

From another aspect, health care body (660) holds an acupoint work piece (as described in FIG. 1 or the following embodiments) thereon to engage in a health care onto a user, wherein the user has a lower limb having a shank, a thigh and an acupoint, and the health care body includes: a shank carrying base plate (662) and a thigh carrying base plate (664) respectively carrying and positioning the shank and the thigh, for maintaining a first specific positional relationship with the shank or the thigh; a length adjustment device (690) configured between the shank carrying base plate and the thigh carrying base plate, wherein the shank carrying base plate, the thigh carrying base plate and the length adjustment device have an actual total length and a virtual length, and the length adjustment device is used for adjusting the virtual length of the health care body; and a work piece holder (as described in FIG. 1 or the following embodiments) having: a first end connected to the shank or the thigh carrying base plate, and a second end holding the acupoint work piece thereon, for ensuring the acupoint work piece to perform the health care work when the acupoint work piece has a second specific positional relationship with the acupoint under the first specific positional relationship.

From yet another aspect, health care device (660) includes: a health care body having a shank carrying base plate (662) and a thigh carrying base plate (664) carrying and positioning a lower limb/body part of a user, for maintaining a first specific positional relationship with the body part, wherein the lower limb has a shank, a thigh and an acupoint; length adjustment device (690) configured between the shank carrying base plate and thigh carrying base plate, wherein the shank carrying base plate, thigh carrying base plate and length adjustment device have an actual total length and a virtual/apparent length, and the length adjustment device is used for adjusting the virtual length of the health care body; and a work piece holder (as described in FIG. 1 or the following embodiments) having: a first end connected to the shank or thigh carrying base plate, and a second end holding an acupoint work piece (as described in FIG. 1 or the following embodiments) thereon to engage in a health care onto a user, for ensuring the acupoint work piece to perform the health care work when the acupoint work piece has a second specific positional relationship with the acupoint under the first specific positional relationship.

Figure 6:
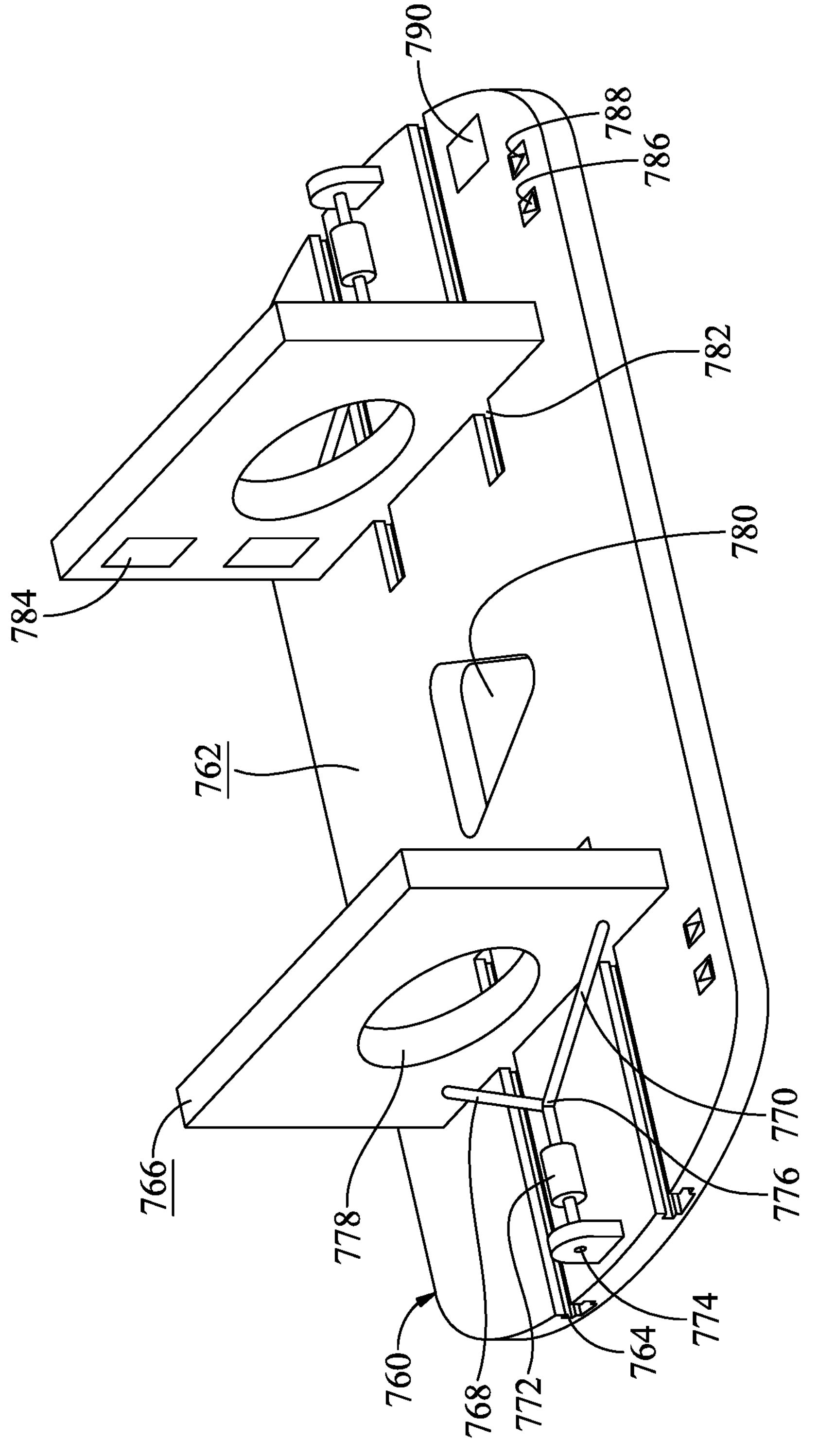
FIG. 6 is a health care device for the head.

After discussions above, only the head of the human body remains untreated. In this regard, please refer to FIG. 6 showing head health care body 760 including base plate 762, paired slots 764 on either of left and right sides, paired oil cylinders 772, paired head positioning plates 766, paired pressure sensors 784 configured on each paired positioning plates 766, circuit configuration 790 integrating the operation of pressure sensors 784 and oil cylinders 772, and paired oil cylinder forward and backward buttons 786, 788 configured on either of left and right sides of base plate 762. Specifically, below each positioning plate 766, paired lower protruding sliders 782 having two side lugs are slidably configured in respective paired slots 764. Oil cylinder 772 has first end 774 fixed on base plate 762 and second end 776 fixed on the corresponding positioning plate 766 by paired connecting rods 768, 770, so that the distance between paired positioning plates 766 is determined by paired oil cylinders 772.

When using, because there are many acupoints on face and back of the head, health care body 760 is not only suitable for the user lying supinely to perform the health care work on the face, but also suitable for the user lying pronely to perform the healthcare work on back of the head. It can be understood why the center of base plate 762 is provided with inverted triangular hole 780 to expose eyes and nose when the user lies pronely. When forward button 786 is operated, oil cylinders 772 pushes positioning plates 766 toward each other. First, the user's paired ears will pass through ear holes 778 on positioning plates 766, followed by circuit arrangement 790 to cut off the power immediately when the temple, being the most protrusive on the user's head, is predeterminedly touched by related pressure sensors 784, to complete the head's positioning. No matter whether the holder of the acupoint work piece is configured on base plate 762 or positioning plate 766, it is easy to define the relative position with the acupoint, and thus not detailed here.

It is worth noting that the movement device (i.e., oil cylinder 772 in the embodiment) of the preceding head healthcare device can also be simply modified to displace the length adjustment device of the more preceding embodiments to digitize and accurately control the total amount of displacement, which will not be detailed here.

The head health care body is summarized as follows. Healthcare body (760) includes base plate (762) supporting a user's head; paired head positioning plates (766), symmetrical to the head's longitudinal axis, and movably configured transversely on base plate (762) for positioning the user's head to ensure the acupuncture work on the user's head or face; movement device (772) configured between base plate (762) and paired head positioning plates (766) for determining a spacing of paired head positioning plates (766) to be adapted to a width of the user's head or face; and an acupoint work piece configured on base plate (762) or head positioning plates (766) to perform a work to the acupoint.

In accordance with the preceding head health care body, the head health care device further includes pressure sensor (784) configured on at least one of paired positioning plates (766), whose position corresponds to a vicinity of the user's temple, and when paired positioning plates (766) move until the head is touched by or sandwiched with pressure sensors (784), the movement device power is cut off.

In accordance with the preceding head healthcare body, movement device (772) is oil or pneumatic cylinder.

In accordance with the preceding head healthcare body, either side of base plate (762) has paired buttons (786, 788) controlling the movement device to move forward and backward.

In accordance with the preceding head health care body, base plate (762) has paired slots (764); and below each positioning plate (766), paired lower protruding sliders (782) having two-side lugs are slidably configured in corresponding paired slots (764).

In accordance with the preceding head health care body, movement device (772) has first end (774) fixed on base plate (762), and second end (776) fixed on respective positioning plate (766) by paired connecting rods (768, 770).

In accordance with the preceding head healthcare body, base plate (762) has inverted triangular hole (780) to expose eyes and nose when the user lies pronely.

In accordance with the preceding head health care body, each positioning plate (766) has ear hole (778) for passing through the user's ear.

From another aspect, healthcare body (760) holds an acupoint work piece (as described in FIG. 1 or the following embodiments) thereon to engage in a health care onto a user, wherein the user has head, face and acupoint, and the health care body includes: a base plate 662 carrying thereon the head or face, for maintaining a first specific positional relationship with the head or face; paired head positioning plates (766), symmetrical to the head's longitudinal axis, and movably configured transversely on the base plate for positioning the head or face to perform a healthcare work on the user through the acupoint; and a work piece holder (as described in FIG. 1 or the following embodiments) having: a first end connected to the base plate, and a second end holding the acupoint work piece thereon, for ensuring the acupoint work piece to perform the healthcare work when the acupoint work piece has a second specific positional relationship with the acupoint under the first specific positional relationship.

From yet another aspect, health care body 760 includes: a base plate 664 carrying thereon a user's head or face, for maintaining a first specific positional relationship with the head or face, wherein the head or face has an acupoint; paired head positioning plates 766, symmetrical to the head's longitudinal axis, and movably configured transversely on the base plate for positioning the head or face to perform a healthcare work on the user through the acupoint; movement device 772 configured between base plate 762 and paired head positioning plates 766 for determining a spacing of the paired head positioning plates in adaptation to a width of the user's head or face; and a work piece holder (as described in FIG. 1 or the following embodiments) having: a first end connected to the base plate, and a second end holding an acupoint work piece (as described in FIG. 1 or the following embodiments) thereon to engage in the healthcare work, for ensuring the acupoint work piece to perform the healthcare work when the acupoint work piece has a second specific positional relationship with the acupoint under the first specific positional relationship.

Those who have researched acupuncture and have a keen mind may question that although the acupoint positioning mechanism described above is new, it is not yet complete or ideal. The reason why it is not complete is that taking the head healthcare body as an example, there are still acupoints on the head top. If the positioning device for the acupoint workpiece is configured on positioning plate 766, it seems that the distance is relatively long, which may raise an "accurate" positioning issue. Therefore, it seems that the following logic can be developed: If the accurate positioning of the acupoints in the head's front, back and top can be solved, this solution can be applied or modified, and the accurate positioning for the rest body will naturally be obtained. Certainly, in order to avoid any doubt for the skilled person in the art, while disclosing the solution below, it will be briefly explained why the accurate positioning for other acupoints is a piece of cake.

Figure 7:
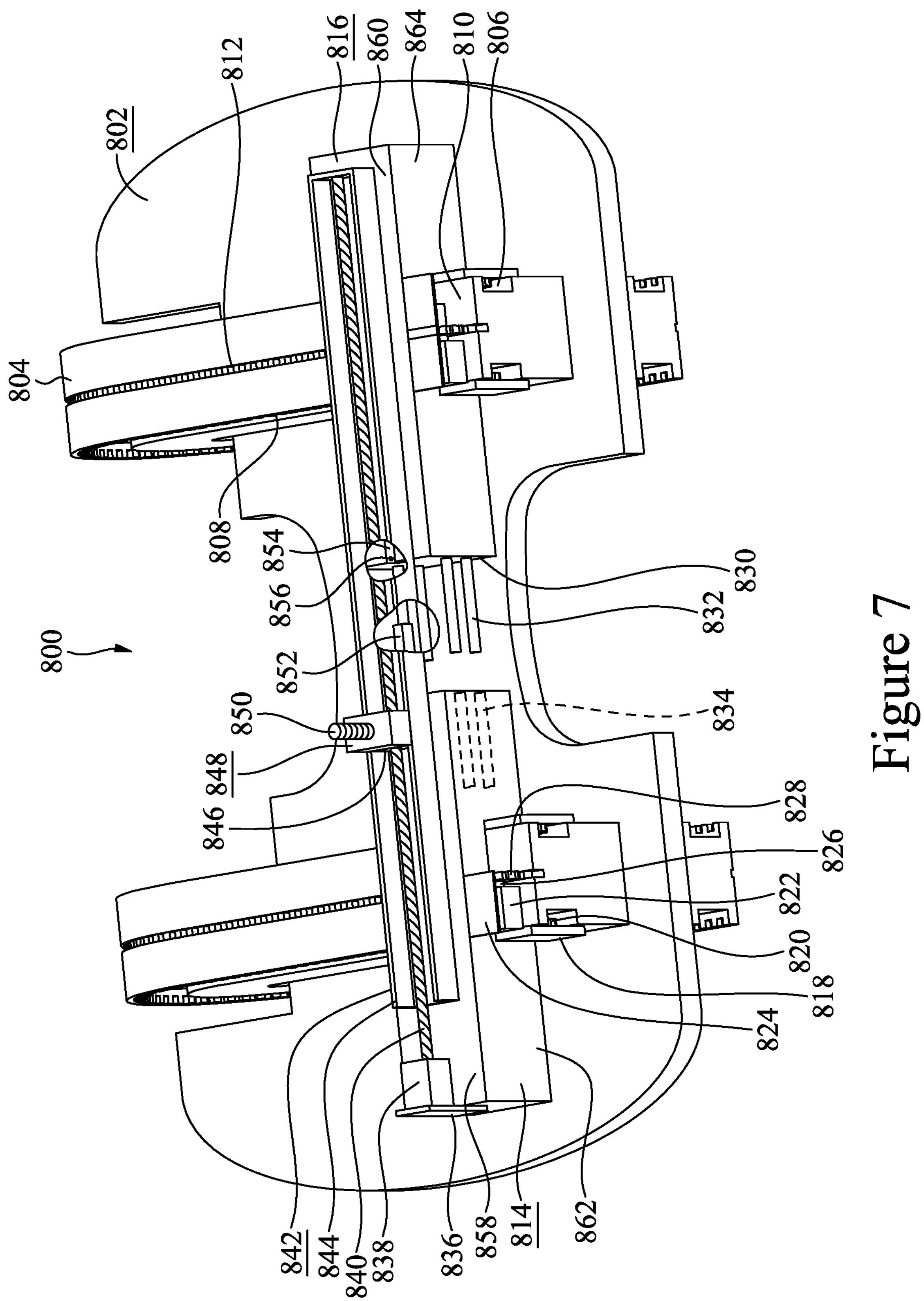
FIG. 7 is a head health care device that can be accurately positioned.

FIG. 7 shows head health care device 800 for accurate positioning purposes, which includes health care body 802, where two positioning plates 766 in FIG. 6 are changed to two rail bodies 804 in this figure. In appearance, it seems that the complexity is involved, but this is the only way for the invention to jump from the basic level to the advanced level, which is described hereinafter. To avoid the figure being too complicated, the first displacement/adjustment device for the distance between two rail bodies 804 is disclosed in the preceding embodiments, and thus is no longer shown in FIG. 7. Each rail body 804 has upper surface 810, paired gear slots 806 configured on two longitudinal sides close to upper surface 810, and lower gear racks 808 are configured on the top surface of gear slots 806. Additionally, upper gear rack 812 is configured longitudinally along upper surface 810.

The first displacement/adjustment device of two rail bodies 804 adjusts the distance therebetween, and carrier bodies 814, 816 carry work base 848. Carrier bodies 814, 816 are two-piece because they need to follow the distance change between two rail bodies 804, and to fully perform the carrying work. Paired positioning rods 832 are respectively configured on distal and proximal sides of left end surface 830 of carrier body 816, and paired positioning slots 834 are correspondingly configured on carrier body 814, so that no matter how two rail bodies 804 change within the necessary distance adjustment range, upper surfaces 858, 860 of two carrier bodies 814, 816 are coplanar.

Proximal surfaces 862, 864 of carrier bodies 814, 816 each has paired positioning plates 818, each of which has positioning gear 820 meshing with lower gear rack 808. Each proximal surface 862, 864 fixes therewith stepping motor 822 and gear protection sheet (with/without gear slot) 824. Stepping motor 822 has motor shaft 826 coaxially fixing therewith gear 828. Therefore, when gear 828 is driven to rotate by stepping motor 822, because carrier bodies 814, 816 have been fastened to lower gear rack 808 by positioning gear 820, gear 828 will definitely mesh with upper gear rack 812 (or between upper gear rack 812 and gear protection sheet 824 with gear) to longitudinally move entire carrier bodies 814, 816 along two rail bodies 804. Additionally, the whole mechanism, i.e., all components carried and configured on carrier bodies 814, 816, achieves the second displacement/position adjustment function (that is, move longitudinally along rail body 804), under cooperation of two sets of upper gears 828 and paired lower gears 820. The functions/purposes of this second displacement/position adjustment will be described later.

Side positioning plate 836 is fixed on carrier body 814 for fixing another stepping motor 838 driving screw rod 840. The screw rod nest 842 is fixed on upper surfaces 858, 860 for accommodating screw rod 840, and has two side wall upper surfaces 844. Work base 848 is driven by stepping motor 838 to move along two side wall upper surfaces 844 through moving piece 846 screwed to screw rod 840 to determine its work position. To adapt to the distance change between two rail bodies 804, the right side bottom of screw rod nest 842 has middle protruding piece 852, and upper surface 860 has corresponding groove 854 for allowing middle protruding piece 852 to freely slide in groove 854. Certainly, to increase the sliding smoothness, plural balls 856 may be configured between middle protruding piece 852 and groove 854. Therefore, the mechanism completes the third free movement of work base 848 on screw rod nest 842 to change its working position free from any influence from the preceding first and second displacements/position adjustments. Certainly, the functions/purposes of this third displacement/position adjustment or change will be detailed later. Work base 848 has fixing screw bolt 850 fixing a work piece, which will be detailed later.

The standard body inch at the head and face depends on the Touwei acupoint of Stomach Meridians (International Code ST8, located at 0.5 body inch behind the hairline of the forehead, and mainly treating eye pain, unclear vision, unbearable headache, splitting headache, dizziness), and the distance between left and right Touwei acupoints defines 9 standard horizontal head body inches. Specifically, after the distance between two rail bodies 804 is adjusted by first displacement/adjustment device 772 in FIG. 6 to position a user's face, the third displacement/position adjustment mechanism (component assembly 838-856) can be activated to perform the healthcare or medical work. First, this kind of work is therefore performed very delicately, because the positioning of the stepping motor can be extremely accurate; second, stepping motor 838 is activated first to obtain the specific size of each person, that is, moving work base 848 first to ascertain Touwei acupoints (International Code ST8), followed by calculating the real distance therebetween, and proportionately correlating this real distance to 9 body inches, whereby we can know the exact length of a body inch a specific person has; third, when the exact size of the specific person is known, it can be accurately found out where the other acupoints are based on this; fourth, when it can be accurately found out where the specific acupuncture point is, the healthcare or medical work on the acupoint is performed, that is, there is no risk of misdiagnosis or mistreatment.

As mentioned, in order not to make the figure too complicated, health care body 802 is somewhat simplified. Another point that should also be mentioned here is that FIG. 7 is suitable for the head and face healthcare. For Governor Vessel, there are Yamen acupoint (International Code GV15), Fengfu acupoint (International Code GV16), Naohu acupoint (International Code GV17), Qiangjian acupoint (International Code GV18) and Houding acupoint (International Code GV19) in the head back, and thus, the positions of health care body 802 corresponding to these acupoints must be hollowed out. There are two ways of hollowing out, hollowing horizontal grooves to expose spaces corresponding to these acupoints, or providing longitudinal holes corresponding to these acupoints. Because this is not difficult, it will not be further detailed or illustrated in this regard.

Figure 7A:
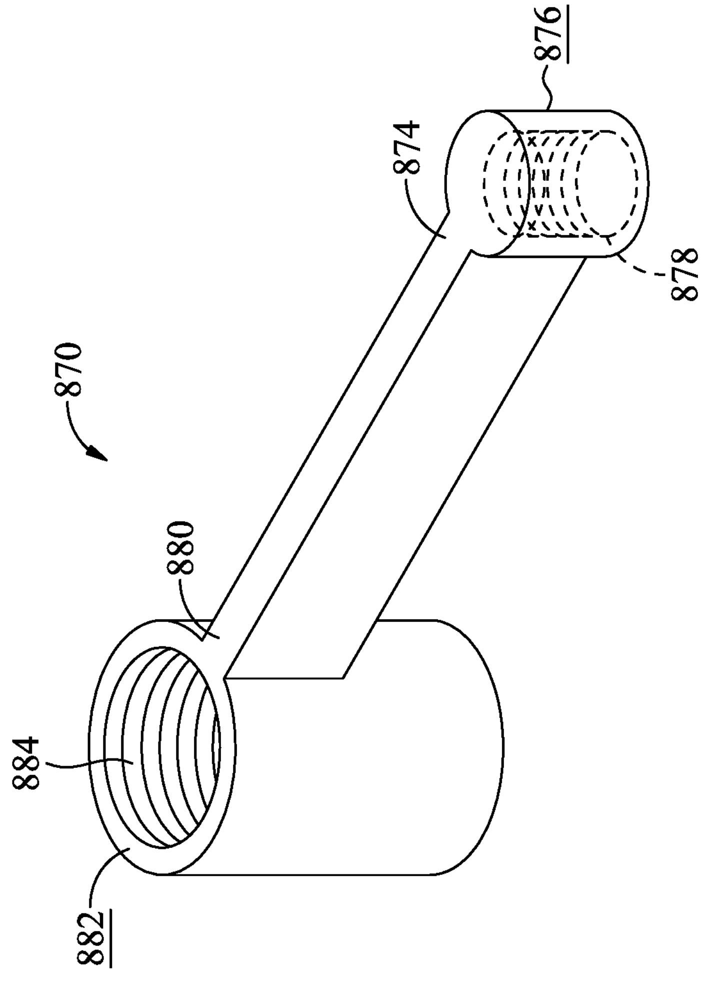
FIG. 7A is the second embodiment of the connecting piece of the acupoint work piece.

Please refer to FIG. 7A showing acupoint workpiece connecting piece 870 having first end 874 connected to fixing nut 876, and second end 880 connected to acupoint workpiece nut 882. Fixing nut 876 is screwed on fixing screw bolt 850 with its internal thread 878, so acupoint workpiece connecting piece 870 is precisely positioned on carrier bodies 814, 816, and work nut 882 is screwed to an acupoint work piece with its internal thread 884 to perform the healthcare or medical act on a certain acupoint. More details will be described later.

The standard head vertical body inch is defined to 12 body inches from the front hairline to the back hairline. To find out how many centimeters the head vertical body inch a specific user has, the second displacement/position adjustment mechanism (component assembly 808, 812 and 818-828) is activated. Specifically, when stepping motor 822 is activated, upper gear 828 and paired lower gears 820 will drive carrier bodies 814, 816 to move longitudinally along two rail bodies 804, by which a probe workpiece fixed on work base 848 ascertain the real size between the front and back hairlines of a specific user. As this real size is defined as 12 standard head vertical inches, it can be known how many centimeters each head vertical inch of the user has. It may deserve mentioned here that to move carrier bodies 814, 816 driven by stepping motor 822 smoothly along the longitudinally curved rail 804, the interactive bottom surfaces related to carrier bodies 814, 816 and upper surfaces of two rails 804 can have an appropriate arc, to facilitate the mutual relative movement, which will not be detailed here.

Although the first (772), second (component assembly 808, 812 and 818-828) and third (component assembly 838-856) displacement/position adjustment mechanisms in FIGS. 6, 7 and 7A take the head as an example, it should not be difficult for the skilled artisan to directly apply or modify it to the upper limb, lower limb or trunk healthcare body, so it will not be detailed here. However, it can be known that by the preceding mechanism, the following amazing effects can be achieved: 1. A certain acupoint can be accurately found out according to the extremely advanced modern stepping motor; 2. The specific body size of the specific user can be measured; 3. Because the body size of each body part is not necessarily the same, it can be used for different body parts of the same user, and the exact body size of a certain part can be found out; 4. A new milestone for further scientificization of acupoints or acupuncture is achieved.

The health care device for accurate position is summarized as follows. Health care device (800) includes health care body (802); rail body (804) configured on health care body (802) generally along a body part of a user; work base (848) configured on rail body (804) for building thereon an acupoint workpiece, for ensuring the acupoint workpiece to perform a healthcare or medical work onto the body of the user; and driving device (818-828) configured between rail body (804) and work base (848), for moving work base (848) along rail body (804), so work base (848) and a specific part are in an optimum mutual relative positional relationship.

In accordance with preceding health care device (800), health care device (800) further includes another rail body (804) configured on health care body (802), and two rail bodies (804) sandwich the body part; and displacement/position adjustment device (772) configured on health care body (802) and at least one rail body (804) to adjust the distance between two rail bodies (804).

In accordance with preceding health care device (800), rail body (804) has upper surface (810); near upper surface (810), paired gear slots (806) are configured on both longitudinal sides of rail body (804); a top surface of each gear slot (806) has (downward) lower gear rack (808); upper surface (810) longitudinally configures upper gear rack (812); and driving device (818-828) has upper gear (828) meshed with upper gear rack (812), and paired lower positioning gears (820) respectively meshed with paired lower gear racks (808).

In accordance with preceding health care device (800), health care device (800) further includes two carrier bodies (814, 816), each of whose proximal surfaces (862, 864) has paired positioning plates (818); each positioning plate (818) has paired lower positioning gears (820); two proximal surfaces (862, 864) are respectively fixed with gear protection sheet (824) and stepping motor (822); and each stepping motor (822) has motor shaft (826) and upper gear (828) fixed coaxially.

In accordance with preceding health care device (800), health care device (800) further includes a carrier configured between two rail bodies (804) and work base (848), wherein the carrier includes two carrier bodies (814, 816); and two carrier bodies (814, 816) have adjacent end surfaces (830) respectively having at least one pair of positioning rods (832) and at least one pair of positioning slots (834) corresponding to positioning rod (832), whereby no matter how a distance between two rail bodies (804) changes, upper surfaces (858, 860) of two carrier bodies (814, 816) are co-planar.

In accordance with preceding health care device (800), health care device (800) further includes carrier body (814, 816) carrying thereon work base (848); carrier longitudinally moving stepping motor (838) configured on carrier body (814, 816); and screw rod (840) configured between stepping motor (818) and work base (848), wherein stepping motor (838) drives to rotate/move work base (848).

In accordance with preceding health care device (800), carrier body (814, 816) has upper surface (858, 860); and health care device (800) further includes screw rod nest (842) and moving piece (846), wherein screw rod nest (842) is fixed on upper surfaces (858, 860) for accommodating screw rod (840), moving piece (846) is configured between work base (848) and screw rod (840), and stepping motor (838) determines the work position of work base (848).

In accordance with preceding health care device (800), the carrier includes two carrier bodies (814, 816) respectively having two upper surfaces (858, 860); one upper surface (860) of the two upper surfaces has sliding groove (854); and screw rod nest (842) has middle protruding piece (854) corresponding to the bottom of upper surface (860), whereby middle protruding piece (852) freely slides in groove (854).

In accordance with preceding health care device (800), health care device (800) further includes at least one ball (856) configured between middle protruding piece (852) and groove (854).

In accordance with preceding health care device (800), health care device (800) further includes acupoint workpiece connecting piece (870), wherein acupoint workpiece connecting piece (870) has first end (874) connected to fixing nut (876), and second end (880) connected to acupoint workpiece nut (882); fixing nut (876) is screwed on fixing screw bolt (850) on work base (848); and work nut (882) screws thereto an acupoint work piece.

From another aspect, health care device 800 holds an acupoint work piece (as described in FIG. 1 or the following embodiments) thereon to engage in a healthcare onto a user, wherein the user has a body part having an acupoint, and the health care device includes: a health care body 802 carrying and positioning the body part, for maintaining a first specific positional relationship with the body part; a rail body 804 configured on the health care body and extended generally along the body part; a work base 848 configured on the rail body; an acupoint work piece (as described in FIG. 1 or the following embodiments) configured on the work base to perform a health related work on the user through the acupoint; a driving device (836-846) configured between the rail body 804 and the work base 848 for moving the work base along the rail body; and a workpiece holder (as described in FIG. 1 or the following embodiments) having: a first end connected to the health care body, and a second end holding the acupoint work piece thereon, for ensuring the acupoint work piece to perform the health related work when the acupoint work piece has a second specific positional relationship with the acupoint under the first specific positional relationship.

From yet another aspect, health care device 800 includes a health care body 802 carrying and positioning a body part of a user, for maintaining a first specific positional relationship with the body part, wherein the body part has an acupoint; a rail body 804 configured on the health care body and extended generally along the body part; a work base 848 configured on the rail body to perform a health related work on the user through the acupoint; a driving device (836-846) configured between the rail body 804 and the work base 848 for moving the work base along the rail body; and a work piece holder (as described in FIG. 1 or the following embodiments) having: a first end connected to the health care body, and a second end holding an acupoint work piece (as described in FIG. 1 or the following embodiments) thereon to engage in the health related work, for ensuring the acupoint work piece to perform the health related work when the acupoint work piece has a second specific positional relationship with the acupoint under the first specific positional relationship.

It is pitiful/regrettable if such a precise positioning or displacement adjustment mechanism is only used for completing the simple healthcare as shown in FIG. 1. The advanced application of the present invention will be described below to show its actual industrial value. The physical therapy on acupoints, or acupuncture-related act at present (1) relies on professionals, such as traditional Chinese physicians or their assistants; (2) relies on the handiness of professionals (who know the correct work position) or fixed relatively large equipment (often difficult to maintain or obtain relative positions between acupoints and relevant parts of the equipment); (3) trusts the professional to have sufficient physical strength to maintain suitable relative position or contact relationship between the acupoint work piece and acupoints within a specific period; and (4) trusts that the professional is in good spirits and mood during working hours, and will not misjudge acupoints to achieve the above-mentioned task in (3). However, at least because (1) people will get tired, (2) emotion will inevitably fluctuate, (3) mind may occasionally be absent, (4) consumers may not have enough financial resources or time to keep their bodies healthy by physical therapy or traditional Chinese clinic, and/or (5) service provider, such as traditional Chinese physicians, may experience cost pressure for hiring enough assistants, we can use the aforementioned precise positioning mechanism to at least complete (1) the precise relative positional relationship between acupoint work piece and acupoint; (2) continuously and reliably maintaining the relative positional relationship in (1); (3) obtaining for the user the present precise positioning device at an extremely economical cost and using it at home; (4) when the user's illness or discomfort is relieved by the present invention, s/he no longer needs to go to the hospital for treatment, which saves the burden on the national health insurance by at least one third (taking Taiwan as an example, it is over NT$200 billion); and/or (5) the resources can be transferred to measures benefiting country and people under rational national policies.

Figure 8:
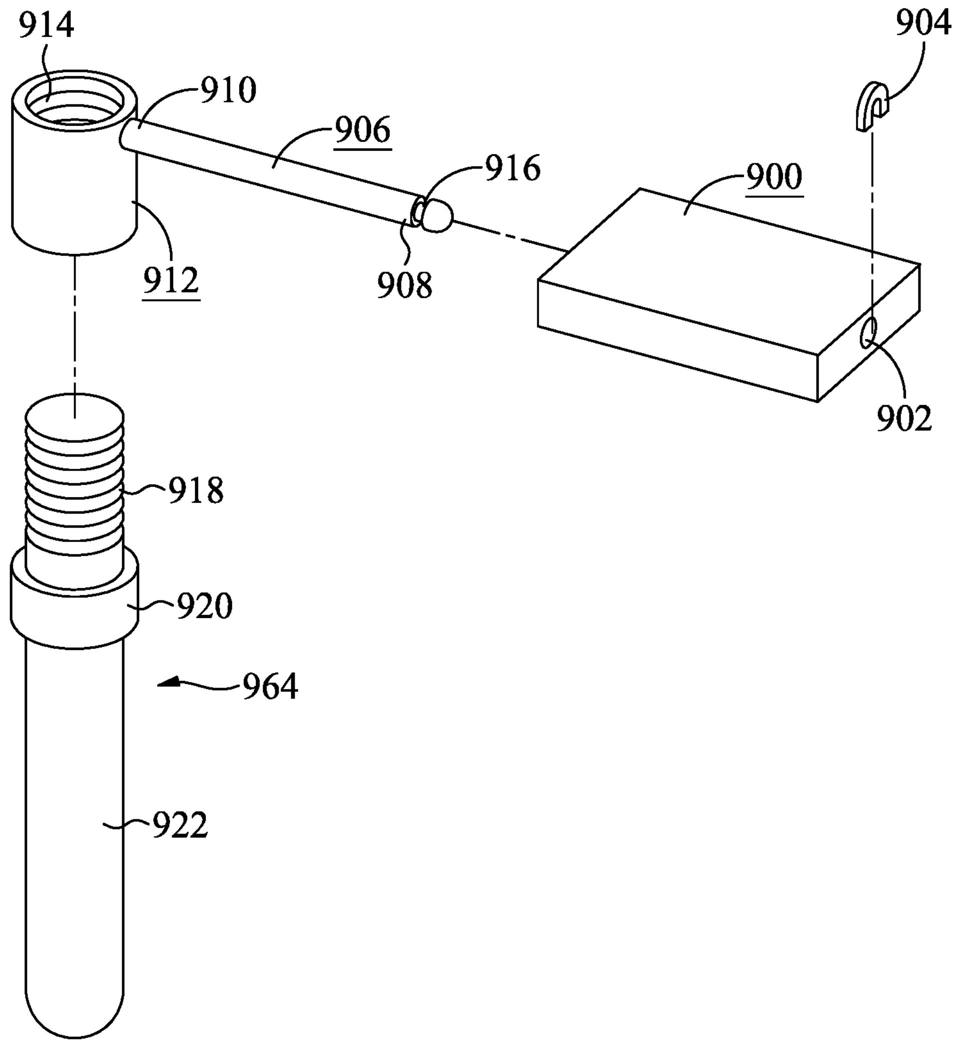
FIG. 8 is the first embodiment of the work piece assembly.

The ideal disclosures may be touching; but it must be implemented before gaining trust from others. According to Paragraphs 20 to 29 of the present specification, it can be known/inferred that there must be various acupoint work pieces on the market, for examples, (A) the microwave needle usually has a focal work point; (B) the radiator instrument often has a planar or curved output end; (C) the magnet has a specific work plane; (D) one end of the magnetic massager is a single relatively large ball, while the other end includes three relatively small balls. Please refer to FIG. 8 showing a specific embodiment of a workpiece assembly, including work base 900 configured on the aforementioned health care device, being equivalent to work base 848, and having longitudinal through hole 902. In this embodiment, work piece holder 906 has first end 908 configuring thereon annular groove 916, and second end 910 configuring thereon connector 912 having internal thread 914. Work piece 964 has first end 918 screwed to internal thread 914, and second end 922 being an acupoint workpiece for performing the health care work onto a user's acupoint, and first and second ends 918, 922 are connected by connecting piece 920.

When using, first end 908 of work piece holder 906 passes through through hole 902, and C-clamp 904 is fastened to annular groove 916 to position work piece 964. If the acupoint work piece, i.e., second end 922 of work piece, is the microwave or radiation in the preceding paragraph, it is only necessary to determine or fix the relative positional relationship between acupoint work piece 922 and the acupoint; but if it is a magnet or magnetic massager, some pressure must be applied on the acupoint. To achieve the purpose of applying pressure, because connector 912 is cylindrical and first end 918 is columnar, their screwing depth can determine the work pressure applied to the acupoint, to adjust the work pressure of acupoint work piece 922. Please refer to FIG. 8A, the first end of work piece holder 930 has threaded section 932 and annular groove 934, and threaded section 932 is to tightly fit with threaded hole 938 on work base 936 at a specific angle. In this way, the work angle of acupoint work piece 922 with respect to the acupoint can be adjusted.

Figure 8B:
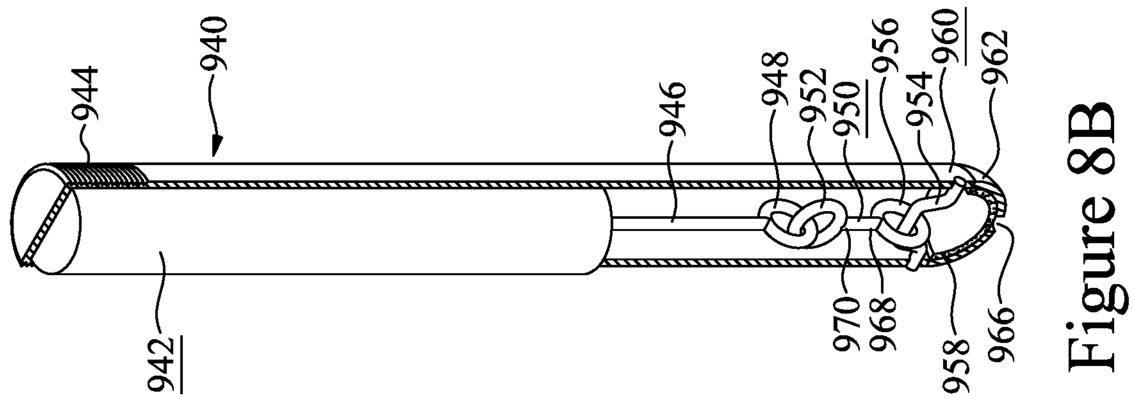
FIG. 8B is an embodiment of the acupoint work piece.
Figure 8A:
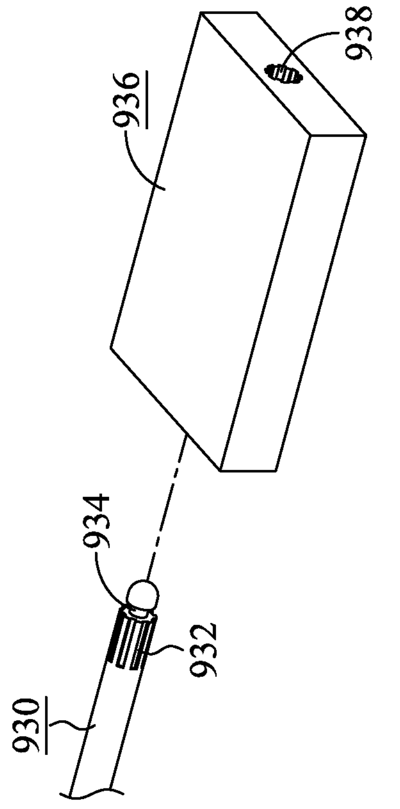
FIG. 8A is a schematic diagram of the third embodiment of the connecting piece of the acupoint work piece.

Please refer to FIG. 8B showing an embodiment of acupoint work piece 940 in the present invention. Acupoint work piece 940 is basically slender pneumatic cylinder 942 having threaded end 944 connected to a work piece holder and work end 960. Work bottom 962 adjacent to work end 960 has rotatably configured crankshaft 954, point opening 966, rubber pad 958 configured among crankshaft 954, point opening 966 and work bottom 962, main connecting piece 950 having first end 968 and second end 970 fixing thereon ring piece 952, upper connecting ring 948 fixed on piston rod 946 of pneumatic cylinder 942 and interlocked with ring piece 952, and work ring 956 fixed on first end 968 and movably buckled on the crank part of crankshaft 954. When using, crankshaft 954 is driven to rotate downward through upper connecting ring 948, main connecting piece 950 and work ring 956 when piston rod 946 moves down; and crankshaft 954 is reversely driven to rotate upward through the same components when the piston rod moves up. At this time, point opening 966 is in contact with an acupoint, and work ring 956 performs the massage operation on the user's acupoint through rubber pad 958 by the crankshaft's rotation. According to the acupoint's characteristics, the shape of point opening 966 can be determined, such as a small round area, or an arc slot corresponding to the working track of work ring 956.

Different embodiments disclosed in different stages or embodiments of the present application can be mutually replaceable, which should be noted. This paragraph summarizes the main requirements related to the acupoint work piece. Specifically, a health care device includes a health care body; work base (900) configured on the health care body for health-caring a user having an acupoint; a moving device configured between work base (900) and the health care body to move a position of work base (900) corresponding to the health care body; acupoint work piece (922) performing a health-care work onto the user through the acupoint; and work piece holder (906) for connecting acupoint work piece (922) to work base (900), so that acupoint work piece (922) can continue performing the health-care work under a specific relationship position relative to work base (900) or the acupoint.

In accordance with preceding health care device, work piece holder (906) has first end 908 configured on work base (900), and second end (910) configuring thereon connector (912) having internal thread (914); and work piece (964) has first end (918) screwed to internal thread (914), and second end (922) for performing the health-care work onto a user's acupoint or part to be treated.

In accordance with preceding health care device, connector (912) is cylindrical, and first end (918) of work piece (964) is columnar, whereby a screwed depth or extent therebetween can determine a work pressure of the acupoint or part to be treated exerted by second end (922).

In accordance with preceding health care device, second end (922) of work piece (964) is an acupoint work piece.

In accordance with preceding health care device, work base (900) has longitudinal through hole (902); first end (908) of work piece holder (906) has annular groove (916); and after first end (908) passes through through hole (902), C-clamp (904) is fastened to annular groove (916) to position work piece (964).

In accordance with preceding health care device, work base (900) has longitudinal through hole (902) having an end threaded hole (938); and first end (908) of work piece holder (906) has a threaded section (932), whereby we can adjust a work angle acupoint work piece 922 treats the acupoint or part to be healthcared through press-fit of threaded section (932) with threaded hole (938) under a specific angle.

From another aspect, a health care device holds an acupoint work piece thereon to engage in a health-care onto a user, wherein the user has a body part having an acupoint, and the health care device includes: a health care body carrying the body part thereon, for maintaining a first specific positional relationship with the body part; work base 900, 936 configured on the health care body; an acupoint work piece configured on the work base to perform a health related work on the user through the acupoint; moving device (e.g, 836-846, 972, 1040) configured between the work base and the health care body for determining an orientation of the acupoint work piece relative to the health care body; and a work piece holder (e.g., 906, 930) having: a first end connected to the work base, and a second end holding the acupoint work piece thereon, for ensuring the acupoint work piece to perform the health related work when the acupoint work piece has a second specific positional relationship with the acupoint under the first specific positional relationship.

From yet another aspect, a health care device includes a health care body carrying a body part of a user thereon, for maintaining a first specific positional relationship with the body part, wherein the body part has an acupoint; work base

900, 936 configured on the health care body to perform a health related work on the user through the acupoint; moving device (e.g., 836-846, 972, 1040) configured between the work base and the health care body for securing an orientation of the work base relative to the health care body on the health care body; and work piece holder (e.g., 906, 930) having: a first end connected to the work base, and a second end holding an acupoint work piece thereon to engage in the health related work, for ensuring the acupoint work piece to perform the health related work when the acupoint work piece has a second specific positional relationship with the acupoint under the first specific positional relationship.

A work piece (940) for health care is configured on a health care device to perform a health-care work on a user's acupoint, wherein the health care device has a work base (900), and the acupoint work piece (940) includes work body (942) having first end (944) and second end (960), wherein first end (944) is connected to work base (900); and health care medium (922, 956) configured on second end (960) to perform the health-care work.

In accordance with preceding work piece, the work body is slender pneumatic cylinder (942) having piston rod (946).

In accordance with preceding work piece, work end (960) further includes crankshaft (954) rotatably configured on work end (960); point opening (966); rubber pad (958) configured between crankshaft (954) and point opening (966); and main connecting piece (950) connected between piston rod (946) and crankshaft (954), so that piston rod (954) drives crankshaft (954) to perform the health-care work.

In accordance with preceding work piece, main connecting piece (950) has first end (968) and second end (970); second end (970) fixes therewith ring piece (952); work piece (940) further includes upper connecting ring (948) connected between piston rod (946) and ring piece (952); and work ring (956) is fixed on first end (968), and movably buckled to crankshaft (954).

In accordance with preceding work piece, work ring (956) performs massage operation on body part or acupoint through rubber pad (958).

In accordance with preceding work piece, point opening (966) is a round opening, or an arc slot corresponding to working track of work ring (956).

In accordance with preceding work piece, the first end has a thread.

In accordance with preceding work piece, a working medium of the health care medium is a microwave, a millimeter wave, a radiation heat, a magnetism, a frequency signal, a microcurrent or a wormwood heat.

From another aspect, healthcare acupoint work piece (942, 964) is configured on health care body (e.g., 502, 562, 582) to perform a health care work on an acupoint in a user's body part, wherein the health care body has work base (900, 934) carrying and positioning the body part for maintaining a first specific positional relationship with the body part, and the acupoint work piece includes: work body (922, 942) having first end (944) and second end (960), wherein the first end is connected to the work base; and a health care medium (922; 946-958) configured on the second end, for ensuring the acupoint work piece to perform the health care work when the acupoint work piece has a second specific positional relationship with the acupoint under the first specific positional relationship.

From yet another aspect, acupoint work piece (942, 964) for health care includes work body (922, 942) configured on health care body (e.g., 502, 562, 582), wherein the health care body carries and positions a body part of a user, the health care body maintains a first specific positional relationship with the body part having an acupoint, the health care body has work base (900, 934) to perform a health care work to user through the acupoint, and the work body includes: first end (944) connected to the work base; second end (960); and health care medium (922; 946-958) configured on the second end, for ensuring the acupoint work piece to perform the health care work when the acupoint work piece has a second specific positional relationship with the acupoint under the first specific positional relationship.

Figure 8C:
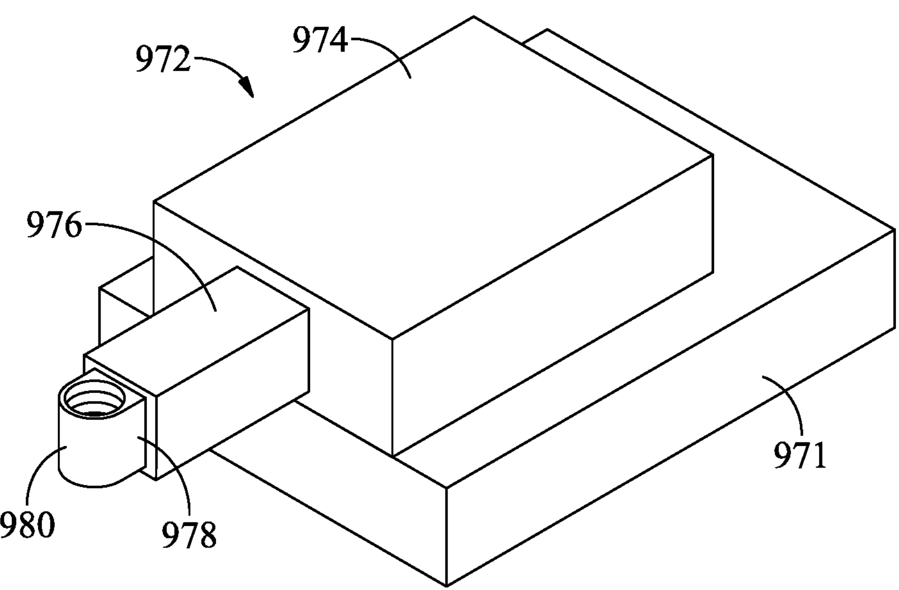
FIG. 8C is the second embodiment of the work piece assembly.
Figure 8D:
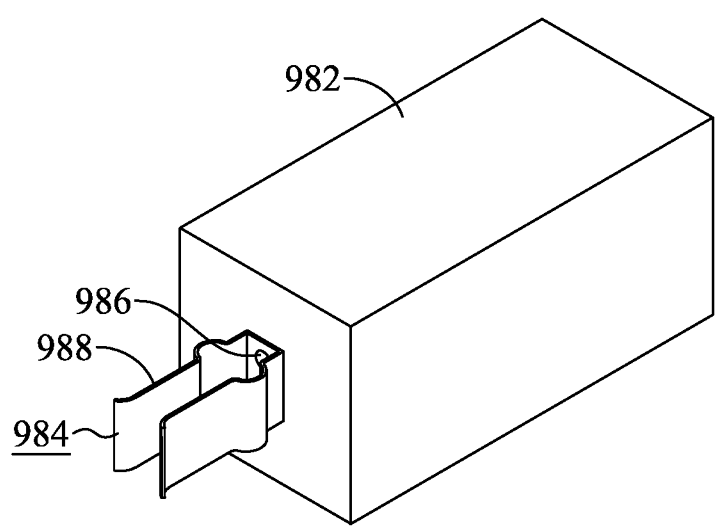
FIG. 8D is another embodiment of the work piece holder.

It is not difficult under the current technology if the accuracy of adjusting the working angle of the acupoint work piece is to be increased. Please refer to the second embodiment of the work piece assembly in FIG. 8C showing work base 971 corresponding to work base 848. Work base 971 configures thereon angle controller 972 including angle control assembly 974 and work piece supporter 976. Supporter 976 fixes thereon threaded barrel 980 through fixing piece 978, whereby supporter 976 is controlled by angle control assembly 974 to secure for threaded barrel 980 a specific angle relative to work base 971 or the acupoint. FIG. 8D shows that highly resilient acupoint workpiece jaw 984 is fixed on workpiece supporter 982 by screw or rivet 986, and acupoint workpiece jaw 984 has paired holding parts 988 for firmly holding an acupoint work piece therebetween.

This paragraph summarizes the acupoint work piece having the accurate adjustment of the working angle. Specifically, a health care device includes a health care body; work base (971) configured on the health care body for health-caring a user having an acupoint; an acupoint work piece performing a health-care work onto the user through the acupoint; and angle controller (972) for connecting the acupoint work piece to work base (971), so that the acupoint work piece can continue performing the health-care work under a specific angle relative to work base (971) or the acupoint.

In accordance with preceding health care device, the health care device further includes a moving device configured between work base (971) and the health care body to move a position of work base (971) relative to the health care body.

In accordance with preceding health care device, the angle controller includes angle control assembly (974) and workpiece supporter (976) connected thereto to obtain a specific work angle of workpiece supporter (976) with respect to work base (971) or the acupoint.

In accordance with preceding health care device, workpiece supporter (976) is highly resilient acupoint workpiece jaw (984) fixed on workpiece supporter (982) by rivet or screw (986).

In accordance with preceding health care device, workpiece jaw (984) has paired resilient holding parts (988) for firmly holding an acupoint work piece therebetween.

One should not consider that the disclosure of the technology related to the acupoint health care of the present invention has been completed with the aforementioned work pieces and health care devices. Specifically, although the last embodiment above can solve the problem of precise angle control, taking the Gallbaldder Meridian as an example, its distribution path of some acupoints is rather irregular. For example, three acupoints, Yanglingquan (International Code GB34, mainly treating knee pain, sciatica, hemiplegia, lower limb numbness and cholecystitis), Yangjiao (International Code GB35, mainly treating chest/flank distention, chest tightness, pharyngitis, knee pain, leg/foot atrophy/weakness, facial swelling) and Waiqiu (International Code GB36, mainly treating headache, neck pain, hepatitis, lower limb paralysis, poisonous stasis from a vicious dog) cross front side, midline and back side of the yang surface of the shank. Even the positioning problem can be solved based on the above, it is not the best policy to invoke "a cannon" for only a few acupoints. Therefore, if there is a design that can allow the acupoint work piece to be optionally tilted relative to the work base, the usability or satisfaction of the design will be greatly improved.

Figure 9:
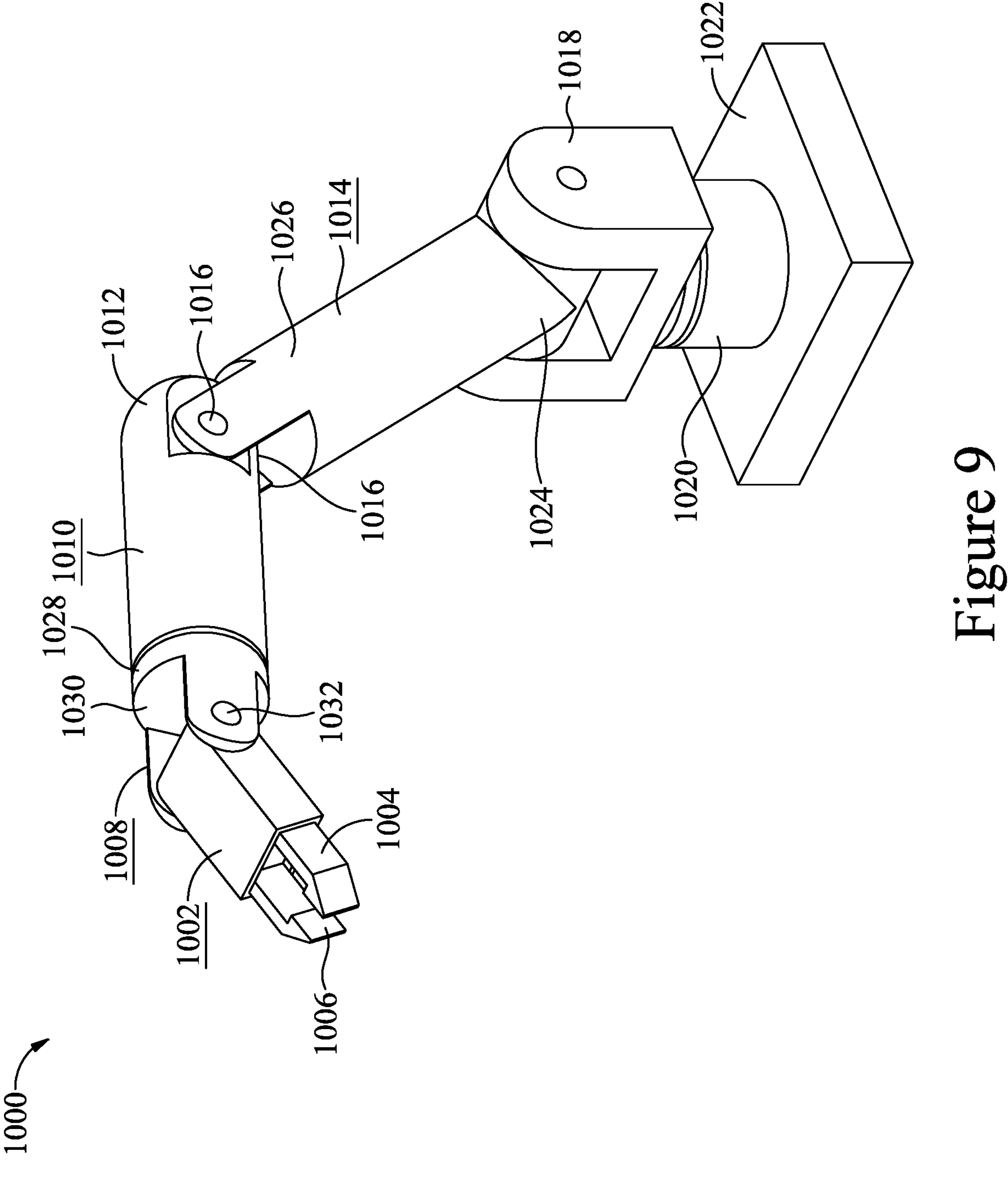
FIG. 9 is an embodiment of a workpiece assembly with a robotic arm.

To the aforementioned purpose, please refer to FIG. 9 showing an embodiment of work piece assembly 1000 matching with a robotic arm. Modern technology is often amazing, where robots or robotic arms can often work with precision. Work assembly 1000 includes work base 1022 of FIG. 9 corresponding to work base 848 of FIG. 7, and work platform 1020 fixed thereon. Work platform 1020 carries rotating platform 1018 with a precisely controlled rotation angle, and rotating platform 1018 is connected to first end 1024 of connecting base 1014 with a precisely controlled pivot angle. First end 1012 of extension base 1010 is connected to rotating shaft 1016 of second end 1026 of connecting base 1014 with a precisely controlled pivot angle, and second end 1028 of extension base 1010 is fixed to first end 1030 of rotating head 1008 having second end 1032 precisely rotatably fixing thereon electric chuck 1002 having two jaws 1004 respectively having paired holding surfaces 1006 for holding the preceding acupoint work piece therebetween. Having these four rotations, it can be immediately imagined that: (1) some displacement designs or requirements in FIG. 7 can be replaced; (2) if this work piece assembly 1000 is combined with lower limb health care body 660 in FIG. 5, the irregular acupoints on the Gallbladder Meridian are very easy to be found; (3) with respect to the reference point or positioning point of the acupoint work piece on the health care body, the planar distance, vertical height and relative angle of the acupoint work piece relative to the specific part or acupoint of the body to be health cared can be fully controlled (through the abovementioned four rotation movements, which can be accurately calculated and obtained); and (4) therefore, the medical-grade acts can be expected using the acupoint work piece. In this regard, the principle is detailed in the next paragraph.

The body inch standards of hand and leg are mentioned above. If following standards of the chest and abdomen are realized, with the structure disclosed earlier, after finding the reference acupoint, can the specific body inch of a person be found and calculated? It also helps to find other acupoints automatically by the computer, and thus the misidentification of acupoints caused by the fatigue of the doctors or humans can be avoided, which will be detailed later. (1) The standard of chest vertical body inch: 6.8 body inches from Tiantu acupoing (International Code CV22) to Shanzhong acupoint (International Code CV17, the middle of two nipples); (2) the standard of upper abdomen vertical body inch: 8 body inches from branch bone (xiphoid process) to navel (International Code CV8, Shenque); (3) the standard of lower abdomen vertical body inch: 5 body inches from navel (International Code CV8) to Qugu (International Code CV2); (4) the standard of lateral abdomen vertical body inch: 9 body inches from Zhangmen (International Code LR13) to Huantiao (International Code GB30); and (5) the standard of trunk horizontal body inch: 8 body inches between two nipples. Therefore, after the Shanzhong acupoint is obtained, 1.6 body inches therebeneath is Zhongting acupoint (International Code CV16). In details, according to the preceding robotic arm device (components 1002-1020), (1) the first rotation mechanism (between components 1018 and 1020) can determine the angular relationship between the work base or the health care body and an acupoint; (2) the second pivoting mechanism (between components 1018 and 1014) can at least determine the linear distance relationship between the work base or the health care body and an acupoint alone or together with other mechanisms; (3) the third pivoting mechanism (between components 1010 and 1014) can at least determine the height relationship between the work base or the health care body and an acupoint alone or together with other mechanisms; (4) the fourth rotation mechanism (between components 1010 and 1002) can determine the angular relationship between the acupoint work piece and an acupoint; and (5) all these relationships can be easily and automatically calculated by the computer to obtain in which distance and orientation (actually representing an acupoint position) of the robotic arm device to enable the acupoint work piece to perform the health care or therapeutical work to the user through the acupoint under which specific angle. Therefore, although oblique acupuncturing is often necessary for acupoints on the head/face, it is no longer a trouble because the control/adjustment of the relative inclination angle between the acupoint work piece and the work base has been made possible by the aforementioned mechanism. Certainly, it has been described that the robotic arm device can be directly configured on a health care body, or configured on a work base that has been configured on the health care body.

The main requirements related to work piece assembly 1000 are summarized as follows. Specifically, a health care device includes a health care body for health-caring a user having an acupoint; work platform (1020) configured on the health care body; an acupoint work piece performing a health-care work onto the user through the acupoint; and robotic arm device (component assembly 1002-1020) connected to the work platform (1020) for holding the acupoint work piece, so that the acupoint work piece can perform the health-care work under a specific relationship position relative to work platform (1020) or the acupoint.

In accordance with preceding health care device, the health care device further includes work base (1022) configured between the health care body and work platform (1020); and a moving device (FIG. 7) configured between work base (1022) and the health care body.

In accordance with preceding health care device, the health care device further includes rotating platform (1018) rotatably carried on work platform (1020).

In accordance with preceding health care device, the health care device further includes connecting base (1014) pivotally connected on the rotating platform (1018).

In accordance with preceding health care device, the health care device further includes extension base (1010) having first end (1012) and pivotally connected on connecting base (1014).

In accordance with preceding health care device, the robotic arm device includes rotating head (1008) rotatably fixing precisely thereon electric chuck (1002) having two jaws (1004) respectively having paired holding surfaces (1006) to hold therebetween the acupoint work piece.

It can be imagined that since the preceding health care device is precise enough, it is predictable it can be applied to the needle insertion of acupuncture. Because the control and adjustment of the angle can be completed by the preceding embodiments, it is easily understood according to FIG. 9A that the automatic needle insertion of acupuncture is feasible. Maybe people may question that as an acupuncture act is of a human nature, why does the present invention try to do it mechanically? This question is actually contrary to the appeal for "scientificization of traditional Chinese medicine (TCM)", not to mention that the scientific spirit is a nature of TCM. First, the "Encyclopedia of Acupuncture/Moxibustion" points out: "Needle withdrawal should happen slowly, or it will cause injuries if rapid", which means that the needle should be withdrawn slowly, which can wonderfully be performed by a machine which will follow instructions without mood or emotional effects. Second, according to the Yellow Emperor Neijing, Ci-Yao Chapter, which records "There are floating and sunk states, while the acupuncture depth is shallow or deep. Each case has its own curing rationale, from which deviation should be avoided. An excessive extent will cause an internal hurt while an insufficiency will produce a superficial block which in turn invokes an evil qi. An improper depth will cause a big trouble internally hurting the 5 organs to develop an ensuing serious disease", each acupoint for a certain disease has its appropriate depth. By the same token, isn't it the best policy to determine the appropriate depth of needle insertion by a machine to eliminate the interference of human factors?

Figure 9A:
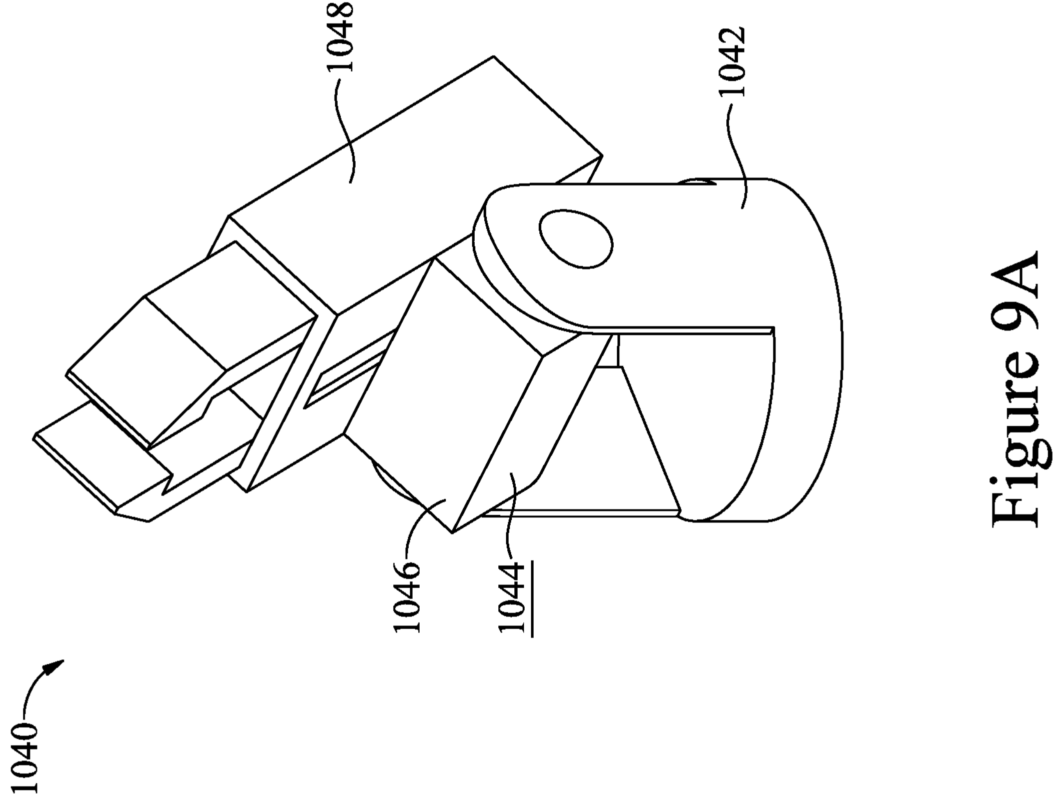
FIG. 9A is an embodiment of an automatic acupoint workpiece.

FIG. 9A shows an embodiment of automatic needle inserting acupoint work piece 1040 including rotating head 1042 similar to rotating head 1008 of FIG. 9 and automatic needle inserting device 1044. Automatic needle inserting device 1044 includes electric holder 1048 (or a non-electric holder) for holding an acupoint work device, and needle inserting mechanism 1046 capable of longitudinally moving electric holder 1048 and pivotably configured on rotating head 1042. Needle inserting mechanism 1046 enables the acupoint work device to insert the needle orderly or controls the needle inserting speed by a stepless speed motor. As this technical task can be easily achieved by the skilled person in the art, which will not be detailed here. Certainly, when it is necessary to significantly drain the evil qi, the needle hole must be widened. At this time, the needle inserting parameters are not limited to the speed, but include the front, back, left and right polarizations. In view of above technical disclosures, these technical tasks should already be easily realizable by the skilled in the art, which will not be detailed here.

The main requirements related to automatic needle inserting acupoint work piece 1040 are summarized as follows. Specifically, a health care device includes a health care body for health-caring a user having an acupoint; an acupoint work piece performing an acupuncture work onto the user through the acupoint; a robotic arm device (component assembly 1002-1020) configured on the health care body for holding the acupoint work piece, so that the acupoint work piece can perform the acupuncture work under a specific relationship position relative to the health care body or the acupoint; and needle inserting mechanism (1046) configured between the acupoint work piece and the robotic arm device, and enabling the acupoint work piece to perform the acupuncture work on the user with a specific control parameter.

In accordance with the preceding automatic needle inserting acupoint work piece, the specific control parameter is a speed control parameter.

In accordance with the preceding automatic needle inserting acupoint work piece, the specific control parameter is a polarization parameter.

In accordance with the preceding automatic needle inserting acupoint work piece, the automatic needle inserting acupoint work piece further includes holder (1048) for holding the acupoint work piece.

In accordance with the preceding automatic needle inserting acupoint work piece, the automatic needle inserting acupoint work piece further includes needle inserting mechanism (1046) for longitudinally moving holder (1048).

In accordance with the preceding automatic needle inserting acupoint work piece, the automatic needle inserting acupoint work piece further includes rotating head (1042) for rotatably configuring needle inserting mechanism (1046) on the robotic arm device.

From another aspect, health care device 1000 holds an acupoint work piece thereon to engage in a health-care onto a user, wherein the user has a body part having an acupoint, and the health care device includes: health care body (e.g., 502, 562, 582) carrying and positioning the body part, for maintaining a first specific positional relationship with the body part; work platform (1020) configured on the health care body; and a robotic arm device (1002-1018) connected to the work platform for holding the acupoint work piece, for ensuring the acupoint work piece to perform the health-care work when the acupoint work piece has a second specific positional relationship with the acupoint under the first specific positional relationship.

From yet another aspect, health care device (1000) includes a health care body (e.g., 502, 562, 582) carrying and positioning a body part of a use, for maintaining a first specific positional relationship with the body part to engage in a health-care work onto the user, wherein the body part has an acupoint; work platform (1020) configured on the health care body; and a robotic arm device (1002-1018) connected to the work platform for holding the acupoint work piece, for ensuring the acupoint work piece to perform the health-care work when the acupoint work piece has a second specific positional relationship with the acupoint under the first specific positional relationship.

Figure 10:
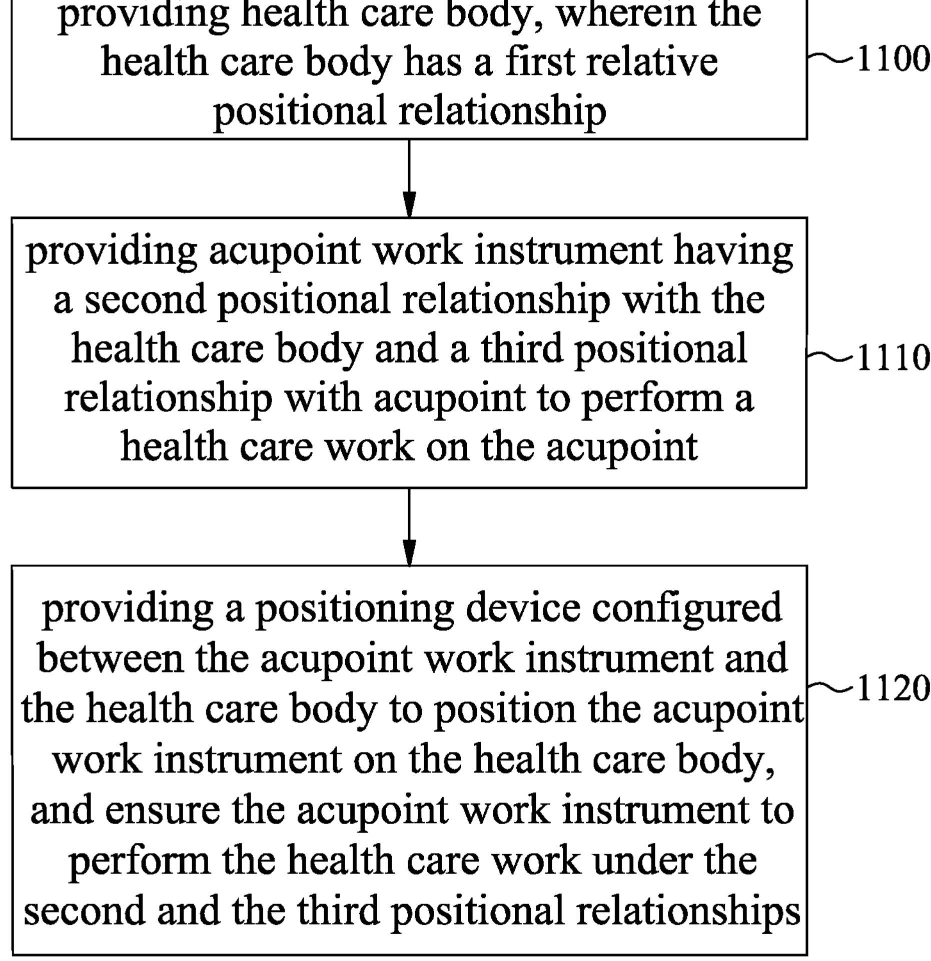
FIG. 10 is a first embodiment of the health care methods of the present invention.
Figure 10A:
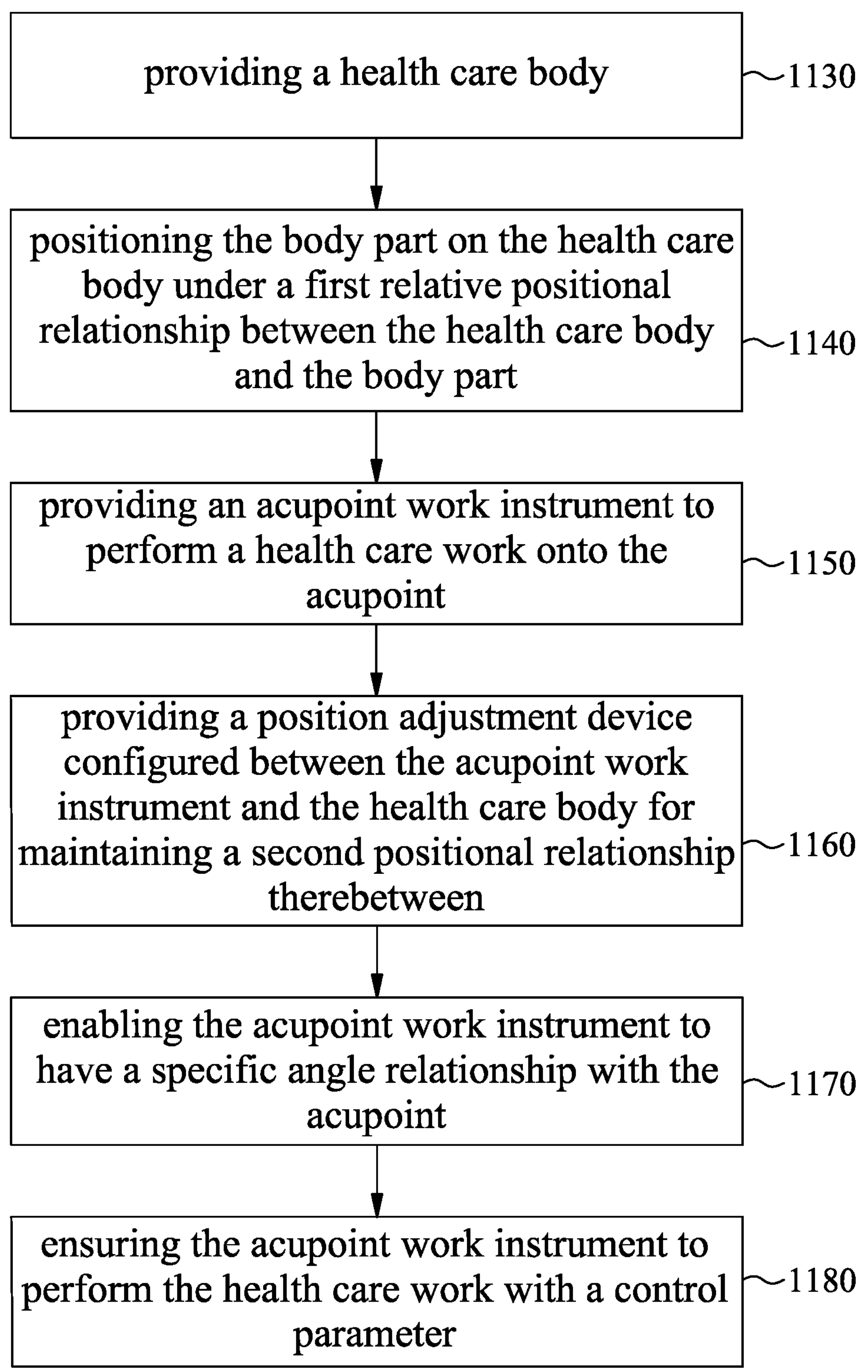
FIG. 10A is a second embodiment of the health care methods of the present invention.

Descriptions on relevant hardware of the present invention have come to an end. It can be found that each paragraph is directed to adjust the "qi field" to recuperate the body instantly when there is an initial disease omen, for a longeval and healthy life as disclosed in the Yellow Emperor Neijing Suwen, Yijing Qi-Change Chapter, "while nearing being alive away from death, the living seedling is growing." The present invention's gist is summarized with the FIG. 10 flowchart as follows: providing health care body 1100, wherein the health care body has a first relative positional relationship with a user's body part having an acupoint; providing acupoint work piece having a second positional relationship with the health care body and a third positional relationship with the acupoint to perform a health care work on the user through the acupoint (1110); and providing a positioning device configured between the acupoint work piece and the health care body to position the acupoint work piece on the health care body, and ensure the acupoint work instrument to perform the health care work under the second and the third positional relationships (1120).

From another aspect, the present invention is a health care method for health-caring a user, wherein the user has a body part having an acupoint, including: providing a health care body (1130); positioning the body part on the health care body under a first relative positional relationship between the health care body and the body part (1140); providing an acupoint work piece to perform a health care work onto the user through the acupoint (1150); providing a position adjustment device configured between the acupoint work piece and the health care body for maintaining a second positional relationship therebetween (1160); and ensuring the acupoint work piece to perform the health care work with a control parameter (1180).

In accordance with the preceding health care method, the first relative positional relationship is to enable the body part to keep the relative positional relationship with the health care body in a specific posture.

In accordance with the preceding health care method, the health care method further includes a step of enabling the acupoint work piece to have a specific angle relationship with the acupoint (1170) between the steps of providing the position adjustment device (1160) and ensuring the acupoint work piece to perform the health care work with the control parameter (1180).

In accordance with the preceding health care method, the second relative positional relationship is to enable the acupoing work piece to keep the relative positional relationship with the health care body in at least one of a specific distance, direction and height.

In accordance with the preceding health care method, the control parameter is a work mode for the acupoing work piece to perform the health care work.

In accordance with the preceding health care method, the work mode is that the acupoint work piece and the acupoint remain mutually still.

In accordance with the preceding health care method, the work mode is that the acupoint work piece and the acupoint keep therebetween a specific contact relationship.

In accordance with the preceding health care method, the work mode is that the acupoint work piece performs a massage operation onto the user through the acupoint.

In accordance with the preceding health care method, the work mode is that the acupoint work piece inserts into or draws out of the acupoint at a specific speed.

From another aspect, a method using an acupoint work piece to perform a health care work on a user, wherein the user has a body part having an acupoint, includes: providing a health care body for carrying the body part 1110; positioning the body part on the health care body so that the health care body and the body part have a first relative positional relationship therebetween 1120; and providing a position adjustment device for maintaining a second positional relationship between the acupoint work piece and the health care body, or the acupoint work piece and the acupoint to ensure the acupoint work piece to perform the health care work with a control parameter (1160).

From yet another aspect, a health care method includes: providing a health care body for health-caring a user (1110), wherein the user has a body part having an acupoint, and the health care body carries the body part, so that a health care effect is performed to the user when the health care body holds an acupoint work piece thereon; positioning the body part on the health care body so that the health care body and the body part have a first relative positional relationship therebetween 1120; and providing a position adjustment device for maintaining a second positional relationship between the health care body and the acupoint work piece, or the acupoint work piece and the acupoint to ensure the acupoint work piece to perform the health care work with a control parameter (1160).

If the preceding methods involve medical acts, they may be classified as disease treating methods, which may be patent-ineligible concepts in Taiwan and China. When it is only related to a health care act, it may not relate to a treating method.

The disclosure of the present invention may be well-plotted, but must have an end. The last highlight or ideal of the present invention is hereby proposed: in order to seek the health/happiness of all mankind to realize the touching ideals disclosed previously, it is necessary to enable every family/person to possess the software/hardware of the present invention even if their financial resources are relatively limited. Except waiting for the present invention to be commercialized in large scale to reduce costs, it is clear good hardware alone should be insufficient, and success can be alleged in the end only when every one may enjoy or receive physiotherapy or medical services like those provided by the reincarnation of Hua Tuo or Bian Que. AlphaGo developed by Deep Mind company defeated the world's chess king, and it simply relies on accumulating all the world's experiences in the same brain and then making decisions. For another example, if an aircraft has an accident, it must be reported to the manufacturer to repair the design to prevent the same accident in future. If this spirit is upheld, and the previous wisdom since ancient times will first be collected and then organized by the outstanding people today, followed by the continuous true feedback on therapeutic effects of the acupoint therapy from the general public, why should it be worried about that Hua Tuo or Bian Que cannot reincarnate?

Figure 10B:
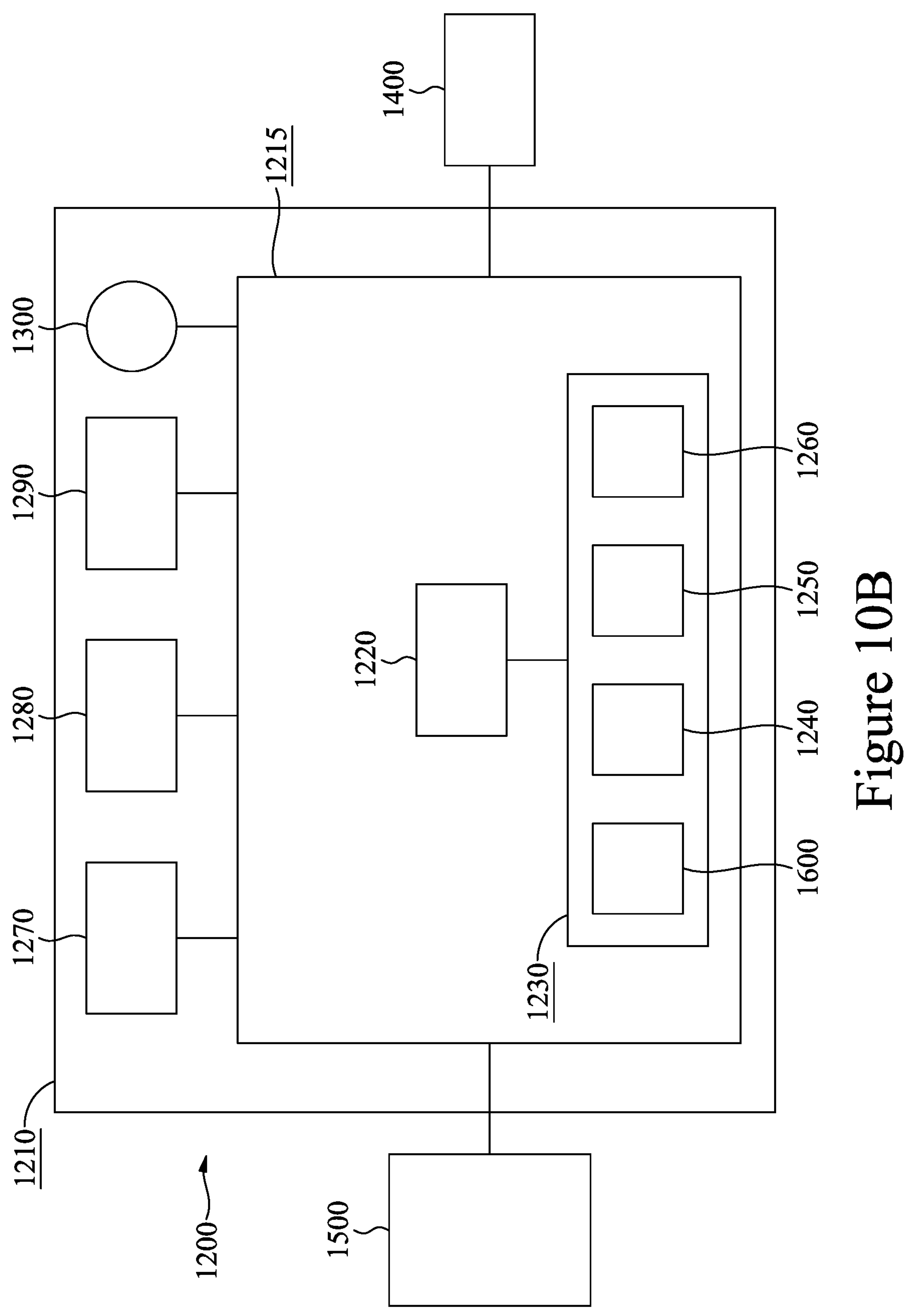
FIG. 10B is an embodiment of the health care system of the present invention.

For purposes of the preceding paragraph, please refer to FIG. 10B showing an embodiment of health care system 1200 of the present invention including health care body 1210 having micro computer 1215 connected to cloud database 1400 and service center 1500 through an internet. Micro computer 1215 includes/configures central processing unit 1220, memory 1230, screen 1270, keyboard/mouse 1280, microphone 1290, and lens 1300. Since their mutual connection and configuration are common technologies, it will not be detailed here. It also makes no difference whether screen 1270 is touch type or non-touch type. Memory 1230 can store the application software required for interaction between the user and cloud database 1400 and service center 1500, such as symptom treatment module 1240 for clicking or entering the current discomfort symptoms, to retrieve from cloud database 1400 which treatment scheme or acupoint(s) to receive the health care work. It can also be personal health care history record module 1250 recording a user's personal health care history. Certainly, it can also be feedback/report module 1260 for the feedback/report of the user's satisfaction or problems encountered in use after the health care work suggested by cloud database 1400. Modules 1240, 1250, 1260 and other modules related to health care work can be individual or separate modules, or submodules integrated in the same program.

Through cloud database 1400, the user can search and confirm the symptoms or their treatment methods by screen 1270 and/or keyboard/mouse 1280. Through service center 1500, the user can consult, inquire about the symptom and/or confirm the act related to acupuncture or moxibustion by microphone 1290/lens 1300. Certainly, health care system 1200 must be confirmed by the national health authority as a doctor or qualified to perform a medical practice before performing needle injection. As mentioned, through collection of acupuncture or moxibustion information available so far, and research, confirmation, deep learning and constant user feedback, cloud database 1400 cooperated with service center 1500 stationed with traditional Chinese physicians should be able to provide extremely amazing health care or medical effects. As there is no ending for learning, the present invention's disclosure is just a good start, and more efforts are still needed for Hua Tuo or Bian Que to be truly reincarnated. Control module 1600 stores, with supports from central processing unit 1220, coordinates the health care device or the health care body previously disclosed to perform various relevant health care works.

The first chapter, Nine Needles and Twelve Originals, of Lingshu of the Yellow Emperor's Neijing starts with "The Yellow Emperor asked Qibo: I have myriad thousands of people, and collect therefrom rents and taxes; I want to use micro-needles to smoothen their meridians, adjust their blood/qi, and flourish the meeting points of incoming and outgoing paths without drugs or medical appliances. What I want is that can be passed on to future generations, must be clear standards, will not be overturned, will be everlasting, is easy to use but difficult to forget, is classical but separated into chapters, distinguishes inner and outer symptoms, systemizes with beginning and ending, and is concretized into acupuncture scriptures. Is this something possible?" As the acupuncture effects have been worldwide confirmed, the present invention is to ignite the strong hope of welcoming incarnation of Hua Tuo or Bian Que. Through the joint participation of all human beings, we may welcome the return of Hua Tuo or Bian Que as soon as possible.

Health care system (1200) is summarized as follows. Specifically, it includes health care body (1210) for health-caring a user, wherein the user has a body part having an acupoint; positioning medium (524, 680, 714, 804) configured on health care body (1210) and securing a positional relationship between the body part and the health care body; an acupoint work piece configured on the health care body and performing a health care work onto the user through the acupoint; and computer device (1215) configured on the health care body and controlling and/or monitoring the acupoint work piece to perform the health care work.

In accordance with preceding health care system, the health care system further includes cloud database (1400) connected to computer device (1215) through an internet, and allowing the user to access therefrom knowledge and healthcare scheme or medical treatment related to acupuncture/moxibustion.

In accordance with preceding health care system, computer device (1215) further includes symptom treatment module 1240 allowing the user to click or enter a current discomfort symptom, by which cloud database (1400) provides a specific treatment scheme or a specific acupoint to receive the health care work.

In accordance with preceding health care system, computer device (1215) further includes feedback/report module (1260) allowing the user to feedback/report user satisfaction or problems encountered in use to cloud database (1400) after the health care work on a specific acupoint suggested by cloud database (1400).

In accordance with preceding health care system, computer device (1215) further includes screen (1270) and keyboard/mouse (1280) allowing the user to search and confirm a symptom or its treatment method through cloud database (1400).

In accordance with preceding health care system, the health care system further includes service center (1500) connected to computer device (1215) through an internet, and providing the user with a consultation related to acupuncture/moxibustion, or a confirmation of the user's own choice of a medical-level act.

In accordance with preceding health care system, computer device (1215) further includes microphone (1290) and lens (1300) for a consultation by, an inquisition on the symptom of, or a confirmation from the user of an act related to acupuncture or moxibustion via service center (1500).

In accordance with preceding health care system, computer device (1215) includes screen (1270) of a touch type or non-touch type.

In accordance with preceding health care system, computer device (1215) further includes personal health care history record module (1250) recording a user's personal health care history.

In accordance with preceding health care system, computer device (1215) further includes control module (1600) coordinating the health care body and/or the acupoint work piece to perform the health care work.

In accordance with preceding health care system, the health care system further includes a position adjustment device configured between health care body (1140) and the acupoint work piece, so that the acupoint work piece and health care body (1140) have a relative positional relationship.

From another aspect, health care system 1200 using an acupoint work piece to perform a health care work on a user having a body part having an acupoint, includes: health care body (1210) carrying the body part; positioning medium (524, 680, 714, 804) configured on the health care body and positioning the body part on the health care body so that the health care body and the body part have a first relative positional relationship therebetween; and computer device (1215) configured on the health care body, and controlling/monitoring the acupoint work piece to perform the health care work under a second positional relationship maintained between the health care body and the acupoint work piece, or the acupoint work piece and the acupoint.

From yet another aspect, health care system (1200) includes: health care body (1210) performing a healthcare work on a user, wherein the user has a body part having an acupoint, and the health care body supports thereon the body part for the health care work when the health care body holds an acupoint work piece thereon; positioning medium (524, 680, 714, 804) configured on the health care body and positioning the body part on the health care body so that the health care body and the body part have a first specific positional relationship therebetween; and computer device (1215) configured on the health care body, and controlling/monitoring the acupoint work piece to perform the health care work under a second positional relationship maintained between the health care body and the acupoint work piece, or the acupoint work piece and the acupoint.

Although the possible implementations of each of the above-mentioned embodiments have not been listed in detail, there are a lot of mutual references or substitutions among the various embodiments, and thus, an embodiment is likely to be a reference or alternative schemes for other embodiments. Because the content of this case is already quite long, it will not be detailed here in order to save the burden of all parties.

In summary, it can be understood by those skilled in the art that a variety of modifications and variations may be made to the present invention without departing from the spirit or scope of the present invention defined in the appended claims, and their equivalents.

The invention claimed is:

1. A health care device, comprising:

a health care body configured to carry and position thereon a body part of a user to maintain a first specific positional relationship with the body part, wherein the body part includes a first surface contacting with the health care body, a second surface opposite to the first surface, and an acupoint located on the second surface, and the health care body supports thereon the first surface;

a work base configured on the health care body;

an acupoint work piece configured to perform a health care work directly on the acupoint, wherein the acupoint work piece has a work body and the work body is a slender pneumatic cylinder having a piston rod; and a work piece holder having:

a first end configured on the work base; and a second end configured to hold the acupoint work piece thereon, such that:

the second end or the acupoint work piece is held in a second specific positional relationship with the acupoint; and the acupoint work piece is thereby enabled to perform a health care work on the user above or over the second surface through the acupoint below the second surface under the first and second specific positional relationships.

2. The health care device as claimed in claim 1, wherein:

the work body has a first end and a second end, and the first end of the work body connects to the second end of the work piece holder; and the acupoint work piece further includes a health care medium configured on the second end of the work body, and has:

a crankshaft rotatably configured on the second end of the work body;

a point opening located on a bottom of the work body; and a main connecting piece connected between the piston rod and the crankshaft, wherein the piston rod drives the crankshaft to perform the health care work via the point opening.

3. The health care device as claimed in claim 2, wherein the first end of the work body has a thread, and a working medium of the health care medium is a microwave, a millimeter wave, a radiation heat, a magnetism, a frequency signal, a microcurrent or a wormwood heat.

4. The health care device as claimed in claim 2, wherein the acupoint work piece further includes a ring piece, an upper connecting ring and a work ring, and the main connecting piece has a first end and a second end, wherein:

the ring piece is fixed on the second end of the main connecting piece;

the upper connecting ring is connected between the piston rod and the ring piece;

the work ring is fixed on the first end of the main connecting piece, and is movably buckled to the crankshaft;

the health care medium further includes a rubber pad configured between the piston rod and the point opening; and the work ring performs a massage operation on the acupoint through the rubber pad.

5. The health care device as claimed in claim 2, wherein the point opening is a round opening or an arc slot.

6. The health care device as claimed in claim 2, wherein:

a connector is fixed on the second end of the work piece holder, has an internal thread, and is cylindrical; and the first end of the work body is columnar and is screwed to the internal thread, whereby a screwed depth or a screwed level between the connector and the first end of the work body determines a work pressure of the body part or the acupoint exerted by the health care medium.

7. The health care device as claimed in claim 1, wherein the second end of the work piece holder is the acupoint work piece.

8. The health care device as claimed in claim 7, wherein:

the work base has a longitudinal through hole;

the first end of the work piece holder has an annular groove;

the work piece holder has a C-clamp;

when the first end of the work piece holder passes through the longitudinal through hole, the C-clamp is fastened to the annular groove to position the acupoint work piece with the work base;

an end section of the longitudinal through hole is a threaded hole; and the first end of the work piece holder has a threaded section being tightly fitted with the threaded hole at a specific angle to adjust a work angle of the acupoint work piece with respect to the acupoint.

9. The health care device as claimed in claim 1, further comprising a moving device configured between the work base and the health care body, and moving the acupoint work piece to have a specific orientation with respect to the health care body.

10. The health care device as claimed in claim 1, further comprising an angle controller including:

an angle control assembly configured on the work base; and a work piece supporter connected to the angle control assembly and the first end of the work piece holder, wherein the angle control assembly controls the work piece supporter to ensure the acupoint work piece on the work piece holder to have a specific angle with respect to the work base or the acupoint.

11. The health care device as claimed in claim 10, wherein the work piece holder has a fixing piece and a threaded barrel, and the threaded barrel is fixed on the work piece supporter through the fixing piece.

12. The health care device as claimed in claim 10, wherein the work piece holder has a fixing piece and a pair of elastic jaws, the fixing piece is fixed on the work piece supporter through a screw or a rivet, and the pair of elastic jaws has an elastic holding part for holding the acupoint work piece.

13. The health care device as claimed in claim 1, wherein the work piece holder is a robotic arm device including:

a work platform configured on the work base;

a rotating platform rotatably carried on the work platform;

a connecting base pivotally connected on the rotating platform;

an extension base pivotally connected on the connecting base;

a rotating head rotatably carried on the extension base; and a holding part pivotally connected on the rotating head for holding the acupoint work piece.

14. The health care device as claimed in claim 13, wherein the holding part includes two jaws, each of which has a holding surface, and the acupoint work piece is held between the two holding surfaces.

15. The health care device as claimed in claim 13, wherein the robotic arm device further includes a needle inserting mechanism pivotally configured on the rotating head, the holding part is longitudinally movably figured on the needle inserting mechanism, and the needle inserting mechanism enables the acupoint work piece to perform the health care work on the body part with a specific control parameter.

16. The health care device as claimed in claim 15, wherein the specific control parameter is a speed control parameter or a polarization parameter.

17. A health care device comprising:

a health care body configured to carry thereon a body part of a user having a first surface contacting with the health care body, a second surface opposite to the first surface, and an acupoint, and to maintain a first specific positional relationship with the body part, and the health care body supports thereon the first surface;

a work base configured on the health care body;

a work piece holder including a first end and a second end, wherein the first end is connected to the work base; and an acupoint work piece including a health care medium, mounted on the second work piece holder end, such that the acupoint work piece is kept in a second specific positional relationship with the acupoint, to enable the acupoint work piece to perform the health care work on the user above or over the second surface through the acupoint below the second surface under the first and second specific positional relationships, wherein the acupoint work piece includes a work body being a slender pneumatic cylinder having a piston rod.

18. The health care device as claimed in claim 17, wherein the work body has a first end and a second end, the first end of the work body is connected to the second end of the work piece holder, and the health care medium is configured on the second end of the work body.

19. The health care device as claimed in claim 18, wherein the work piece holder is a robotic arm device.

20. An acupoint work piece for health care configured on a health care body, the health care body configured to perform a health care work on a user, wherein the user has a body part having a first surface contacting with the health care body, a second surface opposite to the first surface, and an acupoint located on the second surface, the health care body has a work base and carries and positions thereon the body part to maintain a first specific positional relationship with the body part, the work base configured on the health care body supporting thereon the first surface and the acupoint work piece comprises:

a work body having a first end and a second end, wherein the first end is connected to the work base and the work body is a slender pneumatic cylinder having a piston rod; and a health care medium configured on the second end and having a second specific positional relationship with the acupoint, such that the acupoint work piece is configured to perform a health care work on the user above or over the second surface through the acupoint below the second surface under the first and second specific positional relationships.

* * * * *